United States Patent
Lee et al.

(10) Patent No.: US 9,976,124 B2
(45) Date of Patent: May 22, 2018

(54) **HYDROGENASE ISOLATED FROM *THERMOCOCCUS* SPP**

(71) Applicant: KOREA OCEAN RESEARCH & DEVELOPMENT INSTITUTE, Gyeonggi-Do (KR)

(72) Inventors: Jung Hyun Lee, Gyeonggi-do (KR); Sung Gyun Kang, Gyeonggi-do (KR); Hyun Sook Lee, Gyeonggi-do (KR); Sang Jin Kim, Gyeonggi-do (KR); Kae Kyoung Kwon, Gyeonggi-do (KR); Sun Shin Cha, Gyeonggi-do (KR); Jung Ho Jeon, Gyeonggi-do (KR); Yona Cho, Gyeonggi-do (KR); Yun Jae Kim, Gyeonggi-do (KR); Seung Seop Bae, Gyeonggi-do (KR); Jae Kyu Lim, Gyeonggi-do (KR); In Soon Jeong, Gyeongsangnam-do (KR)

(73) Assignee: KOREA OCEAN RESEARCH & DEVELOPMENT INSTITUTE, Gyeonggi-Do (KR)

(*) Notice: Subject to any disclaimer, the term of this patent is extended or adjusted under 35 U.S.C. 154(b) by 0 days. days.

(21) Appl. No.: 14/093,150

(22) Filed: Nov. 29, 2013

(65) Prior Publication Data
US 2014/0248683 A1 Sep. 4, 2014

Related U.S. Application Data

(62) Division of application No. 12/746,090, filed as application No. PCT/KR2009/005060 on Sep. 7, 2009, now Pat. No. 8,597,926.

(30) Foreign Application Priority Data

Sep. 5, 2008 (KR) .................. 10-2008-0087794
Sep. 5, 2008 (KR) .................. 10-2008-0087806

(51) Int. Cl.
| | |
|---|---|
| C12N 9/02 | (2006.01) |
| C12N 15/53 | (2006.01) |
| C12N 1/21 | (2006.01) |
| C12N 9/04 | (2006.01) |
| C12P 3/00 | (2006.01) |
| C12R 1/01 | (2006.01) |

(52) U.S. Cl.
CPC ......... *C12N 9/0006* (2013.01); *C12N 9/0067* (2013.01); *C12P 3/00* (2013.01); *C12R 1/01* (2013.01); *Y02P 20/132* (2015.11); *Y02P 20/52* (2015.11)

(58) Field of Classification Search
None
See application file for complete search history.

(56) References Cited

U.S. PATENT DOCUMENTS

2010/0311142 A1* 12/2010 Lee .................. C12N 9/0067
435/168

OTHER PUBLICATIONS

Bae et al., Thermococcus onnurineus sp. nov., a Hyperthermophilic Archaeon Isolated from a Deep-Sea Hydrothermal Vent Area at the Pacmanus Field, J. Microbiol. Biotechnol., 2006, 16, 1826-81.*
Godfroy et al., Thermococcus hydrothermalis sp. nov., a new hyperthermophilic archaeon isolated from a deep-sea hydrothermal vent, Int. J. Syst. Bacteriol., 1997, 47, 622-26.*
Uniprot, Accession No. B6YTW6, Jan. 2009, www.uniprot.org.*
Menon et al., Cloning and Sequencing of a Putative *Escherichia coli* [NiFe] Hydrogenase-1 Operon Containing Six Open Reading Frames, J. Bacteriol., 1990, 1969-77.*
Takacs et al., Formate hydrogenlyase in the hyperthermophilic archaeon, Thermococcus litoralis, BMC Microbiol., Jun. 2008, 8, 88.*
Ramos et al., A high-copy T7 *Escherichia coli* expression vector for the production of recombinant proteins with a minimal N-terminal His-tagged fusion peptide, Brazilian J. Med. Biol. Res., 2004, 37, 1103-09.*
Lee et al., The Complete Genome Sequence of Thermococcus onnurineus NA1 Reveals a Mixed Heterotrophic and Carboxydotrophic Metabolism, J. Bacteriol., Sep. 12, 2008, 190, 7491-99.*

* cited by examiner

*Primary Examiner* — Robert B Mondesi
*Assistant Examiner* — Todd M Epstein
(74) *Attorney, Agent, or Firm* — The PL Law Group, PLLC

(57) ABSTRACT

The present invention relates to novel hydrogenases isolated from novel hyperthermophilic strains belonging to *Thermococcus* spp., genes encoding the hydrogenases, and methods of producing hydrogen using strains having the genes. According to the hydrogen production methods of the invention, a large amount of hydrogen can be produced merely by culturing the strains in specific culture conditions. Thus, the methods of the invention have advantages in that they are more economic and efficient than existing hydrogen production methods and can produce hydrogen even at high temperature.

4 Claims, 18 Drawing Sheets

FIG. 1B

INFORMATION STORAGE AND PROCESSING
- [J] Translation, ribosomal structure and biogenesis
- [A] RNA processing and modification
- [K] Transcription
- [L] Replication, recombination and repair
- [B] Chromatin structure and dynamics

CELLULAR PROCESSES AND SIGNALING
- [D] Cell cycle control, cell division, chromosome partitioning
- [Y] Nuclear structure
- [V] Defense mechanisms
- [T] Signal transduction mechanisms
- [M] Cell wall/membrane/envelope biogenesis
- [N] Cell motility
- [Z] Cytoskeleton
- [W] Extracellular structures
- [U] Intracellular trafficking, secretion, and vesicular transport

- [O] Posttranslational modification, protein turnover, chaperones

METABOLISM
- [C] Energy production and conversion
- [G] Carbohydrate transport and metabolism
- [E] Amino acid transport and metabolism
- [F] Nucleotide transport and metabolism
- [H] Coenzyme transport and metabolism
- [I] Lipid transport and metabolism
- [P] Inorganic ion transport and metabolism
- [Q] Secondary metabolites biosynthesis, transport and catabolism

POORLY CHARACTERIZED
- [R] General function prediction only
- [S] Function unknown

- —

HYDROGENASE ISOLATED FROM *THERMOCOCCUS* SPP

CROSS REFERENCE TO RELATED APPLICATIONS AND CLAIM OF PRIORITY

This application is a divisional application of application Ser. No. 12/746,090, filed Jul. 8, 2010, which is a National Stage entry from International Application No. PCT/KR2009/005060, filed Sep. 7, 2009, which claims priority to Korean Patent Application Nos. 10-2008-0087794, filed Sep. 5, 2008, and 10-2008-0087806, filed Sep. 5, 2008, entire contents of which are incorporated herein by reference.

BACKGROUND

1. Technical Field

The present invention relates to novel hydrogenases isolated from novel strains belonging to the genus *Thermococcus*, genes encoding the same, and methods of producing hydrogen using strains having the genes.

2. Background Art

Hydrogen energy is receiving attention as a next-generation energy source that can substitute for fossil fuels, because its calorific value per unit weight is at least three times higher than that of petroleum oils, while it does not emit substances that can adversely affect the environment, such as carbon dioxide, NOx and SOx.

Conventional processes for producing hydrogen include electrolysis of water, and the thermal-cracking or steam reforming of natural gas or naphtha. However, these production processes have a problem in that they require fossil fuels to provide high-temperature and high-pressure conditions. Also, these methods generate mixed gases containing carbon monoxide, and thus require a difficult process of removing carbon monoxide from the mixed gases.

On the other hand, biological methods of producing hydrogen using microorganisms have advantages in that it is not needed to make high-temperature and high-pressure conditions by introducing separate energy and in that the produced gases contain no carbon monoxide. Such biological hydrogen production methods can be broadly classified into methods utilizing photosynthetic microorganisms and methods utilizing non-photosynthetic microorganisms (mainly anaerobic microorganisms). Examples of the former methods include a method described in Korean Patent Registration No. 10-0680624, entitled "A method of producing hydrogen using the photosynthetic bacteria *Rhodobacter sphaeroides* strain having high hydrogen productivity at high salt concentration."

However, the technology of culturing photosynthetic bacteria at high concentration using light as an energy source is not yet sufficiently developed, and prior photosynthetic bacteria have a shortcoming in that substrate inhibition is severe when a substrate of high partial pressure exists. Also, these bacteria have a problem in that their hydrogen production capacity can be maintained only in the presence of light.

Accordingly, attempts to produce hydrogen using microorganisms that can produce hydrogen using organic carbon have been continuously made, and examples thereof include Korean Patent Registration No. 10-0315663, entitled "*Citrobacter* sp. Y19 and production of hydrogen using the same", and Korean Patent Registration No. 10-0315662, entitled "*Rhodopseduomonas palustris* P4 and production of hydrogen using the same".

The present inventors previously filed a patent application relating to novel proteins isolated from novel hyperthermophilic *Thermococcus onnurineus* NA1 (accession number KCTC 10859BP) and genes encoding the same on Sep. 5, 2008 (Korean Patent Application No. 10-2008-0087794), and the present invention particularly relates to genes related to hydrogen production among the proteins and genes disclosed in the patent application. The present inventors have carried out experiments on the hydrogen production capacity of the above-described strain and, as a result, have found that the strain produces a large amount of hydrogen even in a high-temperature environment, and have also found novel hydrogenases which are highly expressed, particularly in culture conditions supplemented with carbon monoxide (CO) or formate, thereby completing the present invention.

SUMMARY

It is an object of the present invention to provide hydrogenases isolated from hyperthermophilic *Thermococcus* spp. which can produce hydrogen even in a high-temperature environment, genes encoding the same, and methods of efficiently producing hydrogen using strains having the genes.

To achieve the above object, the present invention provides hydrogenases isolated from the *Thermococcus* spp. strain capable of producing hydrogen in aerobic culture conditions, and genes encoding the same. Also, the present invention provides a method of producing hydrogen by culturing the strain, and a method of producing hydrogen using the genes.

In a first aspect, the present invention provides hydrogenases which are produced by the novel hyperthermophilic strain *Thermococcus onnurineus* NA1 (accession number: KCTC 10859BP). *T. onnurineus* NA1 has eight novel hydrogenase gene clusters, and the amino acid sequences of hydrogenases belonging thereto are shown in SEQ ID NO. 1 to SEQ ID NO: 8.

In a second aspect, the present invention provides genes encoding said amino acid sequences. The genes are preferably, but not limited to, genes of SEQ ID NO. 12 to SEQ ID NO: 19 (the amino acid sequences of SEQ ID NO. 1 to SEQ ID NO: 8 correspond to the genes of SEQ ID NO. 12 to SEQ ID NO: 19, respectively).

In a third aspect, the present invention provides a method of producing hydrogen by culturing *Thermococcus* spp. The method comprises the steps of: 1) preparing a medium in a culture vessel; 2) culturing *Thermococcus* spp. in the culture vessel; 3) extracting hydrogen from the culture vessel. The *Thermococcus* spp. is preferably *Thermococcus onnurineus* NA1 (accession number: KCTC 10859BP).

In addition, the medium may be a medium supplemented with one or more selected from the group consisting of carbon monoxide, formate and starch. The culturing may be carried out at a high temperature of 80° C. in an anaerobic condition.

In a fourth aspect, the present invention provides a dehydrogenase comprising at least one amino acid sequence selected from the group consisting of SEQ ID NO: 9 to SEQ ID NO: 11.

In a fifth aspect, the present invention provides a gene encoding the dehydrogenase. Preferably, the gene has a base sequence selected from SEQ ID NO: 20 to SEQ ID NO: 22 (the amino acids of SEQ ID NOs: 9 to 11 correspond to SEQ ID NOs: 20 to 22, respectively).

In a sixth aspect, the present invention provides a recombinant vector comprising genes that are organized in a CODH-MCH-MNH3 hydrogenase cluster in *T. onnurineus* NA1, wherein the genes are all operably linked. Preferably, the genes include, but are not limited to, genes of SEQ ID NO: 21 (CODH dehydrogenase) and SEQ ID NO: 16 (MCH hydrogenase). In addition, the present invention provides a host cell transformed with the recombinant vector.

Also, the present invention provides a method of producing hydrogen using said transformant, the method comprising the steps of: preparing a medium in a culture vessel; feeding carbon monoxide into a gas phase of the culture vessel; culturing said transformant in the culture vessel; and extracting hydrogen from the culture vessel.

In a seventh aspect, the present invention provides a recombinant vector comprising genes that are organized in a FDH2-MFH2-MNH2 hydrogenase cluster in *T. onnurineus* NA1, wherein the genes are all operably linked. Preferably, the genes include, but are not limited to, genes of SEQ ID NO: 22 (FDH2 dehydrogenase) and SEQ ID NO: 18 (MFH2 hydrogenase). In addition, the present invention provides a host cell transformed with the recombinant vector.

Also, the present invention provides a method of producing hydrogen using said transformant, the method comprising the steps of: preparing a formate-containing medium in a culture vessel; culturing said transformant in the culture vessel; and extracting hydrogen from the culture vessel.

In an eighth aspect, the present invention provides a recombinant vector comprising genes that are organized in a FDH1-MFH1-MNH1 hydrogenase cluster in *T. onnurineus* NA1, wherein the genes are all operably linked. Preferably, the genes include, but are not limited to, genes of SEQ ID NO: 20 (FDH1 dehydrogenase) and SEQ ID NO: 13 (MFH1 hydrogenase). In addition, the present invention provides a host cell transformed with the recombinant vector.

Also, the present invention provides a method of producing hydrogen using said transformant, the method comprising the steps of: preparing a starch-containing medium in a culture vessel; culturing said transformant in the culture vessel; and extracting hydrogen from the culture vessel.

The hydrogen production methods according to the present invention have advantages in that they do not require high-temperature and high-pressure conditions, unlike the prior chemical hydrogen production methods, can generate hydrogen in ambient temperature and atmospheric pressure conditions, and do not generate harmful byproducts. Also, the methods of the present invention have advantages in that they can produce high-purity hydrogen at high efficiency compared to the prior art methods of producing hydrogen using microorganisms and can produce hydrogen even in high-temperature conditions.

Accordingly, the present invention has an economic advantage in that it allows high-temperature carbon monoxide discharged from petroleum purification processes and the like to be used directly for hydrogen production without a separate cooling process after capturing the carbon monoxide. Also, the present invention is useful for air conditioning.

BRIEF DESCRIPTION OF THE DRAWINGS

FIGS. 1A and 1B present a Venn diagram showing the shared and unique portions of the proteome of four Thermococcales strains, *T. onnurineus* NA1 (NA1), *T. kodakaraensis, P. furiosus*, and *P. abyssi*. The protein sets for the strains were obtained from the RefSeq collection in NCBI.

| No. | Gene |
|---|---|
| 1 | Aeropyrum_pernix |
| 2 | Pyrobaculum_aerophilum |
| 3 | Sulfolobus_acidocaldarius_DSM_639 |
| 4 | Sulfolobus_solfataricus |
| 5 | Sulfolobus_tokodaii |
| 6 | Haloarcula_marismortui_ATCC_43049 |
| 7 | Natronomonas_pharaonis |
| 8 | Halobacterium_sp |
| 9 | Haloquadratum_walsbyi |
| 10 | Methanococcoides_burtonii_DSM_6242 |
| 11 | Picrophilus_torridus_DSM_9790 |
| 12 | Thermoplasma_acidophilum |
| 13 | Thermoplasma_volcanium |
| 14 | Methanosaeta_thermophila_PT |
| 15 | Pyrobaculum_islandicum_DSM_4184 |
| 16 | Thermofilum_pendens_Hrk_5 |
| 17 | Pyrococcus_abyssi |
| 18 | Pyrococcus_furiosus |
| 19 | Pyrococcus_horikoshii |
| 20 | Thermococcus_kodakaraensis_KOD1 |
| 21 | Archaeoglobus_fulgidus |
| 22 | Methanosarcina_barkeri_fusaro |
| 23 | Methanosarcina_mazei |
| 24 | Methanosarcina_acetivorans |
| 25 | Methanospirillum_hungatei_JF-1 |
| 26 | Methanobacterium_thermoautotrophicum |
| 27 | Methanococcus_jannaschii |
| 28 | Methanococcus_maripaludis_S2 |
| 29 | Methanosphaera_stadtmanae |
| 30 | Methanopyrus_kandleri |
| 31 | Nanoarchaeum_equitans |

Figure 4:
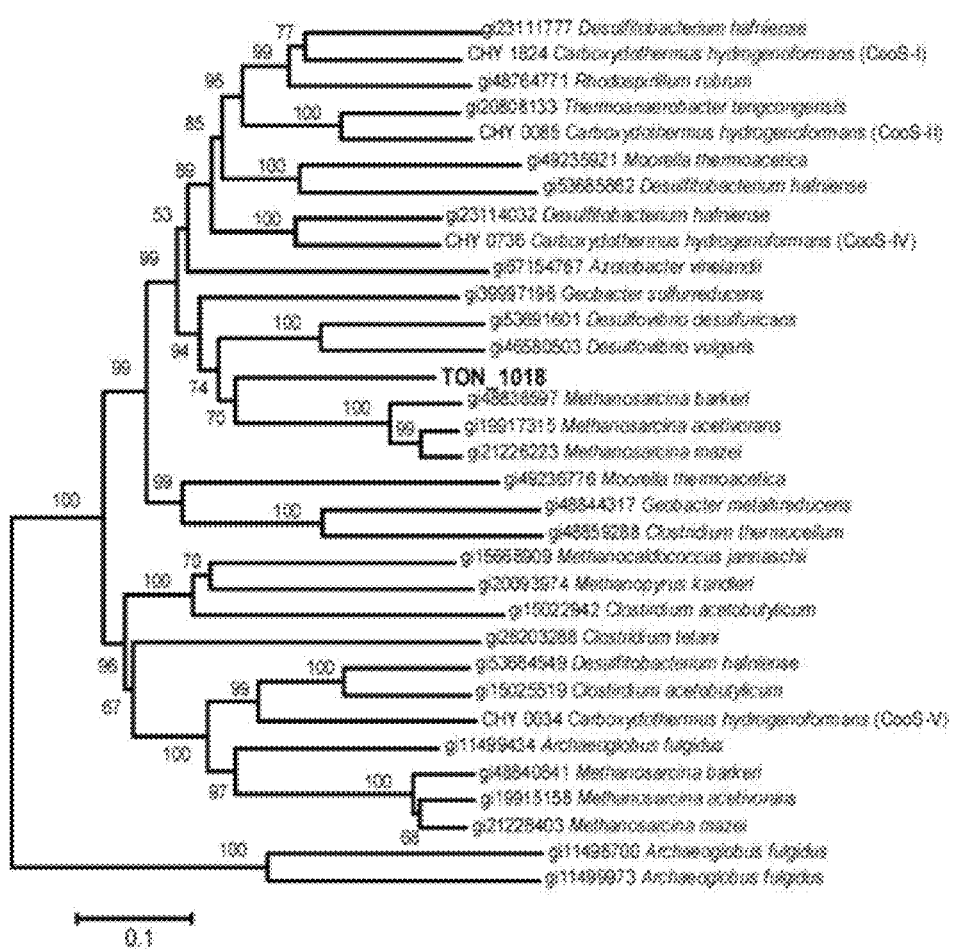
Figure 5:
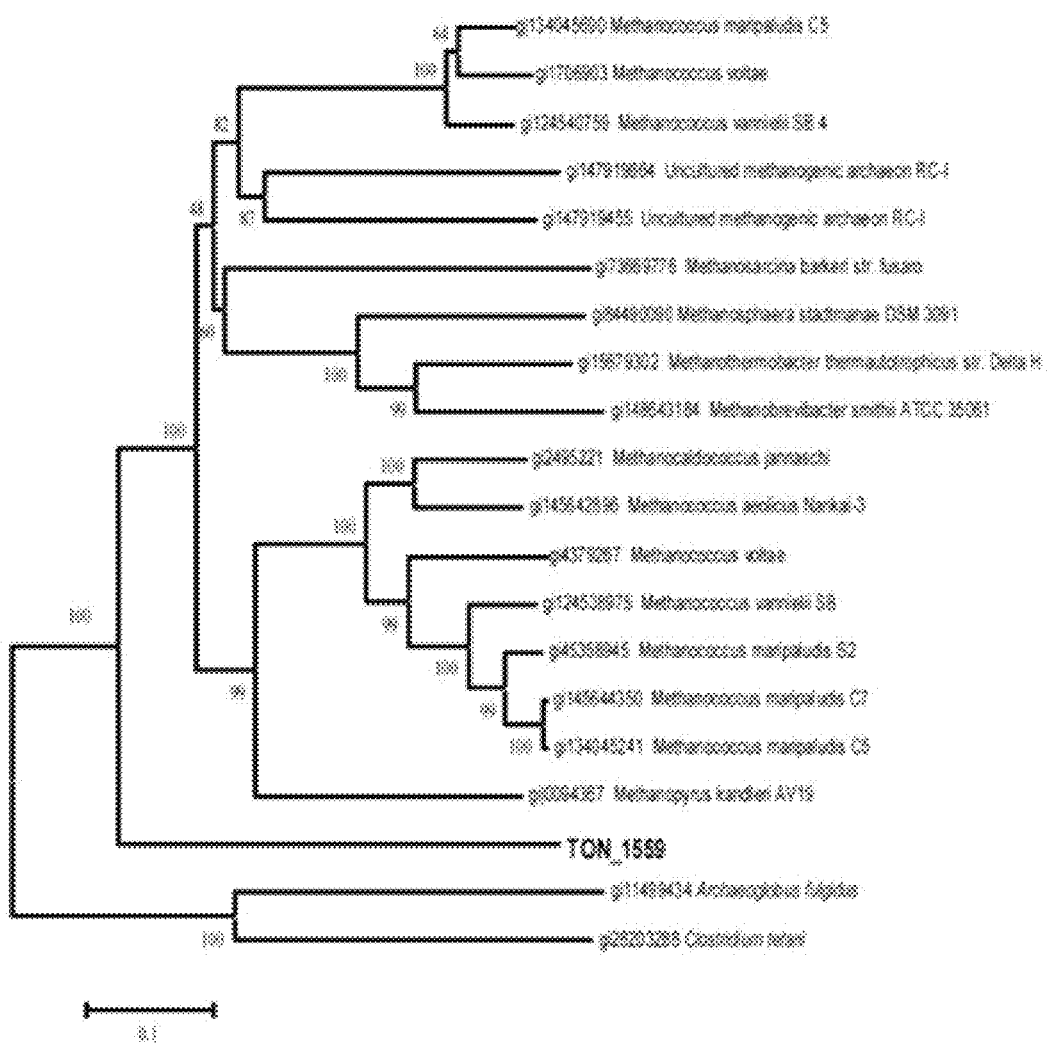

FIGS. 4 and 5 show a comparison of the α subunits of CODH and F420 hydrogenase proteins. FIG. 4 is the phylogenetic tree of CODH, and FIG. 5 is the phylogenetic tree of the α subunit of F420 hydrogenase. Homologues of the proteins on the phylogenetic trees were obtained from the NCBI nr database.

Figure 6A:
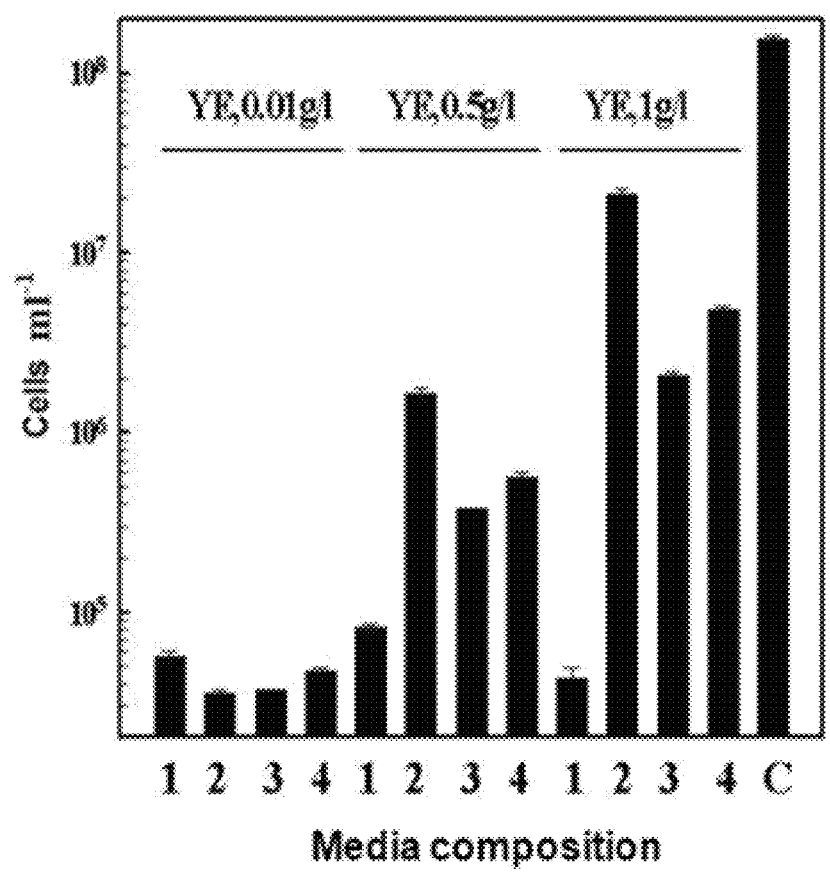
Figure 6B:
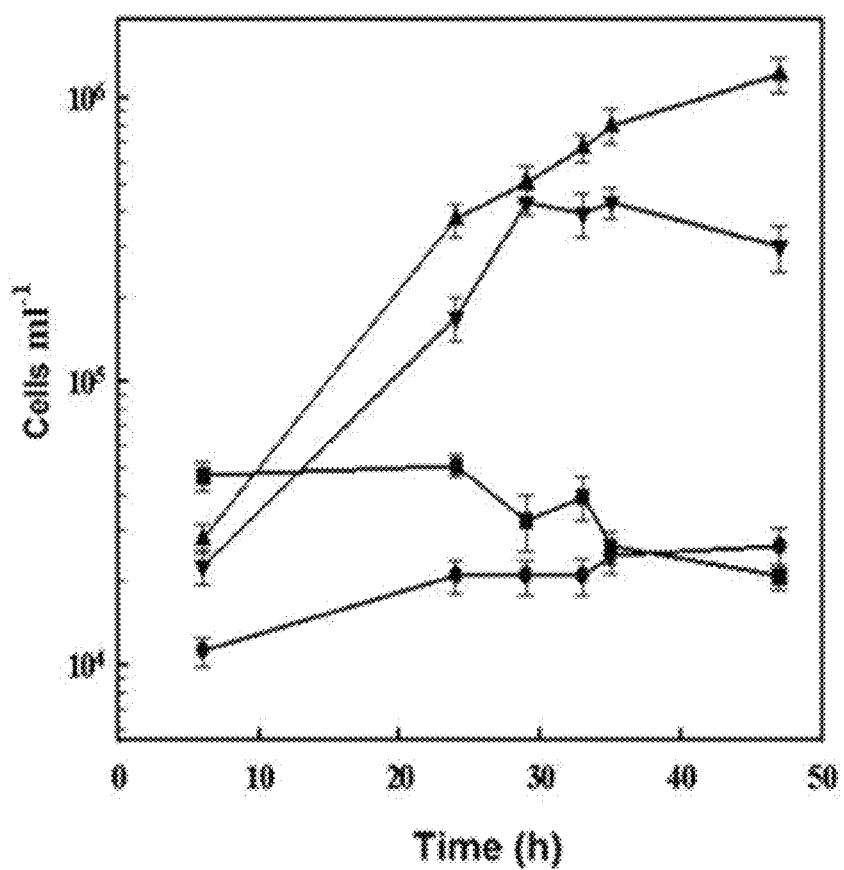
Figure 6C:
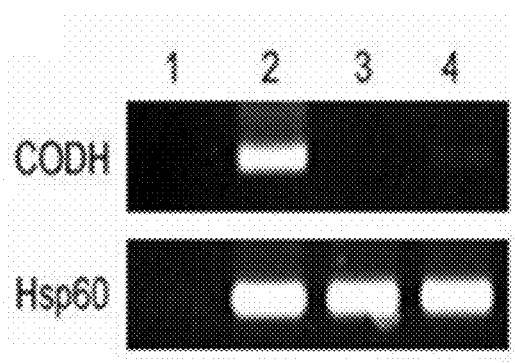

FIGS. 6A through 6C show the growth profile of *T. onnurineus* NA1 depending on CO. *T. onnurineus* NA1 was grown in medium 1 supplemented with CO (lane 2; triangles), sulfur (lane 3; squares) or both (lane 4; triangles down). Controls without supplement (lane 1; circles) and culture in YPS medium (C) were included. DAPI-stained cells were directly counted on filters by fluorescence microscopy. FIG. 6A: Effect of medium composition at various concentrations of yeast extract (YE). FIG. 6B: Growth curves of *T. onnurineus* NA1 in medium 1 with other supplements. FIG. 6C: Analysis of the transcription of the CODH gene.

Figure 7A:
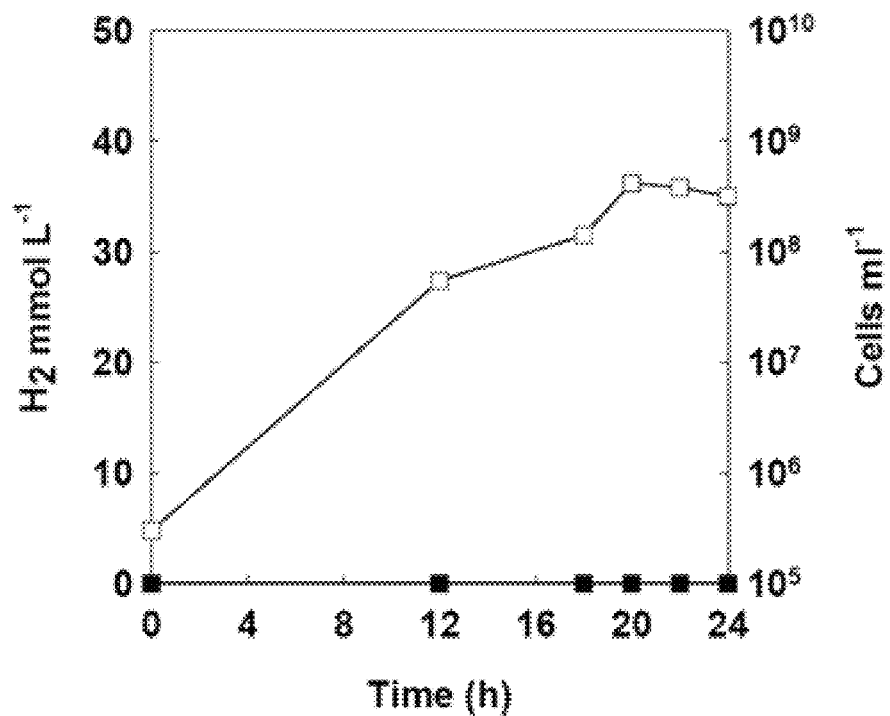
Figure 7B:
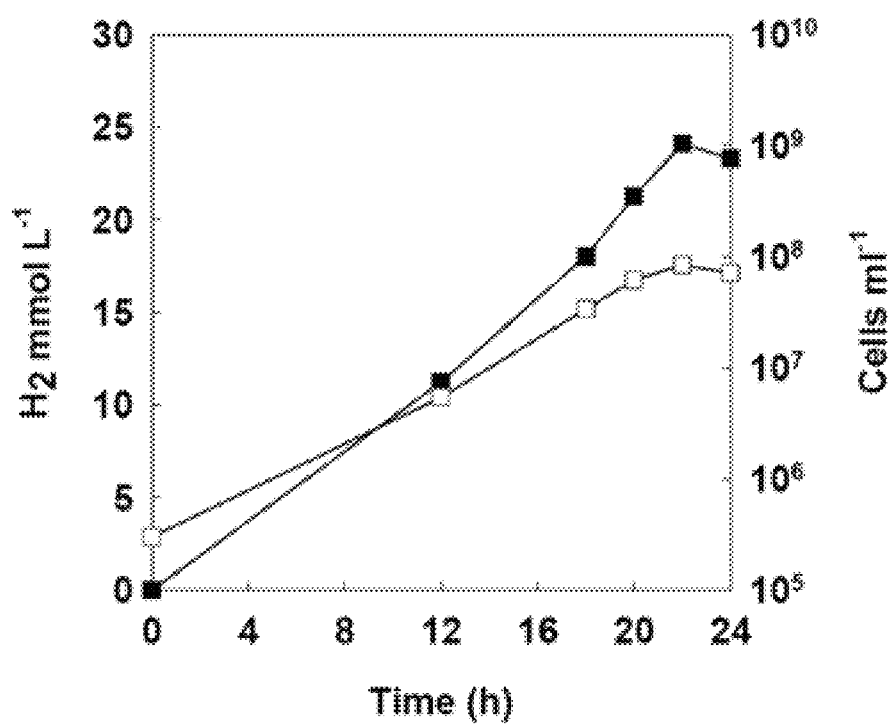

FIG. 7A shows the growth and hydrogen production of *T. onnurineus* NA1 in YPS and FIG. 7B shows the growth and hydrogen production of *T. onnurineus* NA1 in CO-containing medium. Open circles: growth; and closed circles: hydrogen production.

Figure 8A:
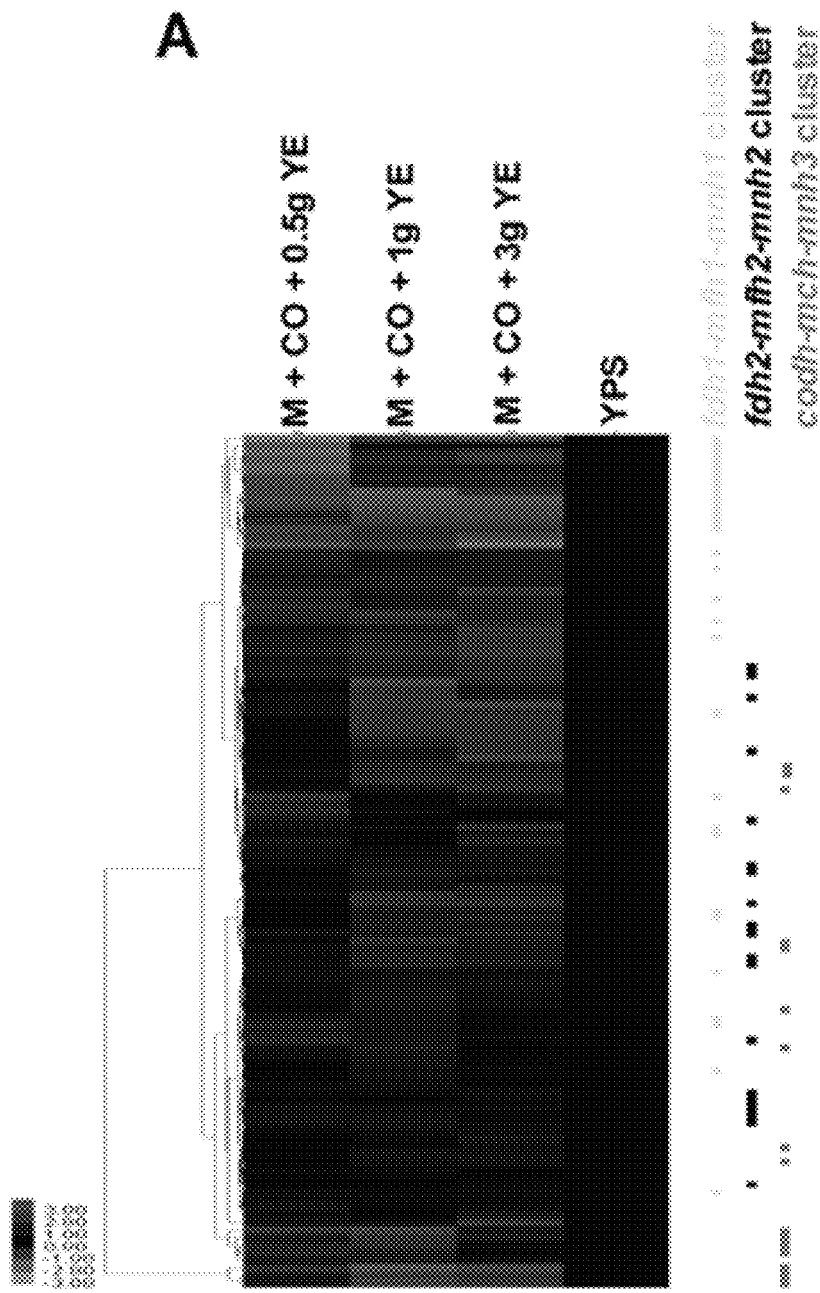
Figure 8B:
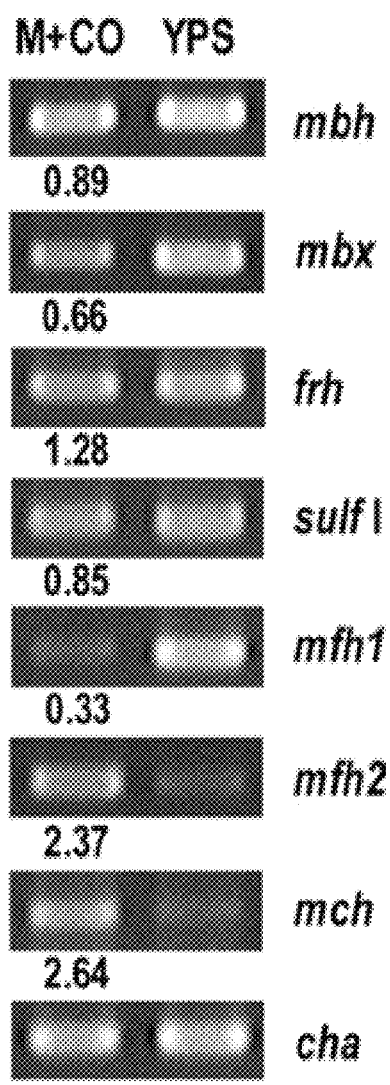

FIG. 8A shows the microarray analysis of the expression of hydrogenase gene clusters in *T. onnurineus* NA1 in YPS and FIG. 8B shows RT-PCR analysis of the expression of hydrogenase gene clusters in *T. onnurineus* NA1 in CO-containing medium. More particularly, FIG. 8A shows the microarray analysis of eight hydrogenase gene clusters in *T. onnurineus* NA1. Hierarchical clustering of the mRNA changes in CO was compared with one in an YPS growth condition as a control. Up-regulation and down-regulation were indicated by red and green, respectively. Growth conditions were indicated on top of the clustering picture. At the right side of the clustering picture, ORFs of each of codh-mch-mnh3, fdh1-mfh1-mnh1 or fdh2-mfh2-mnh2 were indicated as bars. YE: yeast extract. FIG. 8B shows the results of quantitative RT-PCR analysis in CO or YPS conditions, carried out for each of the large subunits of mbh (TON_1593), mbx (TON 0489), frh (TON_1560), sulf I (TON_0534), mch (TON_1023), mfh2 (TON_1569) and mfh1 (TON_0276) hydrogenases. The chaperonin-encoding gene (cha) was used as a control to normalize expression levels.

Figure 9A:
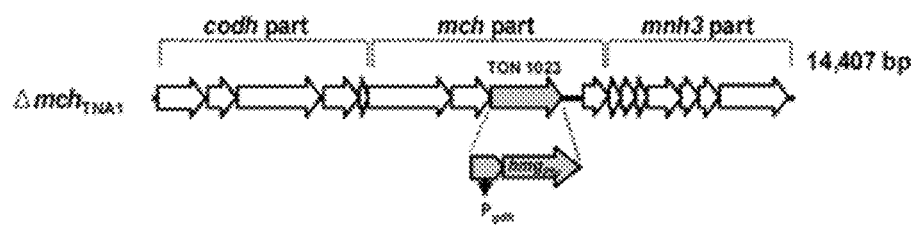
Figure 9A:
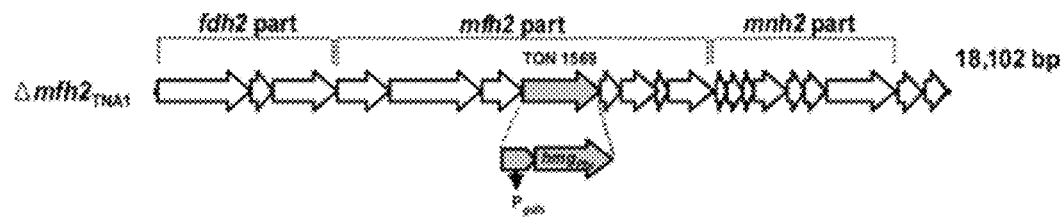
Figure 9B:
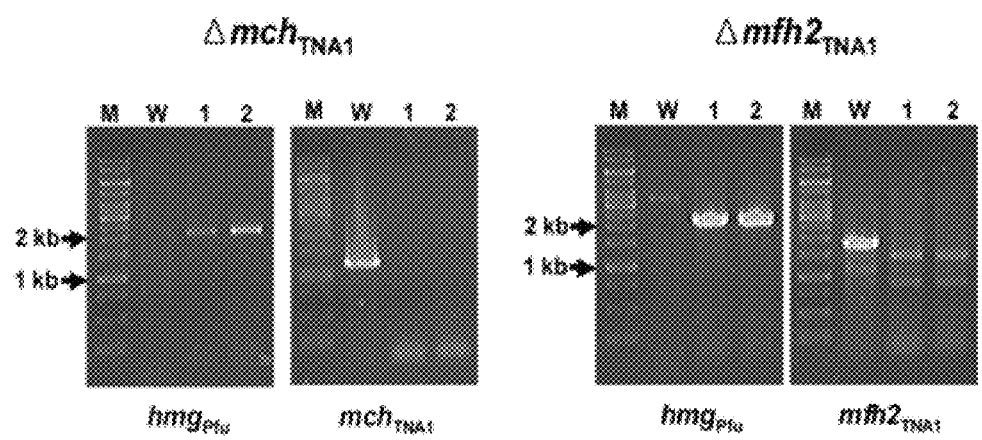

FIGS. 9A and 9B show the targeted gene disruption of the large subunit of each of mch (TON_1023) and mfh2 (TON_1569) hydrogenases. FIG. 9A shows the gene organization of each of codh-mch-mnh3 and fdh2-mfh2-mnh2 clusters in *T. onnurineus* NA1. $P_{gdh}$: the 5'-upstream promoter region of the glutamate dehydrogenase gene of *T. kodakaraensis* KOD1; and $hmg_{Pfu}$: the 3-hydroxy-methylglutaryl coenzyme A reductase gene of *Pyrococcus furiosus*. FIG. 9B shows the identification of gene disruption by PCR. The left panel shows PCR amplification with primers for the overexpression cassette ($P_{gdh}$-$hmg_{Pfu}$) region. The right panel shows PCR amplification with primers for the large subunit of each of $mch_{TNA}1$ and $mfh2_{TNA}1$ hydrogenases. M: size marker (1 kb ladder); W: wild type; lanes 1 and 2: mutant strains.

Figure 10A:
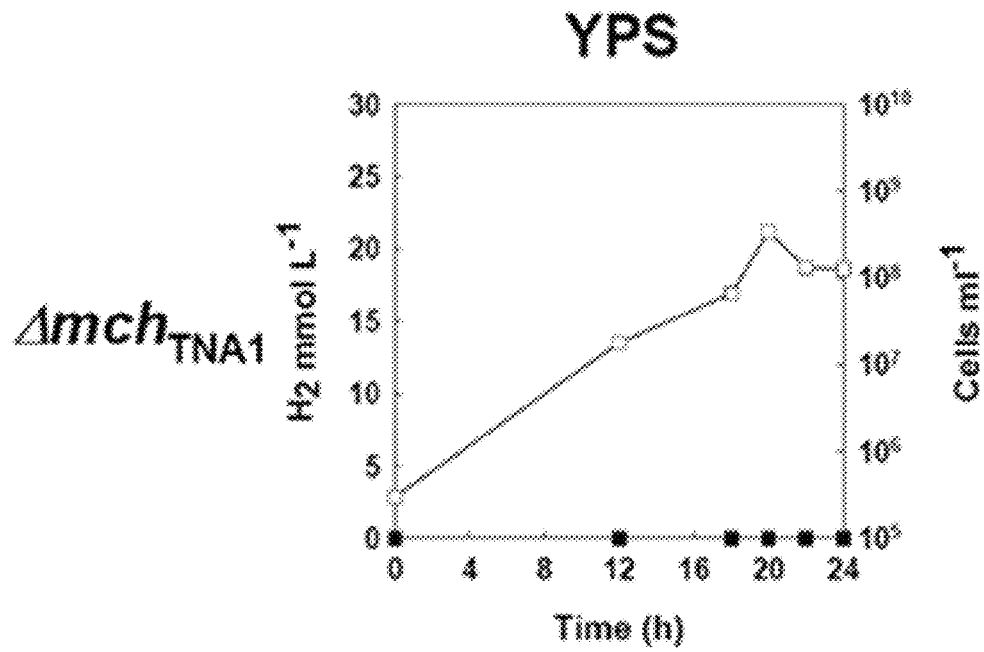
Figure 10B:
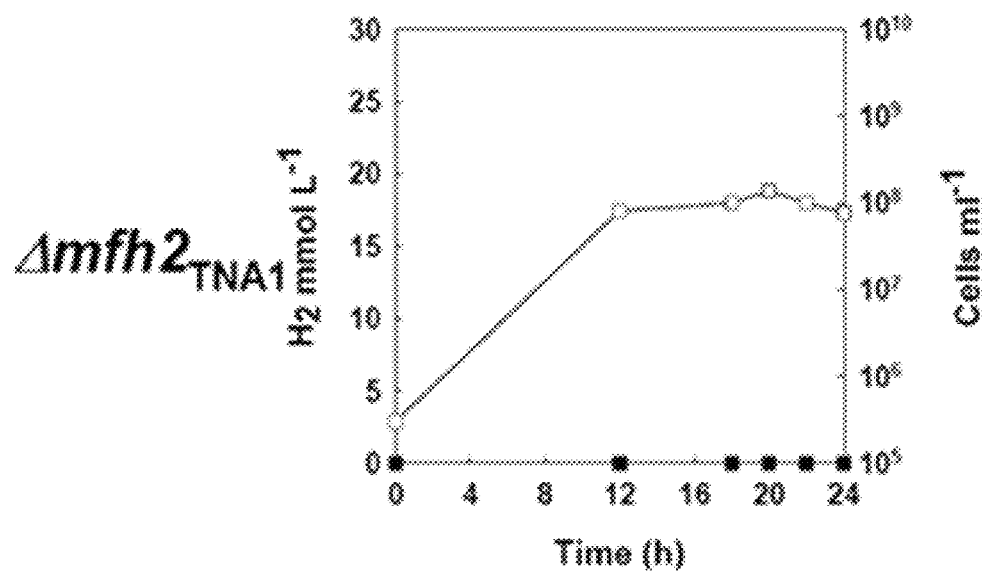
Figure 10C:
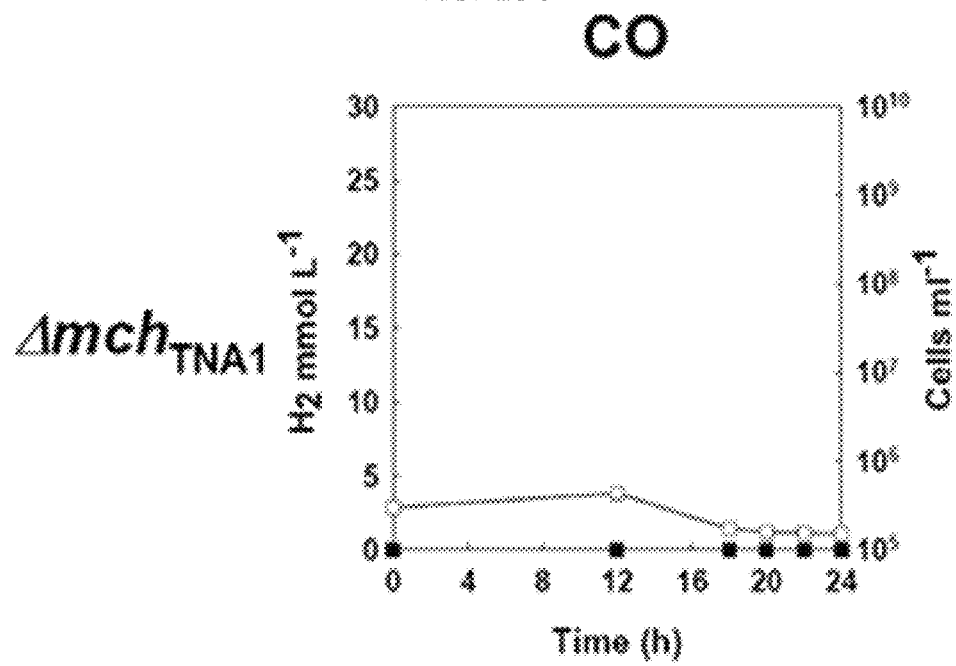
Figure 10D:
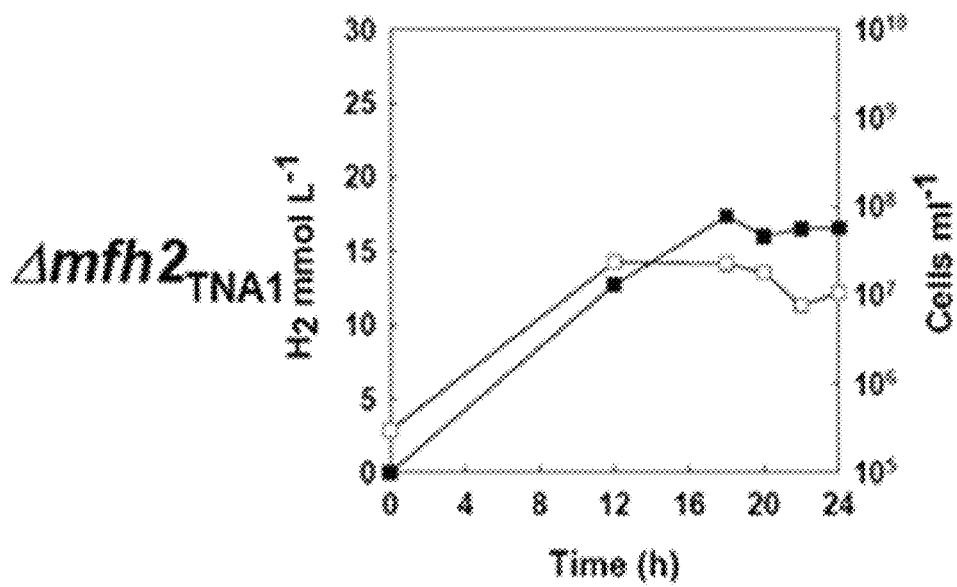

FIG. 10A shows the growth and hydrogen production of a ΔmchTNA1 mutant strain in YPS. Open circles: growth; closed circles: hydrogen production. FIG. 10B shows the growth and hydrogen production of a Δmfh2TNA1 mutant strain in YPS. FIG. 10C shows the growth and hydrogen production of a ΔmchTNA1 mutant strain in CO-containing medium. FIG. 10D shows the growth and hydrogen production of a Δmfh2TNA1 mutant strain in CO-containing medium.

DETAILED DESCRIPTION

In a first aspect, the present invention provides hydrogenases which are produced by the novel hyperthermophilic strain *Thermococcus onnurineus* NA1 (accession number: KCTC 10859BP) that produces hydrogen in anaerobic conditions. The strain was isolated from a deep-sea hydrothermal vent area at the PACMANUS field in the East Manus Basin. The isolated strain was deposited in the Korean Collection for Type Cultures (KCTC) at the Korean Research Institute of Bioscience and Biotechnology (KRIBB) on Oct. 7, 2005 and assigned accession number KCTC 10859BP on Oct. 20, 2005. The characteristics and culture methods of the strain are described in Korean Patent Application No. 10-2007-0127255 on which the present invention is based.

*T. onnurineus* NA1 has eight novel hydrogenase gene clusters. The hydrogenases are key enzymes related to the metabolism of molecular hydrogen ($H_2$) and act as catalysts in the following reversible reaction: $2H^+ + 2e^- \Leftrightarrow H_2$. Preferably, the hydrogenases belonging to the above-described clusters provide proteins and functional equivalents thereof comprising one or more amino acid sequences selected from the group consisting of SEQ ID NO: 1 to SEQ ID NO: 8. As used herein, the term "functional equivalent" is intended to include amino acid sequence variants having amino acid substitutions in some or all of the proteins, or amino acid additions or deletions in some of the proteins. The amino acid substitutions are preferably conservative substitutions. Examples of the conservative substitutions of naturally occurring amino acids are as follow: aliphatic amino acids (Gly, Ala, and Pro), hydrophobic amino acids (Ile, Leu, and Val), aromatic amino acids (Phe, Tyr, and Trp), acidic amino acids (Asp, and Glu), basic amino acids (His, Lys, Arg, Gln, and Asn), and sulfur-containing amino acids (Cys, and Met). The deletions of amino acids are preferably located in a region which is not directly involved in the activity of the hydrogenases.

In a second aspect, the present invention provides genes encoding the above-described amino acid sequences. The genes are preferably, but not limited to, genes of SEQ ID NOs: 12 to 19 (the amino acid sequences of SEQ ID NOs: 1 to 8 correspond to the genes of SEQ ID NOs: 12 to 19, respectively).

In a third aspect, the present invention provides a method of producing hydrogen by culturing *Thermococcus* spp. The method comprises the steps of 1) preparing a medium in a culture vessel; 2) culturing *Thermococcus* spp. in the culture vessel; and 3) extracting hydrogen from the culture vessel. The *Thermococcus* spp. is preferably *Thermococcus onnurineus* NA1 (accession number: KCTC 10859BP).

In addition, the medium may be a medium supplemented with one or more selected from the group consisting of carbon monoxide, formate and starch. Also, the culturing may be carried out at a high temperature of 80° C. in anaerobic conditions.

In a fourth aspect, the present invention provides a dehydrogenase comprising at least one amino acid sequence selected from the group consisting of SEQ ID NO: 9 to SEQ ID NO: 11. The dehydrogenase, Fdh1(SEQ ID NO: 20), Fdh2(SEQ ID NO: 22) and CODH(SEQ ID NO: 21), respectively may be carried out by cluster with hydrogenase MFH1, MFH2 and MCH hydrogenase.

In a fifth aspect, the present invention provides a gene encoding said dehydrogenase. Preferably, the gene is selected from genes of SEQ ID NO: 20 to SEQ ID NO: 22 (the amino acid sequences of SEQ ID NOs: 9 to 11 correspond to the genes of SEQ ID NOs: 20 to 22, respectively).

In a sixth aspect, the present invention provides a recombinant vector comprising genes that are organized in a CODH-MCH-MNH3 hydrogenase cluster in *T. onnurineus* NA1, wherein the genes are all operably linked. Preferably, the genes include, but are not limited to, genes of SEQ ID NO: 21 (CODH dehydrogenase) and SEQ ID NO: 16 (MCH hydrogenase). As used herein, the term "vector" means a nucleic acid molecule that can carry another nucleic acid bound thereto.

As an expression vector which can synthesize a protein encoded by a recombinant gene carried by said vector, a plasmid, cosmid or phage may be used. A preferred vector is a vector that can self-replicate and express a nucleic acid bound thereto.

In addition, the present invention provides a host cell transformed with the recombinant vector. The recombinant vector can be used to transform cells such as prokaryotic, fungal, plant and animal cells so as to prepare transformed cells which can produce hydrogen at high efficiency. As used herein, the term "transformation" means that foreign DNA or RNA is absorbed into cells to change the genotype of the cells. A public announced transformation method along each cell can be used to make the host cell.

Also, the present invention provides a method of producing hydrogen using said transformant, the method comprising the step of: preparing a medium in a culture vessel; feeding carbon monoxide into a gas phase of the culture medium; culturing said transformant in the culture vessel; and extracting hydrogen from the culture vessel.

In a seventh aspect, the present invention provides a recombinant vector comprising genes that are organized in a FDH2-MFH2-MNH2 hydrogenase cluster in *T. onnurineus* NA1, wherein the genes are all operably linked. Preferably, the genes include, but are not limited to, genes of SEQ ID NO: 22 (FDH2 dehydrogenase) and SEQ ID NO: 18 (MFH2 hydrogenase). In addition, the present invention provides a host cell transformed with the recombinant vector.

Particulars regarding the "vector", "transformation" and "host cell" are as described in the above sixth aspect.

Also, the present invention provides a method of producing hydrogen using said transformant, the method comprising the steps of: preparing a formate-containing medium in a culture vessel; culturing said transformant in the culture vessel; and extracting hydrogen from the culture vessel.

In an eighth aspect, the present invention provides a recombinant vector comprising genes that are organized in a FDH1-MFH1-MNH1 hydrogenase cluster in *T. onnurineus* NA1, wherein the genes are all operably linked. Preferably, the genes include, but are not limited to, genes of SEQ ID NO: 20 (FDH1 dehydrogenase) and SEQ ID NO: 13 (MFH1 hydrogenase). In addition, the present invention provides a host cell transformed with the recombinant vector.

Particulars regarding the "vector", "transformation" and "host cell" are as described in the above sixth aspect.

Also, the present invention provides a method of producing hydrogen using said transformant, the method comprising the steps of: preparing a starch-containing medium in a culture vessel; culturing said transformant in the culture vessel; and extracting hydrogen from the culture vessel.

Hereinafter, the present invention will be described in further detail with reference to examples. It is to be understood, however, that these examples are for illustrative purposes only and are not to be construed to limit the scope of the present invention.

EXAMPLE 1

Analysis of Hydrogenase Genes of *Thermococcus onnurineus* NA1 Strain (1) Test Methods
1) Culture Conditions For routine cultivation, cells were grown anaerobically at 80° C. in a yeast extract-peptone-sulfur (YPS) medium (Holden et al. 2001). Physiological tests were performed using modified medium 1 (Sokolova, T. G., C. Jeanthon, N. A Kostrikina, N. A. Chernyh, A. V. Lebedinsky, E. Stackebrandt, and E. A. Bonch-Osmolovskaya. 2004. The first evidence of anaerobic CO oxidation coupled with $H_2$ production by a hyperthermophilic archaeon isolated from a deep-sea hydrothermal vent. Extremophiles 8:317-323) supplemented with 1 ml of a trace element mixture, 1 ml of vitamin solution (Balch, W. E., G. E. Fox, L. J. Magrum, C. R. Woese, and R. S. Wolfe. 1979. Methanogens: reevaluation of a unique biological group. Microbiol. Rev. 43:260-296), NaCl (30 g g/l), and yeast extract (0.5 g/l). The pH was adjusted to 8.0 using NaOH. The anaerobically prepared medium was dispensed into 25-ml serum bottles, and the gas phase (15 ml) was charged with $N_2/CO_2$ (80:20; 1 bar) or 100% CO. When the cells were cultured with formate or starch, 10 g/L of sodium formate (Sigma) or 5 g/L of soluble starch (Sigma) was added to the medium before autoclaving. All the cultures for physiological tests were all carried out at 80° C. for 2 days.

2) Gene Sequencing

The genome sequence of *T. onnurineus* NA1 was determined by whole-genome shotgun sequencing and pyrosequencing. For capillary sequencing, a 2-kb to 3-kb insert library (11,028 clones), 40-kb insert library (1,870 clones), and 35-kb insert library (288 clones) were constructed and sequenced using an ABI 3730XL sequencer (Applied Biosystems, CA). For pyrosequencing, 581,990 fragments of DNA were sequenced using a GS-20 sequencer (454 Life Sciences). The contigs generated by both sequencers were combined, and closure of the sequencing gap was performed by clone walking and PCR sequencing. ORFs and RNA genes were predicted through a combination of Glimmer 3.0 (University of Maryland), GSFinder and RBSFinder, followed by a manual ORF fitting process. After all the ORFs had been determined, further analysis of the protein sequence was performed by BLASTP searches against the nonredundant protein sequences of the National Center for Biotechnology Information (NCBI), Kyoto Encyclopedia of Genes and Genomes (KEGG), and COG (clusters of orthologous groups of proteins) databases (Tatusova, R. L., D. A. Natale, I. V. Garkavtsev, T. A. Tatusova, U. T. Shankavaram, B. S. Rao, B. Kiryutin, M. Y. Galperin, N. D. Fedorova, and E. V. Koonin. 2001. The COG database: new developments in phylogenetic classification of proteins from complete genomes. Nucleic Acids Res. 29:22-28). tRNA-Scan-SE was used for the tRNA predictions (Lowe, T. M., and S. R. Eddy. 1997. tRNAscan-SE: a program for improved detection of transfer RNA genes in genomic sequence. Nucleic Acids Res. 25:955-964).

3) Protein Analysis

*T. onnurineus* NA1 cells were suspended in 100 mM Tris-HCl buffer (pH 6.8) containing 4% sodium dodecyl sulfate (SDS) and 4 mM EDTA and boiled for 10 min, followed by centrifugation at 22,000 g for 20 min. The cell lysate was separated using 12% sodium dodecyl sulfate-polyacrylamide gel electrophoresis (SDS-PAGE), and 30 fractions were obtained based on molecular size. They were then in-gel digested using trypsin (Promega, USA) (Kim, Y. H., K. Cho, S. H. Yun, J. Y. Kim, K. H. Kwon, J. S. Yoo, and S. I. Kim. 2006. Analysis of aromatic catabolic pathways in *Pseudomonas putida* KT 2440 by combined proteomic approach: 2-DE/MS and cleavable ICAT analysis. Proteomics 6:1301-1318), and the tryptic digests were dissolved in 0.5% trifluoroacetic acid solution to be analyzed by mass spectrometry (Thermo Finnigan LTQ IT). The identities of peptides were determined using the Sequest program (Thermo Finnigan, San Jose, Calif.).

4) Total RNA Isolation and RT-PCR Analysis

A 50-ml culture of *T. onnurineus* NA1 was grown to mid-exponential growth phase in modified medium 1 supplemented with various concentrations of yeast extract under the gas phase of $N_2/CO_2$ (80:20, 1 bar) or 100% CO. Cells were harvested by centrifugation at 6,000×g for 30 min. The pellet was resuspended in 50 µl of 50 mM Tris-HCl buffer (pH 7.5) supplemented with 500 µl of Trizol reagent (Invitrogen, Carlsbad, Calif.). The cells were lysed by freezing and thawing, and then the samples were extracted with 200 µl of chloroform. The aqueous phase containing total RNA was further processed by ethanol precipitation and then resuspended in distilled water. RNA concentration and integrity were determined by measuring the absorbance at 260 and 280 nm, as well as by 0.8% agarose gel analysis. Reverse transcription and PCR amplification were carried out using SuperScript™ II reverse transcriptase (Invitrogen) according to the manufacturer's instructions. The following two sets of primers were used for amplification of CODH (carbon monoxide dehydrogenase) and Hsp60 (chaperonin) as controls:

```
CODH gene
(forward, 5'-GGACCATGTAGAATCGAYCCGTTY-3' (SEQ ID NO: 23)
and reverse, 5'-TTCRTTTCCGGTACAGCA-3' (SEQ ID NO: 24));
and Hsp60 gene
(forward, 5'-ATGGCACAGCTTAGTGGACAG-3' (SEQ ID NO: 25)
and reverse, 5'-CAAGGATTTCCTGGGCTTTCTC-3' (SEQ ID NO: 26)).
```

5) Computer Analysis

The homology search of amino acid sequences was performed using the BLAST program against the non-redundant protein database of the NCBI. A motif search for proteins having the L1 signal (C[GS][ILV]C[AGNS]xxH, wherein x indicates any amino acid) of the group 4 hydrogenase was performed using the ProteinFinder program (Ensoltek, Korea) against the non-redundant protein database of the NCBI. Multiple sequence alignment for proteins was performed using the ClustalW program (Thompson, J. D., Higgins, D. G. and Gibson, T. J. (1994) CLUSTAL W: improving the sensitivity of progressive multiple sequence alignment through sequence weighting, position-specific gap penalties and weight matrix choice. Nucleic Acids Res. 22, 4673-4680), and a phylogenetic tree was constructed using Molecular Evolutionary Genetics Analysis (Mega 4.1) software (Tamura, K., Dudley, J., Nei, M. and Kumar, S. (2007) MEGA4: Molecular Evolutionary Genetics Analysis (MEGA) software version 4.0. Mol. Biol. Evol. 24, 1596-1599). The phylogenetic tree of 16S rRNA sequences was made using pre-aligned sequences derived from the Ribosomal database site.

6) Generation of Signature Logos

Logo representations are used to visualize the information content associated with each position of a given motif shared by related sequences. In the graphical representation, the overall height of each position is correlated to the conservation at that position (expressed in bits), whereas the relative sizes of the symbols within a position indicate their relative frequencies. Logo analyses were performed at the Berkeley Structural Genomics Center.

(2) Analysis Result

1) General Features of *T. onnurineus* NA1 Gene

Figure 1A:
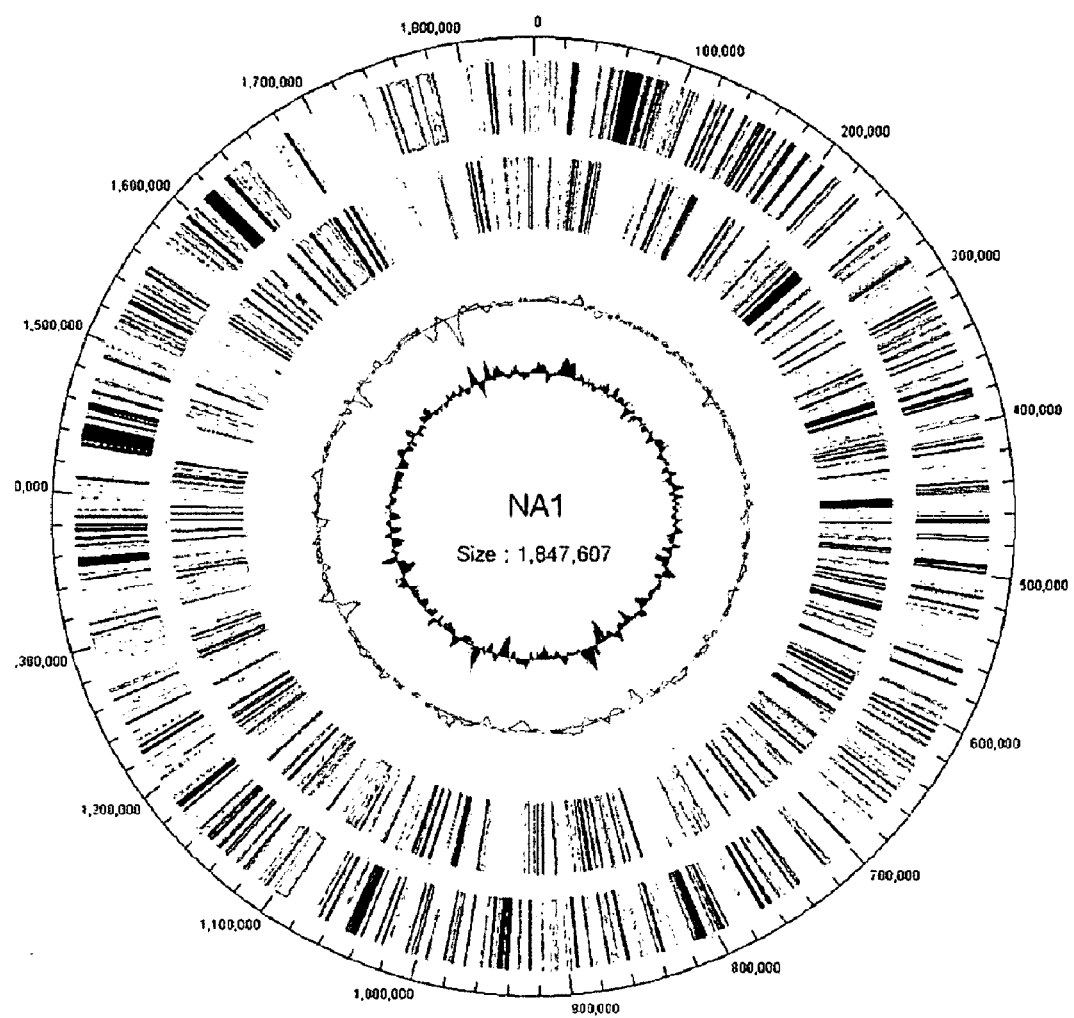

To provide some insight into factors that contributed to the apparent successful competition of *Thermococcus* spp. in hydrothermal vent fields, the genome sequence of *T. onnurineus* NA1 was determined by combining random whole-genome shotgun sequencing with pyrosequencing. As a result, it was revealed that *T. onnurineus* NA1 has a single circular chromosome (1,847,607 bp) without any exochromosomal elements, and a total of 1,976 coding DNA sequences (CDSs) were identified (Table 1 and FIGS. 1A and 1B). Of these, 1,104 CDSs (55.8%) were annotatable by homology and domain searches, but the function of the residual 872 CDSs could not be predicted from the primary structure. When protein similarity was searched on a genome-wide scale, 82.7% of the *T. onnurineus* NA1 proteins showed similarity to those of other members of the *Thermococcales*.

TABLE 1

General features of the *T. onnurineus* NA1 genome and *T. kodakaraensis* KOD1 and *Pyrococcus* strains

| | NA1 | KOD1 | P. abyssi | P. horikoshii | P. furiosus |
|---|---|---|---|---|---|
| Genome size (bp) | 1,847,607 | 2,088,737 | 1,765,118 | 1,738,505 | 1,908,256 |
| Protein-coding regions | 90.1% | 92.1% | 91.1% | 91.2% | 92.5% |
| GC content | 51.0% | 52.0% | 44.7% | 41.9% | 40.8% |
| CDSs[a] | 1976 | 2306 | 1784 | 2064 | 2065 |
| tRNAs | 46 | 46 | 46 | 46 | 46 |
| rRNAs | 5S(×2), 7S,16S,32S | 5S(×2), 7S,16S,32S | 5S(×2), 7S,16S,32S | 5S(×2), 7S,16S,32S | 5S(×2), 7S,16S,32S |

[a]The protein sets for the strains were obtained from the RefSeq collection in NCBI.

2) Hydrogenase Clusters

An extraordinary proportion of hydrogenases and related proteins was detected in the *T. onnurineus* NA1 genome (5.5%), reflecting enhanced conservation or recycling of reducing potentials in association with oxidoreductases, including CO dehydrogenase and formate dehydrogenases.

Hydrogenases can be divided into the following three major groups based on their catalytic metal center: [NiFe]-hydrogenases, [FeFe]-hydsrogenases, and [Fe]-hydrogenases. Based on the unique functional center conserved in each of the hydrogenase groups, it is considered that all hydrogenases in *T. onnurineus* NA1, except for one hydrogenase, belong to [NiFe]-hydrogenases. According to the hydrogenase classification system of Vignais et al., the [NiFe]-hydrogenases in *T. onnurineus* NA1 belong to group 3 (one F420-reducing hydrogenase and two NADP-reducing hydrogenases) or group 4 (four membrane-associated hydrogenases) (Silva, P. J., van den Ban, E. C., Wassink, H., Haaker, H., de Castro, B., Robb, F. T. and Hagen, W. R. (2000) Enzymes of hydrogen metabolism in *Pyrococcus furiosus*. Eur. J. Biochem. 267, 6541-6551). The hydrogenases belonging to group 4 were termed "energy-converting hydrogenases" (Ech) and are widespread among bacteria and archaea.

To understand the molecular basis of hydrogenase metabolism, hydrogenase gene clusters were comparatively analyzed. The hydrogenases were phylogenetically analyzed and, as a result, the group 4 hydrogenases could be divided into two subgroups, 4a and 4b, and a pair of motif patterns common to all the sequences of subgroup 4b could be found.

Figure 2A:
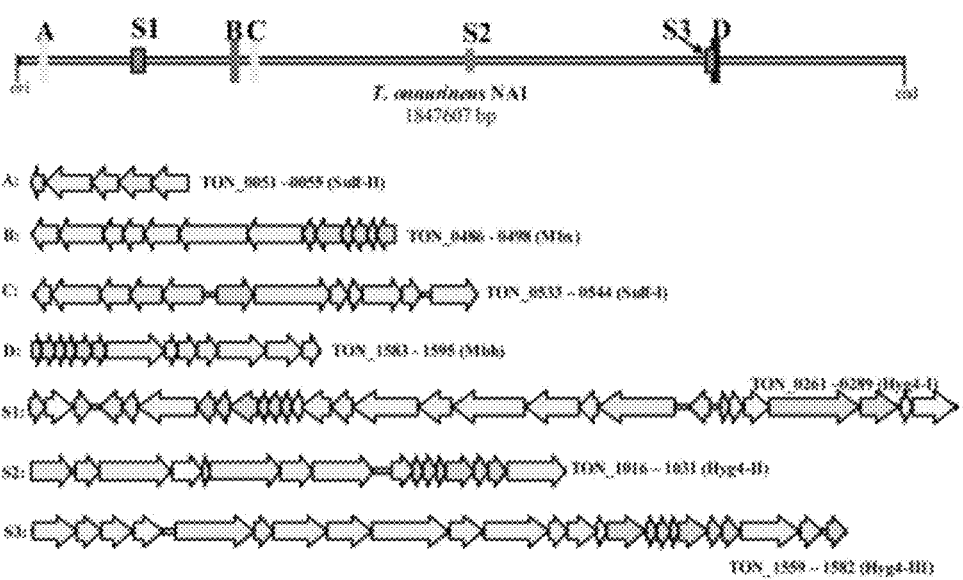
FIG. 2A is a representative map of eight hydrogenase gene clusters in *T. onnurineus* NA1. A, B, C, and D: membrane-bound hydrogenases and cytoplasmic NiFe-hydrogenases. S1, S2, and S3: *T. onnurineus* NA1. Genes were colored according to COG functional categories. TON_0051-0055 represents SEQ ID NOs: 1 to 5; TON_0486-0498 represents SEQ ID NOs: 35 to 47; TON_0533-0544 represents SEQ ID NOs: 48 to 59; TON_1583-1595 represents SEQ ID NOs: 100 to 112; TON_0261-0289 represents SEQ ID NOs: 6 to 34; TON_1016-1031 represents SEQ ID NOs: 60 to 75; and TON_1559-1582 represents SEQ ID NOs: 76 to 99.

As shown in FIG. 2, three additional hydrogenase clusters (FDH1-MFH1-MNH1 (Hyg4-I, S1: TON_0279-0274, MFH1: SEQ ID NO: 2), CODH-MCH-MNH3 (Hyg4-II, S2: TON_1021-1024, MCH: SEQ ID NO: 5) and FDH2-MFH2-MNH2 (Hyg4-III, S3: TON_1565-1571, MFH2: SEQ ID NO: 7)) and Frh (TON_1559-1562, SEQ ID NO: 6) were found in the *T. onnurineus* NA1 genome along with the two membrane-bound hydrogenases (Mbh (TON_1590-1595, SEQ ID NO: 8) and Mbx (TON_0489-0486, SEQ ID NO: 3)) and two cytoplasmic NiFe-hydrogenases (Sulf-I (TON_0533-0544, SEQ ID NO: 4) and Sulf-II (TON_0051-0055, SEQ ID NO: 1) reported in *Pyrococcus* spp. and *T. kodakaraensis* KOD1. Gene cluster analysis of hydrogenases with CDSs from 31 archaeal genomes clearly showed that FDH1-MFH1-MNH1 (Hyg4-I), CODH-MCH-MNH3 (Hyg4-II) and FDH2-MFH2-MNH2 (Hyg4-III) were unique in primary sequence, showing low similarities to hydrogenase 4 components from *P. abyssi* and *R. rubrum* (FIG. 3). Similarly to the additional hydrogenases, the FDH2-MFH2-MNH2 (Hyg4-111) cluster (TON_1559-1582, SEQ ID NOs: 76 to 99) included the α/β/γ subunits of F420 hydrogenase (TON_1559-1561, SEQ ID NOs: 76 to 78) in the genome. The subunits of F420 hydrogenase had unique primary sequences, showing similarities to the coenzyme F420-reducing hydrogenase (YP_001097176) from *Methanococcus maripaludis* (33%) and coenzyme F420-reducing hydrogenase (NP_987940) from *M. maripaludis* S2 (33%) (FIG. 3 and FIG. 5). No F420-hydrogenase homologues from the *Thermococcales* have been reported.

3) Construction of 3-module Gene Clusters

Figure 2B:
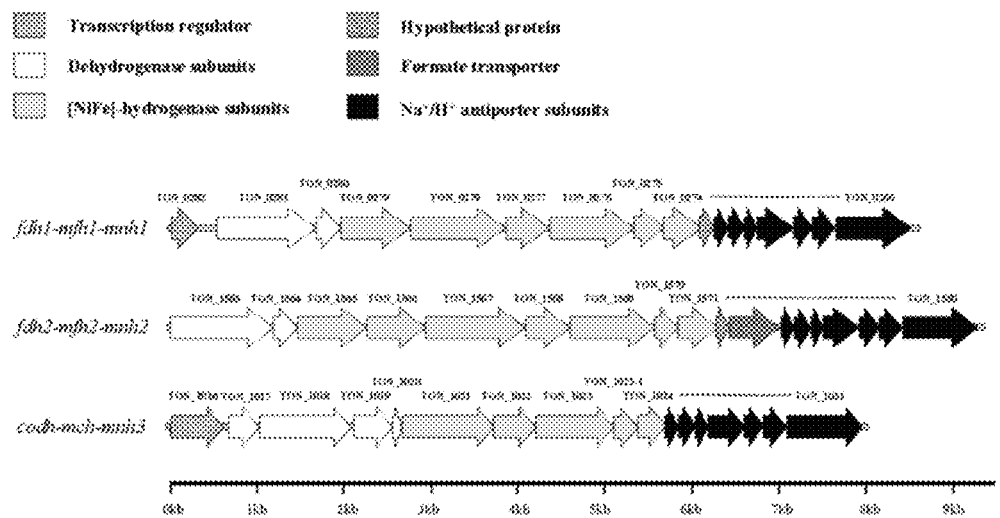
FIG. 2B shows the gene organization of three hydrogenase gene clusters (fdh1-mfh1-mnh1, fdh2-mfh2-mnh2 and codh-mch-mnh) having a 3-module gene cluster on the genome of *T. onnurineus* NA1. Genes belonging to the same subclusters were indicated by the same color.
Figure 3:
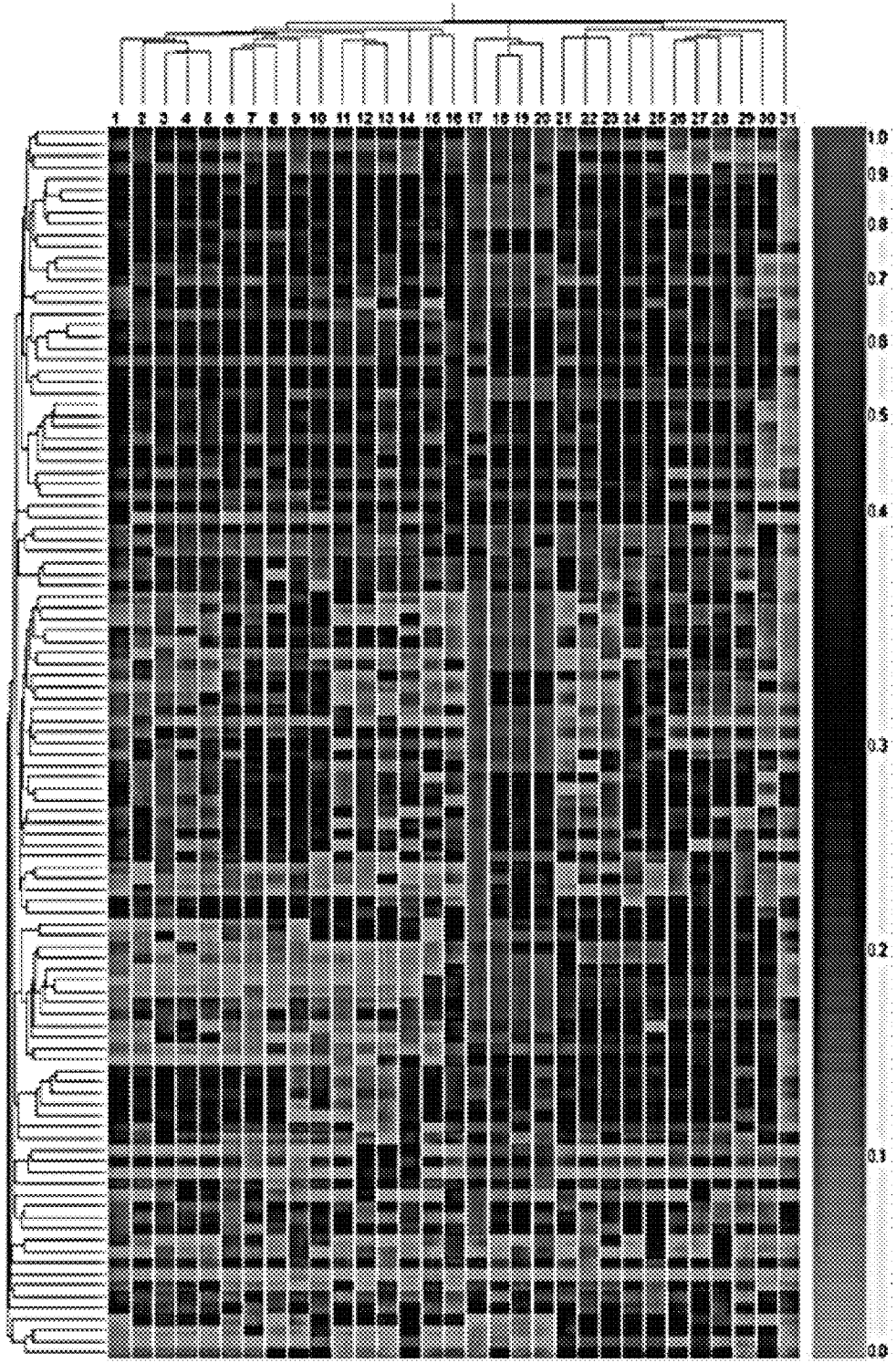
FIG. 3 shows the distribution and conservation patterns of hydrogenase gene clusters in 31 archaeal genomes. The first bracket, the third bracket, the fifth bracket from the bottom encompass CDSs showing low similarities (<25%) to any CDSs from 31 archaeal genomes. The brackets other than the first bracket, the third bracket, the fifth bracket from the bottom indicate CDSs similar to hydrogenase 4 from *P. abyssi*. The 31 archaeal genes are as follows.

It was found that each of the three Ech hydrogenases (MFH1, MFH2, and MCH) belonging the group 4 of [NiFe]-hydrogenases was a portion of large 17- or 18-gene clusters (fdh1-ndh1-mnh1, fdh2-mfh2-mnh2 and codh-mch-mnh3) consisting of TON_266-TON_282, TON_1563-TON_1580 and TON_1016-TON_1031 ORFs (open reading frames) (FIG. 2B). The ORFs in the clusters can be divided into three subclusters. The first part encodes oxidoreductase such as formate dehydrogenases (Fdh1 (SEQ ID NO: 9) or Fdh2 (SEQ ID NO: 11)) or carbon monoxide dehydrogenase (Codh (SEQ ID NO: 10)). The second part encodes multimeric membrane-bound hydrogenases (MFH1, MFH2 or MCH) having 5-7 subunits. The last part encodes cation/proton antiporters such as $Na^+/H^+$ antiporter. Such 3-module gene clusters have not yet been reported.

EXAMPLE 2

Analysis of Gas Composition (1) Analysis Method

Hydrogen gas was measured using a gas chromatograph HP 5890 series II (Hewlett Packard) equipped with an HP-PLOT Molesieve column (Agilent) and a TCD detector. Argon was used as a carrier gas. To quantify hydrogen gas, a gas calibration standard (Supleco) containing 1% (w/w) of each of components (CO, $CO_2$, $H_2$, $CH_4$ and $O_2$) in nitrogen was used (2) Production of Hydrogen Using Various Substances In order to examine whether a number of hydrogenases cause *T. onnurineus* NA1 to efficiently produce hydrogen in various environments, hydrogen production rate was analyzed using various energy sources (Table 2). As a result, the NA1 strain could produce hydrogen using starch, CO and formate even under sulfur-free conditions. Particularly, CO and formate were very good energy sources for efficiently producing hydrogen.

TABLE 2

Comparison of hydrogen production of *T. onnurineus* NA1 under various conditions

| Medium | Hydrogen production (mmol/L) |
| --- | --- |
| M + CO | 30.7 |
| M + Formate | 49.7 |
| M + Starch | 15.6 |

M: modified medium 1

The hydrogen productivity of the NA1 strain in batch culture is similar to those obtained in the continuous culture of *T. kodakaraensis* KOD1 and *Pyrococcus furiosus*. Hyperthermophilic archaea have various advantages in that they show a specific production rate higher than the hydrogen production by mesophilic bacterial fermentation or photobacteria in spite of their low volumetric productivity and produce high-purity hydrogen. The high hydrogen production rates described herein can be much improved through the optimization of culture conditions and treatment processes and metabolic engineering.

EXAMPLE 3

CO-dependent $H_2$ Production by *Thermococcus onnurineus* NA1: Identification of CO-responsive Hydrogenases (1) CODH Gene Cluster and Carboxydotrophic Growth As described above, it was found that *T. onnurineus* NA1 possessed a unique gene cluster (CODH-MCH-MNH3) that was comprised of a putative transcriptional regulator (TON_1016), a CODH accessory protein (CooC, TON_1019), a CODH catalytic subunit (CooS, TON_1018), and an electron transfer protein (CooF, TON_1017), along with a hydrogenase (mch, TON_1021-1024, SEQ ID NO: 5) (FIG. 2B). CooS (TON_1018), a central enzyme in microbial carbon monoxide (CO) metabolism, showed significant similarities with CODHs from CO-oxidizing methanogenic archaea such as CODH (AAM06652) from *Methanosarcina acetivorans* C2A (60%) and CODH (AAM29817) from *Methanosarcina mazei* Go1 (59%) (FIGS. 3 and 4). It seemed a monofunctional CODH (Bonam, D., L. Lehman, G P Roberts, and P. W. Ludden., 1989, Regulation of carbon monoxide dehydrogenase and hydrogenase in *Rhodospirillum rubrum*: effects of CO and oxygen on synthesis and activity. J. Bacteriol. 171:3102-3107; and Wu, M. Q. Ren, A. S. Durkin, S. C. Daugherty, L. M Brinkac, R. J. Dodson, R. Madupu, S. A. Sullivan, J. F. Kolonay, W. C. Nelson, L. J. Tallon, K. M. Jones, L. E. Ulrich, J. M. Gonzalez, I. B. Zhulin, F. T. Robb, and J. A. Eisen. 2005, Life in hot carbon monoxide: the complete genome sequence of *Carboxydothermus hydrogenoformans* Z-2901. PLoS Genet. 1:e65), lacking the acetyl coenzyme A synthesis/cleavage activity of the bifunctional CODH/acetyl coenzyme A synthetase enzyme. According to Fox et al. (Fox, J. D., R. L. Kerby, G. P. Roberts, and P. W. Ludden, 1996, Characterization of the CO-induced, CO-tolerant hydrogenase from *Rhodospirillum rubrum* and the gene encoding the large subunit of the enzyme. J. Bacteriol. 178:1515-1524), the monofunctional CODH/hydrogenase complex from *Rhodospirillum rubrum* participated in CO-driven proton respiration, whereby energy is conserved in the form of a proton gradient generated across the cell membrane. In this sense, to address the issue that the CODH cluster could play a similar role in energy conservation by oxidizing CO, the present inventors tested whether *T. onnurineus* NA1 could utilize CO. As a result, it was found that the strain, indeed, was able to grow better in medium 1 under a CO atmosphere, in both the absence and the presence of sulfur, than in the basal medium (FIGS. 6A and 6B), even though the growth yield was still lower than that in the YPS medium (FIG. 6A). The growth under CO atmosphere was associated with the transcription of the CooS gene, indicating that the gene could be induced by the presence of CO (FIG. 6C). It is noteworthy that the addition of sulfur decreased the transcriptional level of the CooS gene. These results support the hypothesis that *T. onnurineus* NA1 generates energy from CO. Hereinafter, specific test methods and results for verifying the hypothesis will be described.

(2) Test Methods

1) Culture Conditions

*T. onnurineus* NA1 was anaerobically cultured in a yeast extract-peptone-sulfur (YPS) medium at 80° C. To examine the growth characteristics of a mutant strain, modified medium 1 supplemented with 30.0 g/L of NaCl was used as a basal medium (Uffen, R. L., 1976, Anaerobic growth of a *Rhodopseudomonas* species in the dark with carbon monoxide as sole carbon and energy substrate. Proc. Natl. Acad. Sci. USA 73:3298-3302). The medium was autoclaved, and then 1.0 ml/L of vitamin solution (Balch, W. E., G. E. Fox, L. J. Magrum, C. R. Woese, and R. S. Wolfe. 1979. Methanogens: reevaluation of a unique biological group. Microbiol. Rev. 43:260-296) and 0.5 g/L of yeast extract were added to modified medium 1 in an aerobic chamber. The pH was adjusted to 8.0 by adding 1N NaOH to the basal medium. 30 ml of the prepared medium was dispensed into 150-ml serum bottles, and the gas phase (120 ml) was changed to 100% CO ($10^5$ Pa). All the cultures for physiological tests were carried out at 80° C. in anaerobic conditions for 24 hours, and the tests were carried out in duplicate.

2) RNA Extraction and Microarray Design

Cultures were centrifuged at 4° C. at 3,500×g for 10 min, and the total RNA was extracted from the cultures with TRIZOL reagent according to the manufacturer's protocol (Invitrogen, Carlsbad, Calif.). The total RNA samples were quantitatively and qualitatively analyzed by a NanoDrop spectrophotometer (ND-1000, Thermo Scientific) and electrophoresis. The micrtoarray used in this experiment was a Roche NimbleGen microarray. Briefly, a total of 31,994 unique 60-mer oligonucleotides were designed and synthesized in situ using photo-deprotection chemistry. Each unique oligonucleotide was repeated twice on the array (a total of 72,000 features).

3) cDNA Synthesis and Hybridization Conditions

A microarray test was carried out according to the manufacturer's protocol. Each total RNA sample (5 μg) was labeled with Cy5-dCTP (Amersharm, Piscataway, N.J.) by a reverse transcription reaction using reverse transcriptase, SuperScript II (Invitrogen, Carlsbad, Calif.). Then, the labeled cDNA mixture was concentrated using ethanol precipitation. 30 μl of the concentrated Cy5-labeled cDNAs were suspended in a hybridization solution (GenoCheck, Korea). The labeled cDNAs were located on the microarray, and then covered by a MAUI Mixer X4 hybridization chamber (BioMicro Systems, Salt Lake City, Utah). The slides were hybridized using MAUI 12-bay systems (BioMicro Systems, Salt Lake City, Utah) at 42° C. for 12 hours. The hybridized slides were washed at room temperature in 2×SSC, 0.1% SDS for 2 min, 1×SSC for 3 min, and then 0.2×SSC for 2 min. The slides were centrifuged at 1,000×g for 20 sec, followed by drying.

4) Slide Scanning, Normalization, and Data Analysis

Arrays were scanned using a GenePix 4000B scanner (Molecular Devices Corporation, Union City, Calif.), and the data were extracted using NimbleScan 2.4 software. Array normalization was performed using a median polish and quantile normalization method (Amaratunga, D., and J. Cabrera. 2001. Statistical analysis of viral microchip data. J. Am. Stat. Assoc. 96:1161-1170). Normalized expression values for the individual probes were used to obtain expression values for a given ORF using the RMA (robust multi-array average) method previously described by Irizarry et al. (Karl, D. M. 1995. The microbiology of deep-sea hydrothermal vents. CRC Press, Boca Raton, Fla.). Finally, n-fold change ratios (R) were calculated using the RMA-processed expression values (RMA calls) obtained for a particular gene in a sample. Data analysis was performed using GeneSpring GX 7.3.1 (Agilent Technologies, CA). Fold change filters included the requirement that the genes be present in at least 200% of controls for up-regulated genes and lower than 50% of controls for down-regulated genes. The data were clustered into groups of genes that behave similarly in experiments using GeneSpring GX 7.3.1 (Agilent technologies, CA). An algorithm based on the Euclidean distance and average linkage was used to separate the gene of similar patterns.

5) Quantitative RT-PCR

Gene specific primers were designed from the genome sequence of *T. onnurineus* NA1 (Genbank accession number CP000855). The primer sequences are shown in Table 3 below.

cDNAs were synthesized from 350 ng of total RNA using reverse transcriptase, SuperScript II (Invitrogen, Carlsbad, Calif.), according to the manufacturer's protocol. PCR reactions were performed with rTaq (Takara) DNA polymerase using a T1 thermocycler (Biometra). The reactions were performed in 50 μl of a mixture containing first-strand reaction cDNA, 10 pmol primers, 250 µM dNTPs and manufacturer's buffer. Also, the PCR amplification reactions were performed in the following conditions: denaturation of 2 min for 94° C.; and then 25 cycles of denaturation (30 sec at 94° C.), annealing (30 sec at 56° C.) and extension (1 min at 72° C.). The PCR products were analyzed by 0.8% agarose gel electrophoresis. The expression level was measured using Gel Pro32.EXE v4.6 (Media Cybernetics, Inc.). A Chaperonin-encoding gene, named "cha", was used as a control to normalize expression levels.

TABLE 3

Oligonucleotides used in this Example

| Gene name | Sense (5'→3') | Anti-sense (5'→3') |
|---|---|---|
| Primers used in RT-PCR | | |
| mbh | Cacgacataggctacgacacgg (SEQ ID NO: 27) | Ctggcttaactcctaggtcagg (SEQ ID NO: 28) |
| mbx | Gcgattcggtatgataccggac (SEQ ID NO: 29) | Ccatccttcgccgaagagctcg (SEQ ID NO: 30) |
| frh | Gtaagctcgacgagtacgacgtg (SEQ ID NO: 31) | Gcaccacaacctatgcagaggcc (SEQ ID NO: 32) |
| sulfI | Gcagtacgaggaagtcgagggg (SEQ ID NO: 33) | Gagggcctcgtcgataaggtcg (SEQ ID NO: 34) |
| mch | Ctaccggacgattggccagaagg (SEQ ID NO: 35) | Ccttatatactgtgctctctccg (SEQ ID NO: 36) |
| mfh1 | Gcgaccggtacggcaaccttcg (SEQ ID NO: 37) | Cttgtcagtcatgacgtagtgg (SEQ ID NO: 38) |
| mfh2 | Gacccgaggttcacctcgatagc (SEQ ID NO: 39) | Gcagacctggtcgtaggttagcc (SEQ ID NO: 40) |
| Primers used in gene disruption | | |
| Flk-mch | cgttgtctttgcccttggggcagggatatatc (SEQ ID NO: 41) | ggcaattgcttggactgccgaaaagccaatggc (SEQ ID NO: 42) |
| Flk-mfh1 | gaagaaatcgcagagggcgcctatgactatcag (SEQ ID NO: 43) | gctcctcgcttactcaagcgttggacaaatgg (SEQ ID NO: 44) |
| Flk-mfh2 | ggactgctcttcctgtcgacgggctcaatattc (SEQ ID NO: 45) | ggacgcacttaaagtcggcgtagcccttgcc (SEQ ID NO: 46) |
| Ivs-mch | aatttaccaccccaccactcccaaaatccaac (SEQ ID NO: 47) | aatggggaggctgaaactactgggcaaggc (SEQ ID NO: 48) |
| Ivs-mfh1 | tggcccaggcgatttccttcaccgacagg (SEQ ID NO: 49) | aattcaccaccccaccagcgctattatcagg (SEQ ID NO: 50) |
| Ivs_mfh2 | gagcaccacctcaccatcccagggaagctatc (SEQ ID NO: 51) | gatggccgtgacgctgaagtaccccttcgtga (SEQ ID NO: 52) |
| Primers used in identification of gene disruption | | |
| $P_{gdh}$-hmg$_{Pfu}$ | gaacggtagttttcgacaaaagacg (SEQ ID NO: 53) | gctcaccagccaaaaccgcaccagc (SEQ ID NO: 54) |
| mch$_{TNA1}$ | gcaatgtaccacatattcaactgcgatac (SEQ ID NO: 55) | ccgataccgagtttgaatggaggaatctc (SEQ ID NO: 56) |
| mfh1$_{TNA1}$ | tcaggccaccccttgcccttctgt (SEQ ID NO: 57) | atggagtgcagcgtgtgtgcgggtg (SEQ ID NO: 58) |
| mfh2$_{TNA1}$ | atgtctgaagttatcaagtttaacg (SEQ ID NO: 59) | tgaggcctttatggagagcttgttg (SEQ ID NO: 60) |

6) Targeted Gene Disruption

To analyze the function of hydrogenases in vivo of *T. onnurineus*, insertional inactivation mutants of the large subunit of mch or mfh2 hydrogenase were constructed using a gene disruption system used for the hyperthermophilic archaeon *T. kodakaraensis* KOD1 (Sapra, R., K. Bagramyan, and M. W. W. Adams, 2003, A simple energy-conserving system: Proton reduction coupled to proton translocation. Proc. Natl. Acad. Sci. USA 100:7545-7550). Specifically, DNA fragments comprising the flanking region of the large subunits ((TON_023 and TON_1569) of each of mch and mfh2 hydrogenases were amplified from the genomic DNA of *T. onnurineus* NA1 using primer sets (Table 3) for Flk-mch or Flk-mfh2. Each of the amplified fragments was ligated into pUC118 digested with HincII. Next, a template (Flk-mch_pUC118 or Flk-mfh2_pUC118 recombinant plasmid) was subjected to inverse PCR using a set of primers (Ivs-mch or Ivs-mfh2) (Table 3), and then ligated into a $P_{gdh}$-hmg$_{Pfu}$ cassette (Sapra, R., K. Bagramyan, and M. W. W. Adams. 2003. A simple energy-conserving system: Proton reduction coupled to proton translocation. Proc. Natl. Acad. Sci. USA 100:7545-7550). The ligated product was transformed into *Escherichia coli* DH5α cells. Recombinant plasmids (mch::$P_{gdh}$-hmg$_{Pfu}$ and mfh2 $P_{gdh}$-hmg$_{Pfu}$) were prepared with the plasmid mini kit (Qiagen, Hilden, Germany). Finally, the plasmids were transformed into *T. onnurineus* NA1 using a slight modification of the method of Sato et al. (Sato, T., T. Fukui, H. Atomi, and T. Imanaka. 2003. Targeted gene disruption by homologous recombination in the hyperthermophilic archaeon *Thermococcus kodakaraensis* KOD1. J. Bacteriol. 185:210-220., Sato, T., T. Fukui, H. Atomi, and T. Imanaka. 2005. Improved and versatile transformation system allowing multiple genetic manipulations of the hyperthermophilic archaeon *Thermococcus kodakaraensis*. Appl. Environ. Microbiol. 71:3889-3899). The transformants were screened in ASW-YT-S medium in the presence of 10 μM simvastatin (Matsumi, R., K. Manabe, T. Fukui, H. Atomi, and T. Imanaka. 2007. Disruption of a sugar transporter gene cluster in a hyperthermophilic archaeon using a host-marker system based on antibiotic resistance. J. Bacteriol. 189: 2683-2691), and the candidate groups thought that the target gene was deleted therefrom could be confirmed by examining whether the $P_{gdh}$-hmg$_{Pfu}$ cassette was present in the target region.

7) Kinetics on Growth and Hydrogen Production

Growth was observed directly by the eye. Samples were diluted in sterile water containing sea salt (30.0 g/L), formalin (2.5%) and 4'-6'-diamidino-2-phenylindole (0.01%) (Sato, T., T. Fukui, H. Atomi, and T. Imanaka. 2005 Improved and versatile transformation system allowing multiple genetic manipulations of the hyperthermophilic archaeon *Thermococcus kodakaraensis*. Appl. Environ. Microbiol. 71:3889-3899). The diluted samples were filtered through a black polycarbonate filter (pore size: 0.2 μm; Whatman), and then analyzed by an optical phase contrast microscope (Zeiss Axioplan). Hydrogen gas was measured using a gas chromatograph HP 5890 series II (Hewlett Packard) equipped with a HP-PLOT Molesieve column (Agilent) and a TCD detector. Argon was used as a gas carrier. The oven temperature was 40° C. 10 μl of a gas sample for analysis was taken with a gas-tight syringe through a butyl rubber plug. The measurement of the detected hydrogen gas was calculated by comparing the peak area with a calibration curve obtained by regression analysis using a standard gas containing 40% hydrogen in nitrogen.

(3) Test Results

1) In Silico Analysis of *T. onnurineus* NA1 Hydrogenase

The previous genomic analysis of *T. onnurineus* NA1 showed the presence of eight hydrogenase gene clusters (Porter, K. G. and Y. S. Feig. 1980. The use of DAPI for identifying and counting microflora. Limnol. Oceanogr. 25:943-948), which include five membrane-bound [NiFe]-hydrogenases (Mbh, TON_1583-1595; Mbx, TON_0486-0498; Mfh1, TON_0273-0278; Mfh2, TON_1566-1573; and Mch, TON_1021-1024), and three cytoplasmic [NiFe]-hydrogenases (Fm, TON_1559-1562; Sulf I, TON_0533-0544; and Sulf II, TON_0051-0055). Through the comparative analysis of hydrogenase gene clusters and the Thermococcales strains whose genome sequencing has been completed, it could be seen that clusters homology to Mfh1, Mfh2 and Mch clusters were very rare and were found in *Thermococcales* strains whose genome sequences have recently been determined, such as *T. barophilus* MP (Mfh1 and Mch homologues), *Thermococcus* sp. AM4 (Mfh1 and Mch homologues) (Unfinished sequence, GenBank accession number ABXN00000000), and *T. gammatolerans* (Mfh1 and Mfh2 homologues) (GenBank accession number CP001398). The sequencing of fdh1-mfh1-mnh1 (termed "Hyg4-I" in the paper of Lee, H. S., S. G. Kang, S. S. Bae, J. K. Lim, Y. Cho, Y. J. Kim, J. H. Jeon, S.-S. Cha, K. K. Kwon, H.-T. Kim, C.-J. Park, H.-W. Lee, S. I. Kim, J. Chun, R. R. Colwell, S.-J. Kim, and J.-H. Lee. 2008. The complete genome sequence of *Thermococcus onnurineus* NA1 reveals a mixed heterotrophic and carboxydotrophic metabolism. J. Bacteriol. 190:7491-7499), fdh2-mfh2-mnh2 (termed "Hyg4-III") and codh-mch-mnh3 (termed "Hyg4-II") clusters in *T. onnurineus* NA1 showed that each of the clusters included oxidoreductases such as formate dehydrogenase (FDH) and CO dehydrogenase (Codh). Particularly, carboxydotrophic metabolism resulting from growth in a CO-containing atmosphere suggests the functional role of Codh-Mch-Mnh3 that provides energy in hydrogen production pathways by oxidizing CO.

2) Expression of Hydrogenase Genes under CO-driven Growth Conditions

A test for determining whether *T. onnurineus* NA1 can produce hydrogen while growing in a CO-containing atmosphere was carried out. As shown in FIGS. 7A and 7B, in the YPS medium, hydrogen production could not be detected, but in medium 1 supplemented with CO, the total hydrogen gas and the cell number increased with an increase in culture time.

In order to examine which of hydrogenases are involved in hydrogen production during carboxydotrophic growth, the expression levels of hydrogenase genes in a CO-containing growth condition or a complex medium (YPS) were analyzed. As shown in Tables 4 and 5 and FIG. 8A, the expression levels of some ORFs (10 of 16 ORFs) in the codh-mch-mnh3 cluster were up-regulated at least two-fold in the CO-containing growth condition compared to the YPS. In addition, the expression levels of several ORFs (TON_1563, and TON_1569-1571) in the fdh2-mfh2-mnh2 cluster were also up-regulated in a CO-containing growth condition containing 1 g of yeast extract. The expression levels of ORFs in the codh-mch-mnh3 cluster varied depending on the amount of yeast extract, suggesting that the yeast extract has a correlation with the inhibition or activation of catabolism in CO-driven metabolism (Tables 4 and 5). On the other hand, the expression of other hydrogenase gene clusters did not greatly change, whereas the expression of the genes (20 genes of 29 ORFs) in the fdh1-mfh1-mnh1 cluster was down-regulated. Quantitative RT-PCR data for the large subunit of each of hydrogenases were also consistent with the microarray data. The expression of the large subunits (TON_1023 and TON_1569) of mch and mfh2 hydrogenases was increased at least two-fold (FIG. 8B), whereas the expression of the large subunit (TON_0276) of mfh1 hydrogenase was inhibited and the expression of other large subunits (mbh, mbx, frh, and sulf1) was maintained constant in both conditions. Such results suggest that the codh-mch-mnh3 or fdh2-mfh2-mnh2 clusters can be derived by CO and involved in hydrogen production processes associated with carboxydotrophic metabolism.

TABLE 4

Expression levels of ORFs of each of hydrogenase gene clusters in CO-containing growth condition compared to those in YPS medium

| Gene cluster and ORFs | Annotation | M + CO + 0.5 g YE/ YPS | M + CO + 1 g YE/ YPS | M + CO + 3 g YE/YPS |
|---|---|---|---|---|
| | sulfII hydrogenase cluster | | | |
| TON_0051 | hypothetical protein | 1.273306 | 3.1454 | 2.569546 |
| TON_0052 | hydrogenase subunit alpha | 1.085002 | 0.652365 | 0.550585 |
| TON_0053 | Sulfhydrogenase II, delta chain | 0.896129 | 1.898148 | 1.337585 |
| TON_0054 | hydrogenase subunit gamma | 0.606088 | 0.517724 | 0.630549 |
| TON_0055 | sulfhydrogenase II, beta chain | 0.84527 | 1.44889 | 1.452254 |
| | fdh1-mfh1-mnh1 cluster | | | |
| TON_0261 | hypA hydrogenase expression/formation protein | 0.658409 | 0.78969 | 0.746964 |
| TON_0262 | ATPase involved in chromosome partitioning, ParA/MinD family, Mrp homolo | 0.640277 | 0.776389 | 0.619674 |
| TON_0263 | hydrogenase maturation protease HycI | 0.775719 | 1.531337 | 1.090123 |
| TON_0264 | molybdopterin-guanine dinucleotide biosynthesis protein A | 0.538102 | 0.957335 | 0.826924 |
| TON_0265 | Nucleotidyltransferase, putative | 0.421398 | 0.554433 | 0.503557 |
| TON_0266 | component F or formate hydrogen lyase | 0.38336 | 0.338185 | 0.333459 |
| TON_0267 | Putative integral membrane protein, DUF68 family | 0.296945 | 1.215972 | 0.838087 |
| TON_0268 | Putative integral membrane protein, DUF67 family | 0.648077 | 0.424896 | 0.386235 |
| TON_0269 | Multisubunit Na+/H+ antiporter, putative MnhB subunit | 0.591411 | 0.571996 | 0.600235 |
| TON_0270 | hypothetical protein | 0.827927 | 0.85379 | 0.581906 |
| TON_0271 | Na$^+$/H$^+$ antiporter subunit | 0.410417 | 0.328062 | 0.51901 |
| TON_0272 | Na$^+$/H$^+$ antiporter MnhF subunit, putative | 0.194663 | 0.411647 | 0.331549 |
| TON_0273 | hypothetical protein | 0.269222 | 0.652722 | 0.482705 |
| TON_0274 | component I or formate hydrogen lyase | 0.385799 | 0.627629 | 0.614487 |
| TON_0275 | formate hydrogen lyase subunit 6 | 0.313283 | 0.621333 | 0.511819 |
| TON_0276 | component G or formate hydrogen lyase | 0.275138 | 0.724228 | 0.692331 |
| TON_0277 | component C or formate hydrogen lyase | 0.460646 | 0.357836 | 0.387126 |
| TON_0278 | component B or formate hydrogen lyase | 0.720779 | 0.623875 | 0.510273 |
| TON_0279 | NADH ubiquinone oxidoreductase | 0.80929 | 0.515429 | 0.54289 |
| TON_0280 | oxidoreductase iron-sulfur protein | 0.3913 | 0.690322 | 0.647104 |
| TON_0281 | fdhA formate dehydrogenase, alpha subunit | 0.584576 | 0.446401 | 0.44946 |
| TON_0282 | putative transcriptional regulator | 1.340444 | 1.195043 | 0.883294 |
| TON_0283 | hypC hydrogenase expression/formation protein | 1.007318 | 1.853137 | 2.021914 |
| TON_0284 | 367aa long hypothetical hydrogenase expression/formation protein hypD | 1.036497 | 1.385466 | 1.182663 |
| TON_0285 | hypD hydrogenase expression/formation protein | 0.904687 | 1.066448 | 0.758981 |
| TON_0286 | hydrogenase maturation protein HypF | 0.685606 | 0.778307 | 0.719973 |
| TON_0287 | hydrogenase expression/formation protein HypE | 0.851301 | 1.399569 | 1.257059 |
| TON_0288 | hypothetical protein | 1.004008 | 1.964442 | 2.27641 |
| TON_0289 | cysteine desulfurase | 0.666768 | 1.534991 | 1.148004 |
| | mbx hydrogenase cluster | | | |
| TON_0486 | 4Fe—4S cluster-binding subunit | 0.821271 | 0.718277 | 0.504388 |
| TON_0487 | nuoD NADH dehydrogenase I, subunit D | 0.606823 | 0.730138 | 0.517528 |
| TON_0488 | NADH dehydrogenase subunit | 0.703506 | 0.618352 | 0.49939 |
| TON_0489 | nuoB NADH dehydrogenase I, subunit B | 0.797159 | 0.618863 | 0.547462 |
| TON_0490 | NADH dehydrogenase subunit | 0.372425 | 0.469467 | 0.278163 |
| TON_0491 | 617aa long hypothetical protein | 0.459201 | 0.532164 | 0.388201 |
| TON_0492 | MbxH subunit | 0.862715 | 0.484349 | 0.423606 |
| TON_0493 | Multisubunit Na+/H$^+$ antiporter, putative | 0.70216 | 1.591408 | 1.138149 |
| TON_0494 | Multisubunit Na+/H$^+$ antiporter, putative MnhB subunit | 0.765286 | 0.716126 | 1.711304 |
| TON_0495 | MbxD subunit | 0.658086 | 0.817339 | 0.749402 |
| TON_0496 | MbxC subunit | 0.609819 | 1.200655 | 0.995067 |
| TON_0497 | MbxB subunit | 0.860304 | 0.889029 | 0.810902 |
| TON_0498 | Multisubunit Na$^+$/H$^+$ antiporter, putative | 0.675578 | 0.564247 | 0.483617 |
| | sulfI hydrogenase cluster | | | |
| TON_0533 | hydrogenase-specific maturation endopeptidase | 0.977803 | 0.516234 | 0.73084 |
| TON_0534 | cytosolic NiFe-hydrogenase, alpha subunit | 1.283309 | 1.334781 | 1.071667 |
| TON_0535 | cytosolic NiFe-hydrogenase, delta subunit | 0.652099 | 1.080516 | 0.800955 |
| TON_0536 | hydrogenase (gamma subunit) | 1.100959 | 1.192121 | 0.759086 |
| TON_0537 | Sulfhydrogenase beta subunit | 1.025726 | 1.458113 | 1.160718 |
| TON_0538 | probable formate transporter | 0.989789 | 1.113613 | 0.960108 |
| TON_0539 | probable formate dehydrogenase, alpha subunit | 1.158997 | 1.791123 | 1.314525 |
| TON_0540 | oxidoreductase iron-sulfur protein | 0.987581 | 1.525167 | 0.82483 |
| TON_0541 | 4Fe—4S cluster-binding protein | 1.112648 | 1.320761 | 0.855465 |
| TON_0542 | glutamate synthase beta chain-related oxidoreductase | 0.842213 | 1.602828 | 0.936949 |
| TON_0543 | 4Fe—4S cluster-binding protein | 0.9185 | 1.257283 | 1.019564 |
| TON_0544 | alcohol dehydrogenase | 0.87473 | 0.419323 | 0.605934 |
| | codh-mch-mnh3 cluster | | | |
| TON_1016 | putative transcriptional regulator, ModE family | 1.187798 | 0.634394 | 0.731218 |
| TON_1017 | 4Fe—4S ferredoxin, iron-sulfur binding domain | 1.713085 | 4.46107 | 3.621394 |
| TON_1018 | carbon-monoxide dehydrogenase, catalytic subunit | 1.474238 | 2.204944 | 1.785437 |

TABLE 4-continued

Expression levels of ORFs of each of hydrogenase gene clusters in CO-containing growth condition compared to those in YPS medium

| Gene cluster and ORFs | Annotation | M + CO + 0.5 g YE/ YPS | M + CO + 1 g YE/ YPS | M + CO + 3 g YE/YPS |
|---|---|---|---|---|
| TON_1019 | putative ATP-binding protein | 0.824732 | 2.016924 | 0.974466 |
| TON_1020 | hypothetical protein | 3.375546 | 9.366047 | 5.425704 |
| TON_1021 | component B or format hydrogen lyase | 1.112538 | 1.711122 | 1.250867 |
| TON_1022 | respiratory-chain NADH dehydrogenase, subunit 1 | 0.877363 | 1.428883 | 0.57715 |
| TON_1023 | component G or format hydrogen lyase | 1.927395 | 6.118015 | 4.270288 |
| TON_1024 | NADH dehydrogenase (ubiquinone), 20 kDa subunit | 1.816315 | 3.578841 | 2.009973 |
| TON_1025 | $Na^+/H^+$ antiporter MnhF subunit, putative | 2.443938 | 3.389037 | 1.333503 |
| TON_1026 | $Na^+/H^+$ antiporter subunit | 1.337719 | 0.605839 | 0.623499 |
| TON_1027 | hypothetical protein | 0.991048 | 1.43866 | 0.778446 |
| TON_1028 | Multisubunit $Na^+/H^+$ antiporter, MnhB subunit | 1.019583 | 1.203407 | 0.836452 |
| TON_1029 | Putative integral membrane protein, DUF67 family | 2.648286 | 2.171138 | 1.123898 |
| TON_1030 | Putative integral membrane protein, DUF68 family | 3.779798 | 4.956998 | 1.592196 |
| TON_1031 | component F or formate hydrogen lyase | 1.030507 | 2.778588 | 1.982091 |
| frh ($F_{420}$ reducing hydrogenase) hydrogenase cluster | | | | |
| TON_1559 | coenzyme F420 hydrogenase alpha subunit | 0.695408 | 0.64447 | 0.726535 |
| TON_1560 | Coenzyme F420 hydrogenase gamma subunit | 0.56769 | 0.715513 | 0.635236 |
| TON_1561 | 4Fe—4S ferredoxin, iron-sulfur binding Nitrite/sulfite reductase | 0.824149 | 0.834127 | 0.807754 |
| TON_1562 | Formate dehydrogenase, subunit FdhD | 0.908701 | 1.54082 | 1.468288 |
| Fdh2-mfh2-mnh2 cluster | | | | |
| TON_1563 | Probable formate dehydrogenase, alpha subunit | 1.008259 | 3.037865 | 3.330042 |
| TON_1564 | 4Fe—4S cluster-binding protein | 1.178705 | 1.221574 | 1.445098 |
| TON_1565 | NADH ubiquinone oxidoreductase | 0.811937 | 1.787894 | 2.088693 |
| TON_1566 | NADH dehydrogenase (quinone) | 1.011779 | 0.736029 | 0.787627 |
| TON_1567 | component B or formate hydrogen lyase | 1.091992 | 1.057076 | 1.184573 |
| TON_1568 | component C or formate hydrogen lyase | 1.471267 | 1.365925 | 1.382301 |
| TON_1569 | component G or formate hydrogen lyase | 1.204795 | 2.281342 | 1.780033 |
| TON_1570 | formate hydrogen lyase subunit 6 | 1.257649 | 2.427962 | 1.99559 |
| TON_1571 | component I or formate hydrogen lyase | 1.030626 | 2.15871 | 1.806722 |
| TON_1572 | hypothetical protein | 0.844948 | 0.504955 | 0.692272 |
| TON_1573 | probable formate transporter | 1.451628 | 1.459657 | 1.158131 |
| TON_1574 | $Na^+/H^+$ antiporter MnhF subunit, putative | 1.53015 | 1.602287 | 1.244315 |
| TON_1575 | $Na^+/H^+$ antiporter subunit | 0.752784 | 0.646406 | 0.578467 |
| TON_1576 | hypothetical protein | 1.168966 | 0.564328 | 0.60819 |
| TON_1577 | Multisubunit $Na^+/H^+$ antiporter, putative MnhB subunit | 0.726511 | 0.655031 | 0.556386 |
| TON_1578 | Putative integral membrane protein, DUF67 family | 0.989286 | 1.061599 | 0.900044 |
| TON_1579 | Putative integral membrane protein, DUF68 family | 0.903028 | 0.812346 | 0.816319 |
| TON_1580 | component F or formate hydrogen lyase | 1.015786 | 0.756283 | 0.529199 |
| TON_1581 | molybdopterin-guanine dinucleotide biosynthesis protein A | 0.61468 | 1.708744 | 1.243367 |
| TON_1582 | hypothetical protein | 0.753301 | 0.998059 | 0.952751 |
| mbh hydrogenase cluster | | | | |
| TON_1583 | MbhB subunit | 1.038442 | 0.519366 | 0.533773 |
| TON_1584 | MbhC subunit | 0.947559 | 0.514932 | 0.5099 |
| TON_1585 | MbhD subunit | 0.774604 | 1.015909 | 0.670497 |
| TON_1586 | MbhE subunit | 1.101069 | 0.811262 | 0.659266 |
| TON_1587 | MbhF subunit | 1.129566 | 0.811366 | 0.872572 |
| TON_1588 | MbhG subunit | 1.027148 | 0.563686 | 0.510924 |
| TON_1589 | MbhH subunit | 1.362042 | 0.948034 | 0.71984 |
| TON_1590 | MbhI subunit | 1.334732 | 1.227655 | 0.904813 |
| TON_1591 | NiFe-hydrogenase small subunit | 1.627315 | 1.158127 | 0.856929 |
| TON_1592 | NiFe-hydrogenase large subunit 1 | 0.940698 | 1.573248 | 0.956935 |
| TON_1593 | NiFe-hydrogenase large subunit 2 | 1.609483 | 2.286207 | 1.354849 |
| TON_1594 | MbhM subunit | 0.982323 | 0.742211 | 0.458623 |
| TON_1595 | 4Fe—4S cluster-binding subunit | 1.589684 | 1.280298 | 0.491906 |

M, medium 1;
CO, carbon monoxide;
YE, yeast extract.

TABLE 5

Hierarchical clustering of 112 ORFs including hydrogenase clusters from *T. onnurineus* NA1

| Gene cluster | ORFs | Annotation | M + CO + 0.5 g YE/YPS | M + CO + 1 g YE/YPS | M + CO + 3 g YE/YPS |
|---|---|---|---|---|---|
| fdh1-mfh1-mnh1 | TON_0272 | $Na^+/H^+$ antiporter MnhF subunit, putative | 0.194663 | 0.411647 | 0.331549 |
| fdh1-mfh1-mnh1 | TON_0267 | Putative integral membrane protein, DUF68 family | 0.296945 | 1.215972 | 0.838087 |
| fdh1-mfh1-mnh1 | TON_0273 | hypothetical protein | 0.269222 | 0.652722 | 0.482705 |

TABLE 5-continued

Hierarchical clustering of 112 ORFs including hydrogenase clusters from *T. onnurineus* NA1

| Gene cluster | ORFs | Annotation | M + CO + 0.5 g YE/YPS | M + CO + 1 g YE/YPS | M + CO + 3 g YE/YPS |
|---|---|---|---|---|---|
| fdh1-mfh1-mnh1 | TON_0275 | formate hydrogen lyase subunit 6 | 0.313283 | 0.621333 | 0.511819 |
| fdh1-mfh1-mnh1 | TON_0276 | component G or formate hydrogen lyase | 0.275138 | 0.724228 | 0.692331 |
| fdh1-mfh1-mnh1 | TON_0274 | component I or formate hydrogen lyase | 0.385799 | 0.627629 | 0.614487 |
| fdh1-mfh1-mnh1 | TON_0280 | oxidoreductase iron-sulfur protein | 0.3913 | 0.690322 | 0.647104 |
| fdh1-mfh1-mnh1 | TON_0271 | $Na^+/H^+$ antiporter subunit | 0.410417 | 0.328062 | 0.51901 |
| fdh1-mfh1-mnh1 | TON_0266 | component F or formate hydrogen lyase | 0.38336 | 0.338185 | 0.333459 |
| fdh1-mfh1-mnh1 | TON_0277 | component C or formate hydrogen lyase | 0.460646 | 0.357836 | 0.387126 |
| fdh1-mfh1-mnh1 | TON_0268 | Putative integral membrane protein, DUF67 family | 0.648077 | 0.424896 | 0.386235 |
| fdh1-mfh1-mnh1 | TON_0281 | fdhA formate dehydrogenase, alpha subunit | 0.584576 | 0.446401 | 0.44946 |
| fdh1-mfh1-mnh1 | TON_0265 | Nucleotidyltransferase, putative | 0.421398 | 0.554433 | 0.503557 |
| mbx | TON_0491 | 617aa long hypothetical protein | 0.459201 | 0.532164 | 0.388201 |
| mbx | TON_0490 | NADH dehydrogenase subunit | 0.372425 | 0.469467 | 0.278163 |
| fdh1-mfh1-mnh1 | TON_0261 | hypA hydrogenase expression/formation protein | 0.658409 | 0.78969 | 0.746964 |
| mbx | TON_0495 | MbxD subunit | 0.658086 | 0.817339 | 0.749402 |
| fdh1-mfh1-mnh1 | TON_0286 | hydrogenase maturation protein HypF | 0.685606 | 0.778307 | 0.719973 |
| mbx | TON_0494 | Multisubunit $Na^+/H^+$ antiporter, putative MnhB subunit | 0.765286 | 0.716126 | 0.711304 |
| frh | TON_1559 | coenzyme F420 hydrogenase alpha subunit | 0.695408 | 0.64447 | 0.726535 |
| mbx | TON_0487 | nuoD NADH dehydrogenase I, subunit D | 0.606823 | 0.730138 | 0.517528 |
| fdh1-mfh1-mnh1 | TON_0262 | ATPase involved in chromosome partitioning, Mrp homolo | 0.640277 | 0.776389 | 0.619674 |
| frh | TON_1560 | Coenzyme F420 hydrogenase gamma subunit | 0.56769 | 0.715513 | 0.635236 |
| sufII | TON_0054 | hydrogenase subunit gamma | 0.606088 | 0.517724 | 0.630549 |
| fdh1-mfh1-mnh1 | TON_0269 | Multisubunit $Na+/H+$ antiporter, putative MnhB subunit | 0.591411 | 0.571996 | 0.600235 |
| mbx | TON_0486 | 4Fe—4S cluster-binding subunit | 0.821271 | 0.718277 | 0.504388 |
| fdh1-mfh1-mnh1 | TON_0278 | component B or formate hydrogen lyase | 0.720779 | 0.623875 | 0.510273 |
| mbx | TON_0488 | NADH dehydrogenase subunit | 0.703506 | 0.618352 | 0.49939 |
| mbx | TON_0498 | Multisubunit $Na^+/H^+$ antiporter, putative | 0.675578 | 0.564247 | 0.483617 |
| mbx | TON_0489 | nuoB NADH dehydrogenase I, subunit B | 0.797159 | 0.618863 | 0.547462 |
| fdh2-mfh2-mnh2 | TON_1575 | $Na^+/H^+$ antiporter subunit | 0.752784 | 0.646406 | 0.578467 |
| fdh2-mfh2-mnh2 | TON_1577 | Multisubunit $Na^+/H^+$ antiporter, putative MnhB subunit | 0.726511 | 0.655031 | 0.556386 |
| sufI | TON_0544 | alcohol dehydrogenase | 0.87473 | 0.419323 | 0.605934 |
| sufI | TON_0533 | hydrogenase-specific maturation endopeptidase | 0.977803 | 0.516234 | 0.73084 |
| fdh2-mfh2-mnh2 | TON_1572 | hypothetical protein | 0.844948 | 0.504955 | 0.692272 |
| mbx | TON_0492 | MbxH subunit | 0.862715 | 0.484349 | 0.423606 |
| fdh1-mfh1-mnh1 | TON_0279 | NADH ubiquinone oxidoreductase | 0.80929 | 0.515429 | 0.54289 |
| mbh | TON_1584 | MbhC subunit | 0.947559 | 0.514932 | 0.5099 |
| mbh | TON_1583 | MbhB subunit | 1.038442 | 0.519366 | 0.533773 |
| mbh | TON_1588 | MbhG subunit | 1.027148 | 0.563686 | 0.510924 |
| sufII | TON_0052 | hydrogenase subunit alpha | 1.085002 | 0.652365 | 0.550585 |
| fdh2-mfh2-mnh2 | TON_1580 | component F or formate hydrogen lyase | 1.015786 | 0.756283 | 0.529199 |
| mbh | TON_1594 | MbhM subunit | 0.982323 | 0.742211 | 0.458623 |
| codh-mch-mnh3 | TON_1016 | putative transcriptional regulator, ModE family | 1.187798 | 0.634394 | 0.731218 |
| codh-mch-mnh3 | TON_1026 | $Na^+/H^+$ antiporter subunit | 1.337719 | 0.605839 | 0.623499 |
| fdh2-mfh2-mnh2 | TON_1576 | hypothetical protein | 1.168966 | 0.564328 | 0.60819 |
| codh-mch-mnh3 | TON_1022 | respiratory-chain NADH dehydrogenase, subunit 1 | 0.877363 | 1.428883 | 0.57715 |
| fdh1-mfh1-mnh1 | TON_0264 | molybdopterin-guanine dinucleotide biosynthesis protein A | 0.538102 | 0.957335 | 0.826924 |
| sufI | TON_0535 | cytosolic NiFe-hydrogenase, delta subunit | 0.652099 | 1.080516 | 0.800955 |
| mbx | TON_0496 | MbxC subunit | 0.699819 | 1.200655 | 0.995067 |
| fdh2-mfh2-mnh2 | TON_1582 | hypothetical protein | 0.753301 | 0.998059 | 0.952751 |
| fdh1-mfh1-mnh1 | TON_0270 | hypothetical protein | 0.827927 | 0.85379 | 0.581906 |
| fdh1-mfh1-mnh1 | TON_0285 | hypD hydrogenase expression/formation protein | 0.904687 | 1.066448 | 0.758981 |
| mbh | TON_1585 | MbhD subunit | 0.774604 | 1.015909 | 0.670497 |
| mbx | TON_0497 | MbxB subunit | 0.860304 | 0.889029 | 0.810902 |
| frh | TON_1561 | 4Fe—4S ferredoxin, iron-sulfur binding Nitrite/sulfite reductase | 0.824149 | 0.834127 | 0.807754 |
| fdh2-mfh2-mnh2 | TON_1579 | Putative integral membrane protein, DUF68 family | 0.903028 | 0.812346 | 0.816319 |
| fdh2-mfh2-mnh2 | TON_1566 | NADH dehydrogenase (quinone) | 1.011779 | 0.736019 | 0.787627 |
| mbh | TON_1587 | MbhF subunit | 1.129566 | 0.811366 | 0.872572 |
| mbh | TON_1586 | MbhE subunit | 1.101069 | 0.811262 | 0.659266 |
| sufII | TON_0051 | hypothetical protein | 1.273306 | 3.1454 | 2.569546 |
| fdh2-mfh2-mnh2 | TON_1563 | Probable formate dehydrogenase, alpha subunit | 1.008259 | 3.037865 | 3.330042 |
| fdh1-mfh1-mnh1 | TON_0283 | hypC hydrogenase expression/formation protein | 1.007318 | 1.853137 | 2.021914 |
| fdh1-mfh1-mnh1 | TON_0288 | hypothetical protein | 1.004008 | 1.964442 | 2.27641 |
| fdh2-mfh2-mnh2 | TON_1571 | component I or formate hydrogen lyase | 1.030636 | 2.15871 | 1.806722 |
| fdh2-mfh2-mnh2 | TON_1565 | NADH ubiquinone oxidoreductase | 0.811937 | 1.787894 | 2.088693 |
| codh-mch-mnh3 | TON_1031 | component F or formate hydrogen lyase | 1.030507 | 2.788568 | 1.982091 |
| codh-mch-mnh3 | TON_1018 | carbon-monoxide dehydrogenase, catalytic subunit | 1.474238 | 2.204944 | 1.785437 |
| fdh2-mfh2-mnh2 | TON_1569 | component G or formate hydrogen lyase | 1.204795 | 2.281342 | 1.760033 |
| fdh2-mfh2-mnh2 | TON_1570 | formate hydrogen lyase subunit 6 | 1.257649 | 2.427962 | 1.99559 |
| fdh1-mfh1-mnh1 | TON_0287 | hydrogenase expression/formation protein HypE | 0.851301 | 1.399569 | 1.257059 |
| sufII | TON_0055 | sulfhydrogenase II, beta chain | 0.84527 | 1.44889 | 1.452254 |
| frh | TON_1562 | Formate dehydrogenase, subunit FdhD | 0.908701 | 1.54082 | 1.468288 |
| sufII | TON_0053 | Sulfhydrogenase II, delta chain | 0.896129 | 1.898148 | 1.337585 |
| sufI | TON_0539 | probable formate dehydrogenase, alpha subunit | 1.158997 | 1.791123 | 1.314525 |
| codh-mch-mnh3 | TON_1021 | component B or format hydrogen lyase | 1.112538 | 1.711122 | 1.250867 |
| fdh1-mfh1-mnh1 | TON_0263 | hydrogenase maturation protease HycI | 0.775719 | 1.531337 | 1.090123 |
| fdh1-mfh1-mnh1 | TON_0289 | cysteine desulfurase | 0.666768 | 1.534991 | 1.148004 |

TABLE 5-continued

Hierarchical clustering of 112 ORFs including hydrogenase clusters from *T. onnurineus* NA1

| Gene cluster | ORFs | Annotation | M + CO + 0.5 g YE/YPS | M + CO + 1 g YE/YPS | M + CO + 3 g YE/YPS |
|---|---|---|---|---|---|
| mbx | TON_0493 | Multisubunit $Na^+/H^+$ antiporter, putative | 0.70216 | 1.591408 | 1.138149 |
| fdh2-mfh2-mnh2 | TON_1581 | molybdopterin-guanine dinucleotide biosynthesis protein A | 0.61468 | 1.708744 | 1.243367 |
| codh-mch-mnh3 | TON_1019 | putative ATP-binding protein | 0.824732 | 2.016924 | 0.974466 |
| sulfI | TON_0542 | glutamate synthase beta chain-related oxidoreductase | 0.842213 | 1.602828 | 0.936949 |
| mbh | TON_1592 | NiFe-hydrogenase large subunit 1 | 0.940698 | 1.573248 | 0.956935 |
| fdh1-mfh1-mnh1 | TON_0284 | 367aa long hypothetical hydrogenase protein hypD | 1.036497 | 1.385466 | 1.182663 |
| sulfI | TON_0537 | Sulfhydrogenase beta subunit | 1.025726 | 1.458113 | 1.160718 |
| sulfI | TON_0534 | cytosolic NiFe-hydrogenase, alpha subunit | 1.283309 | 1.334781 | 1.071667 |
| fdh2-mfh2-mnh2 | TON_1564 | 4Fe—4S cluster-binding protein | 1.178705 | 1.221574 | 1.445098 |
| fdh2-mfh2-mnh2 | TON_1567 | component B or formate hydrogen lyase | 1.091992 | 1.057076 | 1.184573 |
| fdh2-mfh2-mnh2 | TON_1568 | component C or formate hydrogen lyase | 1.471267 | 1.365925 | 1.382301 |
| fdh2-mfh2-mnh2 | TON_1573 | probable formate transporter | 1.451628 | 1.459657 | 1.158131 |
| fdh2-mfh2-mnh2 | TON_1574 | $Na^+/H^+$ antiporter MnhF subunit, putative | 1.53015 | 1.602287 | 1.244315 |
| sulfI | TON_0541 | 4Fe—4S cluster-binding protein | 1.112648 | 1.320761 | 0.855465 |
| sulfI | TON_0536 | hydrogenase (gamma subunit) | 1.100959 | 1.192121 | 0.759086 |
| codh-mch-mnh3 | TON_1028 | Multisubunit $Na^+/H^+$ antiporter, putative MnhB subunit | 1.019583 | 1.203407 | 0.836452 |
| sulfI | TON_0540 | oxidoreductase iron-sulfur protein | 0.987581 | 1.525167 | 0.82485 |
| codh-mch-mnh3 | TON_1027 | hypothetical protein | 0.991048 | 1.43866 | 0.778446 |
| sulfI | TON_0543 | 4Fe—4S cluster-binding protein | 0.9185 | 1.257283 | 1.019564 |
| sulfI | TON_0538 | probable formate transporter | 0.989789 | 1.113613 | 0.960108 |
| fdh2-mfh2-mnh2 | TON_1578 | Putative integral membrane protein, DUF67 family | 0.989286 | 1.061599 | 0.900044 |
| fdh1-mfh1-mnh1 | TON_0282 | putative transcriptional regulator | 1.340444 | 1.195043 | 0.883294 |
| mbh | TON_1590 | MbhI subunit | 1.334732 | 1.227655 | 0.904813 |
| mbh | TON_1591 | NiFe-hydrogenase small subunit | 1.627315 | 1.158127 | 0.856929 |
| mbh | TON_1589 | MbhH subunit | 1.362042 | 0.948034 | 0.71984 |
| mbh | TON_1595 | 4Fe—4S cluster-binding subunit | 1.589684 | 1.280298 | 0.491906 |
| codh-mch-mnh3 | TON_1030 | Putative integral membrane protein, DUF68 family | 3.779798 | 4.956998 | 1.592196 |
| codh-mch-mnh3 | TON_1024 | NADH dehydrogenase (ubiquinone), 20 kDa subunit | 1.816315 | 3.578841 | 2.009973 |
| codh-mch-mnh3 | TON_1025 | $Na^+/H^+$ antiporter MnhF subunit, putative | 2.443938 | 3.389037 | 1.333503 |
| codh-mch-mnh3 | TON_1029 | Putative integral membrane protein, DUF67 family | 2.648286 | 2.171138 | 1.123898 |
| mbh | TON_1593 | NiFe-hydrogenase large subunit 2 | 1.609483 | 2.286207 | 1.354849 |
| codh-mch-mnh3 | TON_1020 | hypothetical protein | 3.375546 | 9.366047 | 5.425704 |
| codh-mch-mnh3 | TON_1017 | 4Fe—4S ferredoxin, iron-sulfur binding domain | 1.713085 | 4.46107 | 3.621394 |
| codh-mch-mnh3 | TON_1023 | component G or formate hydrogen lyase | 1.927395 | 6.118015 | 4.270288 |

3) Gene Disruption and Phenotype Analysis of Disruption Mutants

Transcriptome analysis suggests that the mch hydrogenase clustered close to codh (FIG. 9A) can play an important role in carboxydotrophic hydrogenogenesis in *T. onnurineus* NA1. However, the up-regulation of the fdh2-mfh2-mnh2 cluster and the high copy number of mRNA of other clusters raise a question about whether codh-mch-mnh3 alone is involved in carboxydotrophic hydrogenogenesis or whether other hydrogenases can become alternative pathways for mch by forming complexes in combination with dehydrogenases or recycling electronic carriers such as $FADH_2$ or NADH. Thus, the present inventors constructed disruption mutants of the large subunit of each of mch and mfh2 hydrogenases (Matsumi, R., K. Manabe, T. Fukui, H. Atomi, and T. Imanaka. 2007. Disruption of a sugar transporter gene cluster in a hyperthermophilic archaeon using a host-marker system based on antibiotic resistance. J. Bacteriol. 189: 2683-2691). The method of constructing the disruption mutants are shown in FIG. 9A. The large subunit of the Mch or Mfh2 hydrogenase gene cluster was disrupted by insertional inactivation of the $P_{gdh}$-hmg$_{Pfu}$ cassette by homologous recombination in the targeted region and the resulting overexpression of the hmg-CoA gene. The targeted gene disruption was confirmed by examining the presence of the $P_{gdh}$-hmg$_{Pfu}$ cassette through PCR amplification after screening candidate groups in a YPS medium supplemented with 10 μM simvastatin (FIG. 9B). $P_{gdh}$-hmg$_{Pfu}$ could be amplified in the disruption candidate groups ($^\Delta$mch$_{TNA}$1 and $^\Delta$mfh2$_{TNA}$1), whereas the amplification of the large subunits of mch or mfh2 was failed. Such results show that the gene disruption system reported in *T. kodakaraensis* KOD1 (Sapra, R., K. Bagramyan, and M. W. W. Adams. 2003. A simple energy-conserving system: Proton reduction coupled to proton translocation. Proc. Natl. Acad. Sci. USA 100: 7545-7550) can also be applied to *T. onnurinues* NA1.

Because the disruption mutants (Δmch$_{TNA}$1 and Δmfh2$_{TNA}$1) could be obtained in the YPS medium, it can be seen that Mch or Mfh2 is not essential for the metabolic consumption of the YPS medium. As can be seen in FIGS. 10A-10D, the changes in the growth and morphology of the mutant strains Δmch$_{TNA}$1 and Δmfh2$_{TNA}$1 confirm that the genes are not necessarily essential in the YPS medium. In addition, the Δmfh2$_{TNA}$1 strain was able to grow and produce hydrogen in the CO-containing growth condition at a level similar to the wild-type strain (FIGS. 7B and 10D). On the other hand, the Δmch$_{TNA}$1 mutant was not able to grow in the CO-containing growth condition and did not produce hydrogen in this condition (FIG. 10C). This indicates that the absence of the large subunit of Mch leads to complete disruption of the carboxydotrophic survival ability of *T. onnurineus* NA1 in the presence of CO. Putting these results together, it appears that, when CO is fed as a substrate, only Mch hydrogenase is involved in growth and hydrogen production.

As described above, the novel hydrogenases of the present invention can produce a large amount of hydrogen by responding specifically to various substrates such as carbon monoxide, formate or starch. According to the hydrogen production methods of the present invention, a large amount of hydrogen can be produced merely by culturing the above-described strain in specific culture conditions. Thus, the methods of the present invention have advantages in that they are more economic and efficient than existing hydrogen production methods and can produce hydrogen even at high temperature.

What is claimed is:

1. A recombinant vector comprising genes that are organized in a CODH-MCH-MNH3 hydrogenase cluster in *T. onnurineus* NA1, and a vector from a source other than *T. onnurineus* NA1, and the vector is a plasmid, a cosmid or a phage,
   wherein the genes include the genes of SEQ ID NO: 21 (CODH dehydrogenase) and SEQ ID NO: 16 (MCH hydrogenase).

2. A host cell transformed with the recombinant vector of claim 1.

3. A recombinant vector comprising genes that are organized in a FDH1-MFH1-MNH1 hydrogenase cluster in *T. onnurineus* NA1, and a vector from a source other than *T. onnurineus* NA1, and the vector is a plasmid, a cosmid or a phage,
   wherein the genes include the genes of SEQ ID NO: 20 (FDH1 dehydrogenase) and SEQ ID NO: 13 (MFH1 hydrogenase).

4. A host cell transformed with the recombinant vector of claim 3.

* * * * *

SEQUENCE LISTING

<160> NUMBER OF SEQ ID NOS: 60

<210> SEQ ID NO 1
<211> LENGTH: 1393
<212> TYPE: PRT
<213> ORGANISM: Thermococcus onnurineus NA1

<400> SEQUENCE: 1

```
Met Gly Phe Leu Ser Arg Leu Phe Gly Gly Lys Lys Glu Thr Asp Thr
1               5                   10                  15

Glu Glu Ile Gln Ile Val Ser Arg Lys Pro Val Gly Lys Phe His Val
            20                  25                  30

Glu Lys Val Phe His Ile Met Gly Arg Glu Thr Leu Val Gly Thr Val
        35                  40                  45

Glu Arg Gly Val Ile Tyr Pro Gly Tyr Lys Val Lys Gly Lys Lys Ala
    50                  55                  60

Ala Val Ile Tyr Arg Ile Glu Lys Gly Arg Lys Ala Val Asp Phe Val
65                  70                  75                  80

Val Asp Gly Asp Lys Ala Ala Leu Ile Leu Glu Gly Ile Thr Lys Ala
                85                  90                  95

Glu Glu Gly Asp Thr Leu Glu Val Tyr Gln Ser Met Ile Ile Glu Leu
            100                 105                 110

Arg Glu Phe Thr Arg Val Glu Gly Asn Gly Lys Ala Glu Ile Val Val
        115                 120                 125

Glu Asn Gly Glu Val Lys Asp Val Arg Leu Lys Ile Val Glu Gly Pro
    130                 135                 140

Arg Phe Phe Glu Leu Leu Thr Leu Gly Arg His Tyr Tyr Asp Val Pro
145                 150                 155                 160

Asp Leu Glu Ala Arg Ile Cys Ala Ile Cys Tyr Leu Ser His Ser Val
                165                 170                 175

Ala Ser Val Leu Gly Ile Glu Lys Ala Phe Gly Val Glu Val Ser Glu
            180                 185                 190

Glu Ile Gln Leu Leu Arg Glu Leu Gly Leu Ile Gly Glu Leu Leu Glu
        195                 200                 205

Ser His Ala Leu His Leu Tyr Leu Leu Val Ala Pro Asp Val Phe Gly
    210                 215                 220

Tyr Pro Asp Ala Ile Arg Met Ala Thr Lys His Gly Glu Leu Val Lys
225                 230                 235                 240

Glu Gly Leu Ala Leu Lys Ala Phe Gly Asn Ser Ile Arg Glu Leu Ile
                245                 250                 255

Gly Gly Arg Glu Ile His Gly Ile Asn Val Lys Pro Gly Gly Phe Gly
            260                 265                 270

Arg Tyr Pro Thr Val Glu Glu Leu Glu Asn Ile Glu Arg Glu Ser Gly
        275                 280                 285

Ala Leu Leu Arg Leu Ala Arg Arg Ala Val Arg Leu Phe Ala Ser Leu
    290                 295                 300

Glu Pro Tyr Gly Glu Lys Ala Gly His Phe Val Ala Thr Asp Gly Tyr
305                 310                 315                 320

Leu Trp Gly Asp Lys Leu Ile Ser Asp Glu Asp Gly Ser Phe His Tyr
                325                 330                 335

Thr Glu Arg Ile Glu Glu Arg Ser Leu Val Tyr Ser Phe Ala Lys Gln
            340                 345                 350

Ser Arg Tyr Lys Gly Glu Pro Phe Phe Val Gly Ala Leu Pro Arg Leu
        355                 360                 365
```

```
Leu Leu Lys Ala Glu Met Leu Thr Pro Thr Ala Lys Arg Leu Phe Glu
    370                 375                 380

Glu His Arg Glu Lys Leu Ala Thr Gly Tyr Val Ser Tyr Asn Asn Leu
385                 390                 395                 400

Ala Gln Ala Ile Glu Leu Val Tyr Ala Leu Glu Arg Ala Gly Glu Ile
                405                 410                 415

Ala Lys Lys Leu Leu Asp Lys Gly Ile Lys Gly Glu Asn Val Pro Val
                420                 425                 430

Glu Val Lys Glu Gly Glu Gly Ile Gly Tyr Val Glu Ala Pro Arg Gly
                435                 440                 445

Val Leu Ile His His Tyr Arg Ile Asp Ser Gly Lys Ile Ala Tyr
    450                 455                 460

Ser Asn Ile Ile Thr Pro Thr Ala Leu Asn His Ala Met Met Glu Ala
465                 470                 475                 480

Ser Leu Phe Lys Glu Ala Arg Lys Leu Tyr Gly Glu Thr Asp Glu Thr
                485                 490                 495

Val Leu Val Gln Arg Leu Glu Glu Thr Val Arg Ala Phe Asp Pro Cys
                500                 505                 510

Ile Ser Cys Ser Val His Ile Val Lys Leu Met Met Asp Lys Leu Lys
                515                 520                 525

Leu Ala Val Phe Glu Leu Thr Asp Cys Gly Gly Cys Ala Leu Asn Ile
    530                 535                 540

Leu Phe Leu Tyr Glu Lys Leu Phe Asp Leu Leu Glu Phe Tyr Glu Ile
545                 550                 555                 560

Thr Glu Phe His Met Ala Thr Ser Leu Ser Glu Gly Ser His Tyr Asp
                565                 570                 575

Val Ala Leu Val Thr Gly Thr Val Ser Ser Gln Arg Asp Leu Ala Leu
                580                 585                 590

Leu Lys Glu Ala Arg Asn His Ser Asp Tyr Leu Ile Ala Leu Gly Thr
    595                 600                 605

Cys Ala Thr His Gly Ser Val Gln Ala Ser Val Glu Gly Ser Ile Arg
    610                 615                 620

Glu Lys Leu Lys Arg Val Tyr Gly Asp Glu Gly Asn Pro Met Arg Ala
625                 630                 635                 640

Leu Asp Ser Lys Pro Val Val Glu Tyr Val Ala Val Asp Phe Ala Leu
                645                 650                 655

Pro Gly Cys Pro Tyr Asp Lys Asn Glu Val Tyr Gln Val Leu Met Asp
                660                 665                 670

Ile Ala Lys Gly Ile Glu Pro Val Lys Asp Tyr Pro Val Cys Val
                675                 680                 685

Glu Cys Lys Leu Asn Glu Tyr Glu Cys Val Leu Val Lys Lys Gly Leu
    690                 695                 700

Pro Cys Leu Gly Pro Ile Thr Tyr Gly Gly Cys Asn Ala Ala Cys Ile
705                 710                 715                 720

Arg Ser Gly Leu Gly Cys Ile Gly Cys Arg Gly Pro Leu Pro Gly Glu
                725                 730                 735

Val Asn Pro Ala Ser Glu Tyr Glu Ile Leu Lys Asp Leu Gly Tyr Asp
                740                 745                 750

Asp Asp Tyr Ile Leu Arg Lys Phe Lys Thr Phe Ala Arg Trp Glu Pro
    755                 760                 765

Met Ser Glu Asn Pro His Gln Thr Tyr Asp Ala Arg Ile Leu Glu Val
770                 775                 780

Lys Asp Leu Thr Pro Arg Glu Lys Leu Phe Thr Leu Arg Phe Leu Asp
```

-continued

```
                785                 790                 795                 800
Pro Glu Ile Gly Glu His Phe Thr Phe Lys Pro Gly Gln Phe Val Ile
                    805                 810                 815
Val Asp Ile Arg Gly Phe Gly Glu Phe Pro Ile Ser Leu Cys Ser Ser
                820                 825                 830
Pro Thr Arg Lys Gly Tyr Ile Gln Leu Cys Ile Arg Lys Ala Gly Arg
                835                 840                 845
Met Thr Lys Phe Ile His Gln Met Lys Glu Gly Glu Val Val Gly Ile
        850                 855                 860
Arg Gly Pro Tyr Gly Asn Gly Phe Pro Met Glu Lys Met Glu Gly Ser
865                 870                 875                 880
Asn Leu Leu Leu Val Ala Gly Leu Gly Met Ala Pro Leu Arg Ser
                    885                 890                 895
Val Leu Trp Tyr Ala Ile Asp Thr Gly Lys Tyr Glu His Val Trp Leu
                900                 905                 910
Leu Tyr Gly Thr Lys Ala Tyr Glu Asp Ile Leu Phe Arg Asp Glu Ile
        915                 920                 925
Ile His Leu Leu Lys His Gly Asp Ala Val Gly Cys Ser Val Lys Leu
    930                 935                 940
Ala Tyr Glu Val Glu Ser Pro Ser Cys Ile Tyr Leu Glu Arg Gly Phe
945                 950                 955                 960
Phe Asp Arg Val Cys Lys Gly Val Val Thr Asp Leu Phe Arg Gly Glu
                965                 970                 975
Glu Phe Asp Val Asp Lys Ala Tyr Ala Leu Ile Cys Gly Pro Pro Val
                980                 985                 990
Met Tyr Arg Phe Val Ile Lys Glu Leu Leu Asp Arg Lys Leu Ser Pro
        995                 1000                1005
Gly Arg Ile Tyr Met Thr Leu Glu Arg Arg Met Arg Cys Gly Ile
    1010                1015                1020
Gly Lys Cys Gly His Cys Ile Val Gly Thr Ser Thr Ser Ile Lys
    1025                1030                1035
Tyr Val Cys Lys Asp Gly Pro Val Phe Thr Tyr Trp Asp Ala Leu
    1040                1045                1050
Ser Thr Arg Gly Leu Ile Leu Arg Tyr Val Lys Leu Ser Ser Glu
    1055                1060                1065
Asn Phe Ser Ser Phe Glu Ser Leu Arg Asn Trp Gly Lys Val
    1070                1075                1080
Tyr Ala Pro Ile Lys Arg Gly Ser Ile Tyr Thr Phe Gln Glu Val
    1085                1090                1095
His Glu Leu Gly Glu Ile Glu Leu Asn Tyr Thr Arg Thr Met Leu
    1100                1105                1110
Pro Pro Lys Lys Phe Phe Val Arg Pro Arg Asp Glu Ile Leu Arg
    1115                1120                1125
Leu Lys Asn Gly Arg Trp Glu Asn Gly Thr Asp Ala Glu Pro Ile
    1130                1135                1140
Val Leu Phe Gly Leu His Ser Cys Asp Met His Gly Leu Lys Ile
    1145                1150                1155
Leu Asp Lys Val Tyr Leu Asp Glu Pro Ala Asp Pro Tyr Tyr Lys
    1160                1165                1170
Ala Arg Arg Glu Lys Thr Phe Ile Val Gly Ile Ser Cys Met Pro
    1175                1180                1185
Asp Glu Tyr Cys Phe Cys Lys Ser Leu Gly Thr His Phe Ala Met
    1190                1195                1200
```

Asp Gly Phe Asp Leu Phe Leu His Glu Leu Pro Asp Gly Trp Leu
    1205                1210                1215

Val Arg Ile Gly Ser Val Arg Gly His Glu Val Val Trp Glu Asn
    1220                1225                1230

Gly Glu Leu Phe Glu Glu Val Thr Asp Glu Asp Leu Lys His Phe
    1235                1240                1245

Lys Glu Phe Glu Glu Arg Arg Ala Asn Ala Phe Gln Lys Glu Ile
    1250                1255                1260

Pro Gln Glu Gly Leu Ala Asp Met Leu Asp Leu Ala Tyr Asn Ser
    1265                1270                1275

Pro Val Trp Lys Glu Tyr Ala Glu Ile Cys Leu Ala Cys Gly Asn
    1280                1285                1290

Cys Asn Met Val Cys Pro Thr Cys Arg Cys Tyr Glu Val Cys Asp
    1295                1300                1305

Asn Trp Ile Ser Ala Tyr Asp Ala Val Arg Glu Arg Arg Tyr Asp
    1310                1315                1320

Ser Cys Phe Met Glu Asn His Gly Leu Val Ala Gly Gly His Asn
    1325                1330                1335

Phe Arg Pro Thr Arg Leu Asp Arg Phe Arg His Arg Tyr Tyr Cys
    1340                1345                1350

Lys Ser Tyr Phe Asp Pro Ser Ser Gly Tyr Asn Cys Val Gly Cys
    1355                1360                1365

Gly Arg Cys Asp Glu Phe Cys Pro Ala Lys Ile Glu His Val Lys
    1370                1375                1380

Val Leu Glu Glu Val Arg Gly Ser Leu Arg
    1385                1390

<210> SEQ ID NO 2
<211> LENGTH: 2496
<212> TYPE: PRT
<213> ORGANISM: Thermococcus onnurineus NA1

<400> SEQUENCE: 2

Met Asn Ala Ser Pro Phe Ile Ile Ser Phe Leu Ile Pro Leu Leu
1               5                   10                  15

Gly Pro Leu Leu Phe Lys Leu Asp Gly Arg Lys Ala Asp Val Phe Met
                20                  25                  30

Leu Ile Ala Val Val Ser Ser Phe Leu Ala Asn Leu Val Gly Val Leu
            35                  40                  45

Glu Tyr Leu Lys Val Gly Gly Ala His His Ile Val Tyr Leu Glu Thr
    50                  55                  60

Ser Ser Leu Gly Glu Val Tyr Gly Val Ile Ile Asp Pro Met Ser Val
65                  70                  75                  80

Leu Val Gly Phe Val Val Ser Leu Ala Gly Val Leu Phe Leu Leu Tyr
                85                  90                  95

Ala Val Asp Tyr Met Ser Glu Arg Asn Lys Gln His Pro Val Tyr Ser
                100                 105                 110

Asp Lys Gly Arg Phe Tyr Ala Trp Met Val Ile Phe Val Gly Ala Thr
            115                 120                 125

Leu Ala Phe Ile Tyr Ser Ser Thr Thr Leu Gln Leu Ile Phe Phe
        130                 135                 140

Glu Ile Met Gly Leu Ala Cys Trp Gly Val Val Gly Tyr Tyr Lys Gly
145                 150                 155                 160

Pro Lys Ala Glu Arg Ala Ala Tyr Lys Ala Leu Leu Val Pro Asn Phe

```
                165                 170                 175
Gly Ala Met Val Gly Leu Tyr Thr Thr Val Gly Ile Gly Ile Leu Lys
            180                 185                 190

Leu His Asp Leu Ser Ile Tyr Ala Leu Gln Asn Leu Asn Asp Glu Leu
            195                 200                 205

Lys Leu Leu Val Phe Leu Gly Val Met Val Ala Ala Phe Thr Lys Ser
            210                 215                 220

Ala Gln Phe Pro Leu Tyr Ser Trp Leu Pro Asp Ala Met Ala Ala Pro
225                 230                 235                 240

Thr Pro Ala Ser Ala Phe Leu His Gly Ala Ala Met Val Glu Met Gly
                245                 250                 255

Val Tyr Leu Leu Ala Arg Val Thr Gln Phe Met Gln Pro Ile Pro Glu
            260                 265                 270

Thr Ala Phe Tyr Val Met Leu Val Phe Val Ser Leu Thr Leu Leu Ile
            275                 280                 285

Ala Ile Leu Tyr Tyr Pro Leu Gln Lys Asp Ala Lys Arg Leu Leu Ala
            290                 295                 300

Tyr Ser Thr Ile Ala Glu Ala Gly Val Met Tyr Val Gly Val Leu Tyr
305                 310                 315                 320

Ala Val Leu Gly Ser Val Tyr Gly Leu Gln Ala Ala Met Phe Gln Leu
                325                 330                 335

Ala Asn His Ala Phe Val Lys Gly Leu Ala Phe Leu Thr Ala Gly Thr
            340                 345                 350

Phe Ser Tyr Ala Phe Gly Thr Leu Asp Met Glu Lys Ile Arg Gly Leu
            355                 360                 365

Gly Lys Leu Val Pro Val Val Gly Ala Ser Trp Phe Leu Ala Leu Leu
            370                 375                 380

Gly Leu Ala Gly Val Pro Pro Leu Gly Leu Phe Phe Ser Lys Ala Tyr
385                 390                 395                 400

Leu Phe Met Asn Ala Ser Ser Ile Thr Ser Trp Val Gly Trp Ile Pro
                405                 410                 415

Leu Phe Leu Val Leu Ala Asp Ala Thr Val Phe Leu Ala Val Ser Leu
            420                 425                 430

Gly Trp Ile Lys Arg Met Val Phe Ser Glu Pro Leu Gln Glu Ser Ala
            435                 440                 445

Glu Val Ser Pro Leu Met Arg Phe Val Leu Val Leu Ile Val Leu
            450                 455                 460

Ser Ile Val Ala Pro Phe Leu Ser Val Lys Leu Val Thr Gln Ile Gly
465                 470                 475                 480

Phe Met Gly Met Met Glu Ile Pro Ile Ala Leu Tyr Ser Leu Ser Ala
                485                 490                 495

Ile Ser Gly Leu Ile Gly Asp Phe Lys Arg Ser Ile Lys Ile Ser Ser
            500                 505                 510

Val Leu Ser Ala Ile Ala Ser Leu Ser Leu Gly Ile Ala Ala His
            515                 520                 525

Ala Leu Ser Arg Gly Leu Pro Val Gln Glu Ser Phe Leu Gly Ile Pro
            530                 535                 540

Leu Ile Ile Asp Ser Leu Ser Leu Pro Phe Leu Phe Ile Ala Leu
545                 550                 555                 560

Leu Ser Leu Val Val Ser Val Tyr Ser Ile Ser Tyr Met Glu Val His
                565                 570                 575

Arg Asp Thr Gly Arg Pro Leu Ala Tyr Thr Ile Leu Tyr Gly Thr Phe
            580                 585                 590
```

```
Val Leu Ser Ile Val Phe Val Ala Leu Thr Ser Asn Leu Leu Trp Phe
            595                 600                 605
Val Phe Phe Trp Glu Leu Met Thr Leu Thr Ser Phe Ile Phe Val Ser
        610                 615                 620
Trp Arg Glu Gln Asp Ala Gly Ile Lys Tyr Leu Leu Thr Met Gln Leu
625                 630                 635                 640
Ala Asn Thr Val Pro Leu Phe Val Ala Leu Gly Ile Ile Tyr Ser Ala
                645                 650                 655
Thr Gly Ser Phe Ser Val Asp Tyr Ala Thr Leu Arg Glu Val Ala Ser
            660                 665                 670
Ser Leu Ser Pro Val Gln Leu Lys Leu Leu Tyr Ala Met Phe Leu Val
        675                 680                 685
Thr Phe Leu Ala Lys Ser Gly Ser Val Pro Phe Gln Phe Trp Val Pro
    690                 695                 700
Asp Ala Tyr Glu Ala Ala Pro Ser Asn Ile Ala Ser Leu Met Ala Gly
705                 710                 715                 720
Val Met Glu Lys Met Ala Val Tyr Gly Leu Ile Arg Leu Leu Cys Asn
                725                 730                 735
Ala Leu Pro Cys Ser Glu Gly Ile Gly Tyr Val Leu Val Ile Val Gly
            740                 745                 750
Ile Leu Thr Met Thr Phe Gly Thr Leu Tyr Ala Leu Arg Glu Thr His
        755                 760                 765
Ala Lys Arg Leu Leu Ala Tyr Ser Ser Val Gly Gln Met Gly Tyr Ile
    770                 775                 780
Trp Phe Ala Val Gly Met Gly Met Ile Phe Leu Thr Met Gly Met Glu
785                 790                 795                 800
Ser Leu Ala Tyr Leu Ala Phe Leu Ala Gly Val Phe His Ser Phe Asn
                805                 810                 815
His Thr Leu Phe Lys Gly Leu Leu Phe Leu Ile Ser Gly Asn Phe Glu
            820                 825                 830
Tyr Ser Ala Gly Thr Ala Asp Leu Asn Glu Leu Gly Gly Leu Arg Arg
        835                 840                 845
Ala Met Pro Tyr Ser Ser Leu Phe Thr Val Ile Gly Ala Leu Ser Leu
    850                 855                 860
Ala Gly Val Pro Leu Phe Ser Gly Phe Leu Ser Lys Trp Met Ile Tyr
865                 870                 875                 880
Gln Ala Gly Tyr Tyr Ser Gly Ile Gly Leu Phe Val Phe Gly Ser Val
                885                 890                 895
Met Ala Val Phe Met Ser Ala Val Thr Leu Ala Tyr Ser Leu Lys Leu
            900                 905                 910
Tyr Thr Ser Ala Phe Gly Gly Glu Pro Asn Glu Arg Thr Glu Asn Ala
        915                 920                 925
Arg Glu Val Pro Ser Gly Met Leu Gly Glu Gly Ile Ile Ala Leu
    930                 935                 940
Thr Ser Leu Ala Val Gly Ile Leu Pro Ala Ile Ala Tyr Pro Ile Leu
945                 950                 955                 960
Thr Ile Ser Leu Asn Gly Gly Asp Val Thr Val Thr Met Gly Ser Ile
                965                 970                 975
Ser Thr Asp Phe Glu Tyr Phe Ser Pro Ile Ala Leu Leu Leu Ala Val
            980                 985                 990
Ser Phe Ile Ala Val Ala Ser Tyr  Phe Val Phe Arg Pro  Lys Thr Thr
        995                 1000                1005
```

```
Asn Val Lys Pro Trp Asn Thr Gly Ala Leu Phe Leu Pro Glu Glu
1010                1015                1020

Arg Tyr Gly Ala Lys Ala Arg Asp Tyr Tyr Arg Gln Tyr Phe Thr
1025                1030                1035

Glu Met Glu Gly Leu Tyr Lys Leu Gly Ser Ala Ala Gly Lys Val
1040                1045                1050

Gly Arg Val Leu Leu Ser Ala Leu Met Ser Val Tyr Leu Val Leu
1055                1060                1065

Ala Arg Gly Leu Val Tyr Thr Gly Arg Glu Lys Lys Arg Ser Phe
1070                1075                1080

Thr Leu Asp Glu Leu Arg His Arg Thr Val Arg Tyr Leu Asp Glu
1085                1090                1095

Ala Phe Phe Ala Pro Met Met Asp Leu Leu Lys Asn Ile Ala Val
1100                1105                1110

Leu Ala Ala Gly Ile Ser Val Ser Met Asp Glu Leu Phe Leu Ala
1115                1120                1125

Ser Met Leu Thr Thr Val Ile Ile Leu Ala Leu Leu Val Leu Met
1130                1135                1140

Asp Tyr Val Ser Ile Ile Ala Ala Pro Ile Val Leu Phe Leu Leu
1145                1150                1155

Pro Pro Phe Leu Asp Gly Ile Gly Arg Arg Ile Lys Ala Arg Ile
1160                1165                1170

Gln Tyr Arg Arg Gly Pro Pro Ile Met Gln Thr Phe Tyr Asp Leu
1175                1180                1185

Glu Lys Leu Leu Lys Leu Pro Ser Val Leu Pro Thr Glu Gly Pro
1190                1195                1200

Ile Phe Arg Leu Ala Pro Tyr Ile Ala Leu Ala Ser Ala Ile Ala
1205                1210                1215

Gly Gly Leu Met Leu Pro Phe Gly Ser Glu Pro Val Leu Ala Phe
1220                1225                1230

Gly Lys Ser Leu Ile Val Phe Phe Tyr Val Met Ala Met Val Ser
1235                1240                1245

Val Val Met Ile Leu Ala Ala Phe Ser Val Gln Asn Ala Phe Ser
1250                1255                1260

His Ile Gly Gly His Arg Glu Val Met Leu Ile Leu Ser Ile Glu
1265                1270                1275

Pro Val Leu Ala Val Val Phe Gly Val Leu Ala Phe Lys Leu Gly
1280                1285                1290

Thr Leu Asn Val Ala Glu Met Pro Phe Ser Ala Asn Leu Ser Leu
1295                1300                1305

Ser Val Ala Leu Ala Tyr Ile Leu Leu Ala Tyr Ala Val Tyr Val
1310                1315                1320

Glu Gly Gly Phe Val Pro Phe Asp Ile Ala Glu Ala Glu Thr Glu
1325                1330                1335

Val Ile Gly Gly Pro Leu Thr Glu Tyr Ser Gly Arg Leu Leu Gly
1340                1345                1350

Val Phe Lys Tyr Ala Leu Leu Val Lys Arg Val Val Leu Leu Trp
1355                1360                1365

Leu Leu Ala Ser Met Ile Val Ile Pro Ala Met Arg Ser Leu Gly
1370                1375                1380

Ile Thr Ser Ser Met Ala Leu Leu Val Ala Gln Leu Val Val Thr
1385                1390                1395

Phe Leu Leu Tyr Ser Leu Ala Val Ala Val Glu Ala Ala Asn Ala
```

```
                1400                1405                1410

Arg Leu Arg Ile Asp Gln Ala Val Ser Leu Asn Lys Lys Val Phe
    1415                1420                1425

Leu Met Ser Leu Ala Val Leu Ile Ile Ala Leu Val Gly Trp Met
    1430                1435                1440

Glu Cys Ser Val Cys Ala Gly Gly Cys Arg Ser Ala Glu Val Glu
    1445                1450                1455

Asp Val Leu Glu Asp Gly His Leu Lys Glu Phe Val Glu Lys Phe
    1460                1465                1470

Arg Gly Ala Ile Phe Glu Cys Lys Lys Leu Thr Arg Asn Gln Tyr
    1475                1480                1485

Leu Phe Ile Val Asp Arg Glu Ala Leu Pro Glu Met Val Leu His
    1490                1495                1500

Trp His Asn His Ser Glu Leu Lys Glu Thr His Phe Ser Met Gly
    1505                1510                1515

Thr Gly Thr Asp Glu Arg Asn Ile Ala Gly Lys Phe Thr Tyr Ala
    1520                1525                1530

Pro Val Ile Asn Val Ala Val Glu Pro Gly Asn Gly Glu Arg Asn
    1535                1540                1545

Tyr Trp Val Ile Leu Lys Ala Tyr Leu Asp Glu Asp Asn Pro Glu
    1550                1555                1560

Phe Pro Ser Ile Ala Ala Lys Leu Pro Ala Ala Leu Trp Ala Glu
    1565                1570                1575

Arg Glu Val Tyr Asp Leu Leu Gly Phe Asn Pro Lys Gly His Pro
    1580                1585                1590

Asp Leu Arg Arg Leu Val Leu Pro Glu Asp Trp Pro Glu Gly Val
    1595                1600                1605

Tyr Pro Leu Arg Lys Asp His Asp Tyr Lys Ala Ser Pro Met Asp
    1610                1615                1620

Thr Pro Lys Cys Tyr Tyr Lys Pro Gly Pro Pro Asp Thr Met Thr
    1625                1630                1635

Val Pro Ile Gly Pro Tyr His Leu Ala Leu Asp Glu Pro Ala His
    1640                1645                1650

Phe Arg Ile Phe Val Lys Gly Glu Thr Val Val Asp Val Asp Tyr
    1655                1660                1665

Arg Gly Phe Tyr Ser His Arg Gly Ile Glu Lys Ile Gly Glu Gly
    1670                1675                1680

Arg Leu Thr Tyr Asn Gln Val Leu Phe Ile Ala Glu Arg Ile Cys
    1685                1690                1695

Gly Ile Cys Gly Phe Gln His Ser Thr Ser Tyr Ala Gln Ala Val
    1700                1705                1710

Glu Asn Ile Ala Gly Val Glu Ile Pro Glu Arg Ala Met Tyr Ile
    1715                1720                1725

Arg Thr Ile Met Leu Glu Ile Glu Arg Ile His Ser His Met Leu
    1730                1735                1740

Trp Ala Gly Val Ala Ala His Leu Thr Gly Phe Asp Thr Gly Phe
    1745                1750                1755

Met His Ala Trp Arg Val Arg Glu Pro Val Met Trp Leu Ala Glu
    1760                1765                1770

Arg Leu Thr Gly Asn Arg Lys Thr Tyr Gly Ile Asn Ile Val Gly
    1775                1780                1785

Gly Val Arg Arg Asp Phe Leu Asp Tyr Arg Lys Glu Met Ile Met
    1790                1795                1800
```

```
Glu Lys Ile Lys Glu Leu Arg Arg Gln Val Glu Glu Phe Ile Glu
    1805            1810                1815

Ile Ala Thr Gly Thr Ala Thr Phe Val Lys Arg Ala Glu Gly Val
    1820            1825                1830

Gly Ile Leu Pro Tyr Lys Val Ala Lys Ala Tyr Ser Val Leu Gly
    1835            1840                1845

Pro Asn Gly Arg Ala Ser Gly Arg Asn Ile Asp Ile Arg Arg Asp
    1850            1855                1860

Gln Pro Phe Ala Ala Tyr Lys Asp Leu Asp Phe Lys Val Pro Val
    1865            1870                1875

Tyr Lys Glu Gly Asp Val Leu Ala Arg Phe Leu Ile Arg Met Asp
    1880            1885                1890

Glu Val Leu Glu Ser Ile Trp Ile Ile Glu Gln Ala Ile Asp Gln
    1895            1900                1905

Met Pro Gly Gly Asp Val Phe Val Pro Ile Gly Glu Leu Pro Glu
    1910            1915                1920

Tyr Glu Ala Leu Gly Tyr Ser Glu Ala Pro Arg Gly Glu Val
    1925            1930                1935

Ile His Tyr Val Met Thr Asp Lys Lys Asn Lys Val Tyr Arg Trp
    1940            1945                1950

Lys Val Arg Ala Pro Thr Tyr Asn Asn Leu Pro Ala Val Pro Glu
    1955            1960                1965

Met Leu Lys Gly Tyr Ser Val Ala Asp Ala Pro Leu Ile Ile Ala
    1970            1975                1980

Ser Ile Asp Pro Cys Tyr Ser Cys Thr Glu Arg Val Gln Ile Val
    1985            1990                1995

Asp Val Glu Thr Gly Lys Ala Gln Thr Leu Asn Glu Gln Gln Phe
    2000            2005                2010

Asn Met Leu Ser Ile Gln Lys Gly Lys Gly Val Ala Met Ala Gln
    2015            2020                2025

Ala Ile Ser Phe Thr Asp Arg Leu Lys Phe Trp Lys Arg Pro Glu
    2030            2035                2040

Glu Asp Val Lys Lys Ala Pro Val Thr Thr Ser Tyr Pro Phe Val
    2045            2050                2055

Asp Ile Glu Lys Pro Pro Glu Tyr Arg Gly Ile Pro Arg Ile Asp
    2060            2065                2070

Pro His Leu Cys Ile Gly Cys Gly Ala Cys Val Arg Ala Cys Pro
    2075            2080                2085

Pro Asp Ala Leu Thr Ile Glu Trp Asp Phe Glu Asn Gly Arg Lys
    2090            2095                2100

Arg Ile Val Phe Asn Ala Ala Arg Cys Ile Arg Cys His Arg Cys
    2105            2110                2115

Val Glu Val Cys Pro Thr Gly Ala Met Gln Gly Thr Thr Arg Phe
    2120            2125                2130

Glu Ile Ala Thr Pro Asn Lys Glu Asp Leu Ile Glu Val Val Asp
    2135            2140                2145

His Lys Leu Tyr Arg Cys Pro Arg Cys Gly Arg Tyr Glu Glu Phe
    2150            2155                2160

Thr Glu Arg Gln Ile Gly Lys Met Phe Gln Ile Leu Pro Glu Glu
    2165            2170                2175

Val Ile Asp Gln His Gly Ile Ala Glu Arg Ala Phe Leu Cys Arg
    2180            2185                2190
```

```
Glu Cys Arg Met Glu Glu Ser Ala Lys Thr Leu Ala Val Gln Gly
    2195                2200                2205

Pro Tyr Ala Asp Ser Leu Leu Ser Leu Tyr Pro Arg Gly Ser
    2210                2215                2220

Lys Val Met Gly Glu Arg Arg Met Ser Gly Leu Lys Ser Val Trp
    2225                2230                2235

Val Phe His Val Asp Ser Gly Ser Cys Asn Gly Cys Asp Ile Glu
    2240                2245                2250

Ile Leu Asp Val Leu Thr Pro Tyr Tyr Asp Ala Glu Arg Leu Gly
    2255                2260                2265

Ile Lys Leu Val Pro Ser Pro Arg His Ala Asp Ala Leu Leu Val
    2270                2275                2280

Ser Gly Pro Leu Thr Arg Gln Thr Tyr Tyr Ala Val Lys Ala Ala
    2285                2290                2295

Tyr Glu Ala Met Pro Pro Lys Pro Arg Ile Val Val Ala Ile Gly
    2300                2305                2310

Thr Cys Ala Ser Ser Gly Gly Ile Phe Tyr Asn Gly Tyr Pro Ile
    2315                2320                2325

Tyr Asn Pro Asn Pro Glu Arg Gly Ser Asp Arg Leu Arg Thr Gly
    2330                2335                2340

Gly Ile Glu Val Leu Leu Ala Glu Tyr Gly Lys Lys Pro Asp Met
    2345                2350                2355

Tyr Ile Pro Gly Cys Pro Pro Ser Pro Glu Glu Ile Leu Tyr Gly
    2360                2365                2370

Leu Ala Gln Leu Leu Gly Leu Lys Glu Lys Lys Met Lys Gly Glu
    2375                2380                2385

Tyr Tyr Tyr Ala Asp Glu Ile Glu Phe Val Leu Pro Glu Arg Pro
    2390                2395                2400

Ile Glu Glu Arg Ile Tyr Leu Thr Leu Arg Glu Ser Leu Arg Arg
    2405                2410                2415

Val Val Gly Tyr Phe Asp Arg Glu Lys Val Leu Glu Asp Phe Met
    2420                2425                2430

Ala Leu Val Glu Lys Ala Gln Glu Ser Glu Asn Pro Arg Glu Arg
    2435                2440                2445

Leu His Glu Leu Val Ile Gly Tyr Phe Leu Arg Glu Lys Asp Ser
    2450                2455                2460

Arg Val Lys Phe Ala Ile Arg Phe Leu Glu Asn Glu Tyr Trp Arg
    2465                2470                2475

Leu Lys Asp Ala Tyr Glu Lys Arg His Leu Ala Leu Val Lys Ala
    2480                2485                2490

Gly Val Arg
    2495

<210> SEQ ID NO 3
<211> LENGTH: 990
<212> TYPE: PRT
<213> ORGANISM: Thermococcus onnurineus NA1

<400> SEQUENCE: 3

Met Val Asp Trp Arg Leu Phe Glu Pro Leu Phe Asn Tyr Ala Arg Lys
1               5                   10                  15

Lys Ser Leu Trp Ile Val Ser Phe Cys Thr Gly Cys Gly Gly Ile Glu
                20                  25                  30

Met Pro Pro Leu Met Thr Ser Arg Tyr Asp Leu Glu Arg Phe Gly Met
            35                  40                  45
```

```
Ile Pro Asp Pro Ser Pro Arg Gln Tyr Asp Leu Phe Leu Ile Thr Gly
    50                  55                  60
Tyr Val Thr Pro Lys Thr Leu Lys Arg Ile Ile Ile Thr Tyr Glu Met
65                  70                  75                  80
Ala Pro Asp Pro Lys Tyr Val Leu Ala His Gly Ser Cys Pro Leu Asn
                    85                  90                  95
Gly Gly Ile Tyr Trp Asp Ala Tyr Asn Ala Ile Lys His Leu Asp Lys
                100                 105                 110
Tyr Ile Pro Val Asp Val Val Ile Ala Gly Cys Met Pro Arg Pro Glu
            115                 120                 125
Ala Val Met Asp Gly Ile Gln Lys Ile Met Glu Met Ile Glu Asn Gly
    130                 135                 140
Thr Ala Asp Gly Trp Lys Arg Tyr Lys Glu Asn Tyr Glu Trp Tyr Lys
145                 150                 155                 160
Lys Asn Gln Asp Glu Leu Phe Gly Gly Trp Arg Glu Arg Glu Ala
                165                 170                 175
Arg Arg Trp Ile Pro Trp Leu Val Asp Lys Lys Glu Glu Met Gly
                180                 185                 190
Glu Val Lys Trp Glu Arg Glu Gln Met Leu Val Asp Lys Ile Leu Glu
    195                 200                 205
Lys Ala Pro Tyr Ala Glu Gly Lys Val Arg Arg Glu Arg Ile Glu
    210                 215                 220
Phe Ser Ile Pro Ala Asp Arg Ile Arg Asp Phe Leu Met Leu Leu Arg
225                 230                 235                 240
Asp Asn Asp Phe Glu Leu Met Leu Gln Ile Thr Thr Val Asp Trp Pro
                245                 250                 255
Asn Asp Gly Glu Leu Glu Leu Ile Tyr Gln Met Trp Ser Val Thr His
                260                 265                 270
Arg Thr His Ala Met Val Arg Thr Arg Ile Pro Arg Asp Leu Asp Lys
        275                 280                 285
Ala Arg Met Pro Thr Val Lys Asp Ile Tyr Pro Val Ala Glu Thr Tyr
    290                 295                 300
Glu Arg Asp Ala His Asp Phe Phe Gly Val Tyr Phe Glu Gly Asn Glu
305                 310                 315                 320
Lys Met Glu Met Pro Trp Ile Leu Asp Asp Thr Glu Gln Gly Leu Phe
                325                 330                 335
Pro His Arg Lys Asp Phe Asp Met Leu Thr Tyr Val Lys Lys Lys Tyr
                340                 345                 350
Lys Leu Leu Asp Arg Phe Asp Glu Asp Lys Asp Asn Tyr Val Ile Met
            355                 360                 365
Val Ser Gln Asn Glu Leu Ile Arg Glu Ala Arg Glu Asn Gly Met Asp
    370                 375                 380
Leu Leu Pro Ile Asp Lys Asp Thr Tyr Glu Leu Phe Phe Gly Pro Gln
385                 390                 395                 400
His Met Ala Thr Glu Asn Phe Ser Ile Ile Leu Lys Met Asp Gly His
                405                 410                 415
Arg Val Val Lys Ala Ile Ala Asn Pro Gly Phe Leu His Arg Gly Phe
            420                 425                 430
Glu Lys Leu Ala Glu Tyr Arg Pro Trp His Thr Asn Ile Ala Leu Leu
        435                 440                 445
Leu Arg Ile Cys Val Pro Glu Pro Asp Val Pro Glu Ala Ile Tyr Ser
    450                 455                 460
```

-continued

Met Ala Val Asp Glu Ile Ile Gly Trp Glu Val Pro Glu Arg Ala Gln
465                 470                 475                 480

Trp Ile Arg Thr Thr Val Leu Glu Met Ala Arg Val Ser Ala Tyr Leu
            485                 490                 495

Phe Trp Ile Met Gly Leu Ser Phe Lys Leu Gly Val Tyr Thr Ala Gly
                500                 505                 510

Gln Trp Ala Ala Ala Tyr Arg Glu Arg Leu Met Ala Leu Phe Glu Gln
            515                 520                 525

Leu Thr Gly Ala Arg Val Tyr His Ile Tyr Thr Ile Pro Gly Gly Val
        530                 535                 540

Arg Arg Asp Ile Pro Gly Asp Lys Trp Leu Arg Gln Leu Lys Asp Thr
545                 550                 555                 560

Val Glu Tyr Ile Arg Ser Lys Leu Ser Asp Phe Asp Asn Leu Val Phe
                565                 570                 575

Glu Asn Tyr Val Ala His Arg Arg Leu Glu Gly Ile Gly Val Met Asp
            580                 585                 590

Lys Lys Phe Ala Leu Ala Glu Gly Val Thr Gly Pro Asn Leu Arg Ala
        595                 600                 605

Thr Gly Val Pro Tyr Asp Val Arg Arg Ala Asp Pro Tyr Leu Leu Tyr
    610                 615                 620

Pro Glu Leu Asp Phe Glu Val Pro Val Leu Lys Glu Gly Asp Ala Leu
625                 630                 635                 640

Ala Arg Ala Leu Ile Arg Arg Phe Glu Leu Glu Gln Asp Leu Tyr Ile
                645                 650                 655

Leu Asp Gln Leu Leu Glu Met Gly Pro Pro Ser Gly Pro Tyr Lys Val
            660                 665                 670

Glu Asp Pro Lys Leu Lys Asn Leu Pro Arg Phe Lys Val Pro Ala Gly
        675                 680                 685

Asp Ala Phe Ala His Val Glu Ser Thr Lys Gly Asp Phe Gly Ala Tyr
    690                 695                 700

Val Val Ser Asp Gly Lys His Lys Pro Tyr Arg Val Gln Ile Arg Gly
705                 710                 715                 720

Pro Ser Ile Ala His Gly Val Arg Val Leu Glu Gln Leu Leu Val Gly
                725                 730                 735

Ala Arg Ile Ala Asp Val Pro Val Ile Leu Met Ser Leu Asp Asn Cys
            740                 745                 750

Pro Pro Asp Ile Asp Arg Met Glu Val Asp Phe Lys Val Ala Pro Glu
        755                 760                 765

Glu Lys Val Arg Lys Pro Ser Phe Ile Lys Pro Trp Met Gly Leu
    770                 775                 780

Lys Tyr Leu Phe Lys Lys Pro Val Thr Ile Lys Ile Pro Tyr Glu Arg
785                 790                 795                 800

Val Gln Ile Ala Lys Asp Tyr Arg Gly Phe His Thr Leu Asp Trp Lys
                805                 810                 815

Lys Cys Val Gly Cys Asn Phe Cys Gly Gln Ile Cys Pro Ala Arg Ala
            820                 825                 830

Ile Glu Met Thr Trp Ile Glu Val Asp Gly Lys Met Glu Lys Arg Pro
        835                 840                 845

His Pro Lys Ile Asp Tyr Gly Arg Cys Thr Phe Cys Glu Phe Cys Val
    850                 855                 860

Asp Val Cys Pro Pro Gly Ala Leu Gly Phe Ile Glu Asn Tyr Ile Leu
865                 870                 875                 880

Thr Thr Glu Trp Lys Asp Glu Glu Leu Glu Leu Phe Asp Trp Val Pro

-continued

```
                885                 890                 895
Ile His Pro Asp Lys Phe Arg Glu Ile Asn Glu Lys Phe Pro Asp Tyr
            900                 905                 910

Arg Phe Pro Val Glu Lys Ile Glu Phe Asn Lys Glu Thr Lys Glu Val
            915                 920                 925

Thr Tyr Tyr Leu Arg Asp Gly Glu Val Met Lys Phe Lys Ile Leu Gly
            930                 935                 940

Tyr Gly Ile Arg Pro Pro Lys Pro Pro Thr Lys Pro Ala Gln Lys Ala
945                 950                 955                 960

Ala Ala Lys Ala Ala Glu Lys Asn Asp Thr Lys Pro Val Glu Lys Pro
            965                 970                 975

Thr Glu Lys Lys Glu Ala Gly Lys Ile Glu Glu Lys Lys Glu
            980                 985                 990

<210> SEQ ID NO 4
<211> LENGTH: 3724
<212> TYPE: PRT
<213> ORGANISM: Thermococcus onnurineus NA1

<400> SEQUENCE: 4

Met Glu Thr Leu Ile Leu Ala Leu Gly Asn Glu Leu Met Lys Asp Asp
1               5                   10                  15

Gly Val Gly Leu Lys Val Gly Arg Leu Leu Ala Glu Lys Gly Tyr Asn
            20                  25                  30

Val Leu Glu Val Gly Thr Asp Ile Phe Met Leu Gln Ser His Tyr Ser
        35                  40                  45

Gly Glu Glu Arg Leu Ile Ile Ile Asp Ala Ile Leu Ser Glu Lys Phe
    50                  55                  60

Lys Pro Gly Glu Ile Ile His Val Ser Gly Gly Glu Val Phe Glu Lys
65                  70                  75                  80

Leu Lys Ala Glu Ile Arg Ser Ala His Phe Met Gly Ala Ile Asp Gly
                85                  90                  95

Leu Lys Leu Leu Met Ala Leu Asp Glu Arg Leu Ala Asn Val Glu Ile
            100                 105                 110

His Phe Ile Gly Ile Val Ala Lys Glu Ile Asn Leu Gly Met Glu Leu
        115                 120                 125

Thr Glu Glu Val Arg Glu Ala Leu Pro Lys Ala Val Glu Leu Val Glu
    130                 135                 140

Glu Leu Val Lys Lys Met Lys Asn Leu Tyr Leu Pro Ile Thr Val Asp
145                 150                 155                 160

His Ile Ala Arg Val Glu Gly Lys Gly Gly Val Glu Ile Val Val Gly
                165                 170                 175

Asp Asp Gly Val Lys Glu Val Lys Leu Asn Ile Ile Glu Gly Pro Arg
            180                 185                 190

Phe Phe Glu Ala Ile Thr Ile Gly Lys Lys Leu Asp Glu Ala Leu Ala
        195                 200                 205

Val Tyr Pro Arg Ile Cys Ser Phe Cys Ser Ala Ala His Lys Leu Thr
    210                 215                 220

Ala Val Glu Ala Ala Glu Lys Ala Val Gly Phe Glu Val Arg Glu Glu
225                 230                 235                 240

Ile Gln Ala Leu Arg Glu Val Leu Tyr Ile Gly Asp Met Ile Glu Ser
                245                 250                 255

His Ala Leu His Leu Tyr Leu Leu Val Leu Pro Asp Tyr Met Gly Tyr
            260                 265                 270
```

```
Ser Asn Pro Leu Lys Met Leu Asp Lys Tyr Lys Lys Glu Ile Asn Ile
        275                 280                 285

Ala Leu Asp Leu Lys Asn Leu Gly Ser Trp Met Met Asp Glu Leu Gly
290                 295                 300

Ala Arg Ala Ile His Gln Glu Asn Val Val Met Gly Gly Phe Gly Lys
305                 310                 315                 320

Leu Pro Asp Lys Thr Thr Leu Glu Lys Met Lys Lys Arg Leu Gln Glu
                325                 330                 335

Ala Leu Pro Leu Ala Glu Tyr Thr Phe Glu Leu Phe Ser Lys Leu Glu
                340                 345                 350

Gln Tyr Glu Glu Val Glu Gly Pro Ile Ile His Met Ala Val Arg Pro
            355                 360                 365

Arg Gly Asp Val Tyr Gly Ile Tyr Gly Asp Ala Ile Ser Val Ser Asp
    370                 375                 380

Gly Phe Glu Phe Pro Ser Glu Gly Tyr Lys Lys His Met Val Glu Arg
385                 390                 395                 400

Val Val Glu His Ser Phe Ala Lys His Ser Phe Tyr Asn Gly Glu Lys
                405                 410                 415

Pro Phe Met Thr Gly Ala Ile Ser Arg Val Val Asn His Ala Asp Lys
                420                 425                 430

Leu Tyr Gly Arg Ala Lys Glu Leu Tyr Glu Ser His Lys Asp Leu Leu
            435                 440                 445

Arg Pro Thr Asn Pro Phe Ala Asn Asn Leu Ala Gln Ala Leu Glu Leu
    450                 455                 460

Val Tyr Phe Met Glu Arg Gly Ile Asp Leu Ile Asp Glu Ala Leu Ala
465                 470                 475                 480

Lys Trp Pro Ile Arg Pro Arg Asp Glu Val Asp Val Lys Asp Gly Phe
                485                 490                 495

Gly Val Ser Thr Thr Glu Ala Pro Arg Gly Ile Leu Val Tyr Ala Leu
            500                 505                 510

Glu Val Lys Asp Gly Arg Val Ala Tyr Asp Ile Ile Thr Pro Thr
    515                 520                 525

Ala Phe Asn Leu Ala Met Met Glu Val His Val Arg Met Met Ala Glu
530                 535                 540

Lys His Tyr Asn Asp Asp Pro Glu Arg Leu Lys Leu Leu Ala Glu Met
545                 550                 555                 560

Val Val Arg Ala Tyr Asp Pro Cys Ile Ser Cys Ser Val His Val Ala
                565                 570                 575

Arg Leu Met Glu Gly Lys Val Arg Ile Gly Phe Tyr Ala Leu Thr Ser
            580                 585                 590

Cys Tyr Gly Cys Gln Leu Arg Phe Ala Met Met Asp Glu Ile Leu Gln
    595                 600                 605

Leu Leu Pro Asn Ala Glu Ile Val Cys Trp Tyr Met Leu Asp Arg Asp
610                 615                 620

Ser Ser Glu Asp Glu Pro Val Asp Ile Ala Phe Ile Glu Gly Ser Val
625                 630                 635                 640

Ser Thr Glu Glu Glu Val Glu Leu Val Lys Lys Ile Arg Glu Asn Ala
                645                 650                 655

Lys Ile Val Val Ala Val Gly Ala Cys Ala Thr Gln Gly Gly Val Gln
                660                 665                 670

Ser Trp Glu Lys Asp Lys Ser Leu Glu Glu Leu Trp Lys Ala Val Tyr
            675                 680                 685

Gly Asp Gly Lys Val Lys Phe Glu Pro Lys Met Ala Glu Pro Leu Glu
```

```
              690              695              700
Asn Tyr Ile Lys Val Asp Tyr Arg Ile Tyr Gly Cys Pro Pro Glu Lys
705              710              715              720

Lys Asp Phe Ile Tyr Ala Ile Gly Thr Phe Leu Val Gly Ser Trp Pro
                 725              730              735

Glu Asp Ile Asp Tyr Pro Val Cys Leu Glu Cys Arg Leu Lys Gly Asn
                 740              745              750

Thr Cys Ile Leu Ile Glu Lys Gly Glu Pro Cys Leu Gly Pro Ile Thr
                 755              760              765

Arg Ala Gly Cys Asp Ala Arg Cys Pro Ser Tyr Gly Ile Ala Cys Ile
                 770              775              780

Gly Cys Arg Gly Ala Ile Gly Tyr Asp Val Ala Trp Phe Asp Ser Leu
785              790              795              800

Ala Arg Thr Phe Lys Glu Lys Gly Leu Thr Lys Glu Glu Ile Leu Glu
                 805              810              815

Arg Met Lys Ile Phe Asn Ala His Asn Pro Lys Leu Glu Glu Met Val
                 820              825              830

Asp Lys Val Phe Gln Phe Gln Gly Val Lys Glu Met Asn Glu Ala His
                 835              840              845

Val Cys Met Cys His Asp Asn Pro Tyr Ala Leu Asp Arg Val Lys Val
850              855              860

Leu Arg Val Tyr Arg Leu Thr Glu Thr Glu Lys Leu Phe Leu Phe Arg
865              870              875              880

Phe Glu Asp Gln Glu Ile Ala Glu Asn Trp Thr Phe Lys Pro Gly Gln
                 885              890              895

Phe Val Gln Leu Thr Ile Pro Gly Val Gly Glu Val Pro Ile Ser Ile
                 900              905              910

Cys Ser Ser Pro Met Lys Arg Gly Phe Phe Glu Leu Cys Ile Arg Lys
                 915              920              925

Ala Gly Arg Val Thr Thr Val His Lys Leu Lys Pro Gly Asp Thr
930              935              940

Val Leu Val Arg Gly Pro Tyr Gly Asn Gly Phe Pro Val Asp Glu Trp
945              950              955              960

Glu Gly Met Asp Leu Leu Leu Ile Ala Ala Gly Leu Gly Thr Ala Pro
                 965              970              975

Leu Arg Ser Val Phe Leu Tyr Ala Met Asp Asn Arg Trp Lys Tyr Gly
                 980              985              990

Asn Ile Thr Phe Ile Asn Thr Ala Arg Tyr Gly Lys Asp Leu Leu Phe
                 995              1000             1005

Tyr Lys Glu Leu Glu Ala Met Lys Asp Leu Ala Glu Ala Glu Asn
1010             1015             1020

Val Gln Ile Ile Gln Ser Val Thr Arg Asp Pro Asp Trp Pro Gly
1025             1030             1035

Arg His Gly Arg Pro Gln Lys Phe Ile Val Glu Ala Asn Thr Asn
1040             1045             1050

Pro Lys Asn Thr Ala Ile Ala Ile Cys Gly Pro Pro Arg Met Tyr
1055             1060             1065

Lys Ala Val Phe Glu Ala Leu Ile Asn Tyr Gly Tyr Arg Pro Glu
1070             1075             1080

Asn Ile Tyr Val Thr Leu Glu Arg Lys Met Lys Cys Gly Ile Gly
1085             1090             1095

Lys Cys Gly His Cys Asn Val Gly Thr Ser Thr Ser Trp Lys Tyr
1100             1105             1110
```

```
Val Cys Arg Asp Gly Pro Val Phe Thr Tyr Phe Asp Ile Val Ser
1115                 1120                 1125

Thr Pro Gly Leu Leu Asp Met Arg Tyr Val Lys Leu Pro Lys Glu
1130                 1135                 1140

Asn Thr Tyr Glu Phe Leu Glu Arg Leu Lys Asn Leu Gly Lys Leu
1145                 1150                 1155

Tyr Ala Pro Val Lys Ile Ser Asp Gln Phe Tyr Asp Phe Arg Glu
1160                 1165                 1170

Ile Asp Asp Val Arg Lys Ile Glu Phe Asn Tyr Thr Arg Thr Leu
1175                 1180                 1185

Met Pro Pro Lys Lys Phe Phe Phe Ala Pro Arg Glu Lys Met Phe
1190                 1195                 1200

Glu Phe Ser Ile Ser Lys Ala Glu Tyr Arg Glu Val Ile Pro Glu
1205                 1210                 1215

Val Glu Pro Phe Val Leu Phe Gly Leu His Ala Cys Asp Ile Tyr
1220                 1225                 1230

Gly Leu Lys Ile Leu Asp Ser Val Tyr Leu Asp Glu Tyr Pro Asp
1235                 1240                 1245

Lys Tyr Tyr Lys Val Arg Arg Glu Lys Gly Ile Ile Ile Gly Ile
1250                 1255                 1260

Ser Cys Met Pro Asp Glu Tyr Cys Phe Cys Asn Leu Leu Arg Thr
1265                 1270                 1275

Asp Phe Glu His Asp Gly Phe Asp Leu Phe Phe His Glu Leu Pro
1280                 1285                 1290

Asp Gly Trp Leu Ile Arg Ile Gly Thr Pro Thr Gly His Arg Ile
1295                 1300                 1305

Val Asp Lys Asn Ile Lys Leu Phe Thr Glu Val Ala Gln Glu Asp
1310                 1315                 1320

Ile Cys Asn Phe Arg Glu Phe Glu Arg Lys Arg Ala Gln Ala Phe
1325                 1330                 1335

Arg Tyr His Glu Glu Trp Asp Asn Ile His Tyr Leu Leu Glu Leu
1340                 1345                 1350

Glu Met Glu His Pro Leu Trp Glu Lys Glu Ala Glu Lys Cys Phe
1355                 1360                 1365

Ala Cys Gly Asn Cys Ser Thr Val Cys Pro Thr Cys Arg Cys Tyr
1370                 1375                 1380

Glu Val Gln Asp Ile Val Asn Leu Asp Gly Asp Thr Gly Tyr Arg
1385                 1390                 1395

Glu Arg Arg Trp Asp Ser Cys Lys Phe Arg Ser His Gly Leu Val
1400                 1405                 1410

Ala Gly Gly His Asn Phe Arg Pro Thr Lys Lys Asp Arg Phe Ile
1415                 1420                 1425

Asn Arg Tyr Leu Cys Lys Met Ser Phe His Trp Thr Leu Gly Ile
1430                 1435                 1440

Asn Phe Cys Val Gly Cys Gly Arg Cys Thr Ala Phe Cys Pro Ala
1445                 1450                 1455

Gly Ile Asp Phe Val Lys Asn Leu Arg Ile Ile Ala Gly Leu Glu
1460                 1465                 1470

Asp Ala Ser Cys Pro Ser Lys Leu Ser Glu Glu Ile Pro Lys Lys
1475                 1480                 1485

Gly Phe Ala Tyr Ala Asn Asn Ile Arg Gly Glu Asp Ile Met Ala
1490                 1495                 1500
```

-continued

Gln Asn Asn Ser Leu Val Leu Tyr Asp Val His Glu Thr Val Asp
1505                1510                 1515

Val Cys Ser Asn Val Gly Cys Val Lys Thr Lys Ala Thr Pro Ser
1520                1525                 1530

Arg Leu Leu Phe Ala Gly Phe Met Ala Gly Ala Tyr Ile Ala Phe
1535                1540                 1545

Gly Phe Ile Phe Ala Ile Val Ala Ser Ala Ser Phe His Pro Lys
1550                1555                 1560

Leu Gly Thr Phe Pro Asn Leu Ser Leu Phe Lys Leu Leu Leu Gly
1565                1570                 1575

Ala Val Phe Pro Val Gly Leu Ile Ala Val Leu Leu Gly Gly Ala
1580                1585                 1590

Asp Leu Trp Thr Gly Asn Ala His Ile Val Thr Leu Ser Lys Met
1595                1600                 1605

Thr Gly Arg Ala Ser Val Lys Asp Val Leu Tyr Asn Trp Ile Gly
1610                1615                 1620

Ser Tyr Thr Gly Asn Phe Val Gly Ser Val Phe Leu Ala Phe Leu
1625                1630                 1635

Ala Val Tyr Gly Thr Gly Leu Met Ala Gly Gly Leu Phe Lys Asp
1640                1645                 1650

Val Leu Ile Gly Ile Gly Asn Tyr Lys Val Ala Leu Thr Pro Trp
1655                1660                 1665

Lys Ala Leu Trp Leu Gly Ile Gly Cys Asn Trp Leu Val Asn Val
1670                1675                 1680

Ala Ile Trp Leu Tyr Ile Arg Ala Lys Asp Thr Ala Gly Lys Val
1685                1690                 1695

Ile Val Thr Trp Phe Pro Ile Phe Ala Phe Val Ala Ile Gly Phe
1700                1705                 1710

Glu His Ser Ile Ala Asn Met Trp Ala Ile Ser Ala Ser Ile Phe
1715                1720                 1725

Ala Ser Asp Gly Ala Ile Ser Trp Val Gln Phe Phe His Asn Ile
1730                1735                 1740

Ile Pro Val Thr Ile Gly Asn Ala Ile Gly Gly Phe Leu Phe Val
1745                1750                 1755

Gly Phe Tyr His Trp Tyr Leu Ala Asp Gly Arg Asn Ala Ile Lys
1760                1765                 1770

Glu Leu Ile Asp Phe Val Glu Val Leu Ala Leu Phe Val Phe Ile
1775                1780                 1785

Met Val Leu Ile Pro Ala Gly Ile Ala Tyr Ala Leu Ser Gly Leu
1790                1795                 1800

Gly Asn Ile Ala Thr Trp Leu Val Pro Leu Ile Ile Ser Val Tyr
1805                1810                 1815

Gly Val Val Met Thr Tyr Leu Val Arg Arg Ala Leu Met Glu Glu
1820                1825                 1830

Phe Lys Ile Gly Leu Cys Pro Tyr Cys Gly Met Gly Cys Arg Phe
1835                1840                 1845

Tyr Ile Lys Thr Leu Asn Gly Gln Pro Ile Gly Ile Glu Pro Tyr
1850                1855                 1860

Pro Gly Gly Val Asn Glu Gly Lys Leu Cys Pro Lys Gly Val Ala
1865                1870                 1875

Ala Val Asp Phe Leu Arg His Lys Asp Arg Leu Lys Lys Pro Leu
1880                1885                 1890

Lys Arg Thr Glu Asn Gly Phe Val Glu Ile Ser Trp Glu Gln Ala

-continued

```
              1895                1900                1905
Ile Lys Glu Ile Ala Glu Lys Leu Leu Glu Ile Arg Glu Lys Tyr
     1910                1915                1920
Gly Pro Asp Thr Leu Gly Phe Phe Ser Ser Ala Arg Cys Ser Asn
     1925                1930                1935
Glu Glu Asn Tyr Leu Leu Gln Lys Ile Ala Arg Leu Leu Gly Thr
     1940                1945                1950
Asn Asn Val Asp His Cys Ala Arg Leu Cys His Ala Ser Thr Val
     1955                1960                1965
Val Gly Leu Ala Gln Thr Val Gly Ala Ala Gln Ser Gly Ser
     1970                1975                1980
Tyr Thr Asp Ile Pro Lys Ala Lys Val Leu Leu Ile Trp Gly Tyr
     1985                1990                1995
Asn Pro Ser Glu Thr His Pro Val Leu Met Arg Tyr Ile Leu Arg
     2000                2005                2010
Ala Arg Asp Asn Gly Ala Lys Ile Ile Val Val Asp Pro Arg Lys
     2015                2020                2025
Thr Arg Thr Val Trp Phe Ala Asp Met His Leu Gln Leu Lys Pro
     2030                2035                2040
Gly Thr Asp Ile Val Leu Ala Asn Ala Met Met His Val Ile Ile
     2045                2050                2055
Glu Glu Arg Leu Tyr Asp Arg Glu Phe Ile Met Asn Arg Thr Lys
     2060                2065                2070
Gly Phe Glu Lys Leu Ile Ala Ala Val Gln Lys Tyr Thr Pro Glu
     2075                2080                2085
Tyr Ala Glu Glu Ile Thr Gly Val Pro Ala Lys Leu Ile Arg Glu
     2090                2095                2100
Ala Ala Ile Thr Phe Ala Thr Ala Gly Arg Gly Ile Val Met Trp
     2105                2110                2115
Ala Met Gly Leu Thr Gln His Val Thr Gly Ala Ala Asn Val Lys
     2120                2125                2130
Ala Leu Ala Asp Leu Ala Leu Ile Cys Gly Tyr Val Gly Arg Glu
     2135                2140                2145
Gly Thr Gly Leu Phe Pro Met Arg Gly Gln Asn Asn Val Gln Gly
     2150                2155                2160
Ala Cys Asp Met Ala Ala Leu Pro Asn Val Phe Pro Gly Tyr Gln
     2165                2170                2175
Lys Val Thr Asp Asp Glu Lys Arg Lys His Val Ala Glu Ile Trp
     2180                2185                2190
Gly Val Glu Asp Leu Pro Ser Lys Pro Gly Leu Thr Ile Pro Glu
     2195                2200                2205
Met Ile Asp Ala Ala Ala Lys Gly Glu Leu Lys Ala Leu Tyr Ile
     2210                2215                2220
Met Gly Glu Asn Pro Val Met Ser Asp Pro Asn Thr Lys His Val
     2225                2230                2235
Ile Glu Ala Leu Lys Asn Leu Glu Leu Leu Val Val Gln Asp Ile
     2240                2245                2250
Phe Leu Thr Glu Thr Ala Glu Leu Ala His Tyr Val Leu Pro Ala
     2255                2260                2265
Ala Ala Tyr Ala Glu Lys Glu Gly Ser Phe Thr Ala Ser Glu Arg
     2270                2275                2280
Arg Val Gln Trp Asn Phe Lys Ala Ile Glu Pro Pro Gly Glu Ala
     2285                2290                2295
```

-continued

```
Lys Pro Asp Trp Glu Ile Leu Thr Met Leu Gly Lys Ala Leu Gly
    2300                2305                2310
Leu Pro Lys Phe Asp Tyr Ser Asp Val Glu Asp Ile Thr Arg Glu
    2315                2320                2325
Ile Thr Leu Val Ala Pro Gln Tyr Arg Gly Ile Thr Pro Glu Arg
    2330                2335                2340
Leu Lys Arg Glu Val Met Gly Val Gln Trp Pro Cys Pro Ser Glu
    2345                2350                2355
Asp His Pro Gly Thr Pro Arg Leu His Val Glu Arg Phe Ala Thr
    2360                2365                2370
Pro Asp Gly Lys Ala Asn Ile Ile Pro Val Glu Phe Lys Pro Pro
    2375                2380                2385
Ala Glu Glu Pro Asp Glu Glu Tyr Pro Phe Ile Leu Thr Thr Phe
    2390                2395                2400
Arg Ile Val Gly Gln Tyr His Thr Leu Thr Met Ser Asn Arg Ser
    2405                2410                2415
Glu Ser Leu Lys Lys Arg Trp Ser Ser Pro Tyr Ala Gln Ile Ser
    2420                2425                2430
Pro Glu Asp Ala Lys Lys Leu Gly Ile Gln Asp Gly Glu Met Ile
    2435                2440                2445
Arg Ile Val Thr Arg Arg Gly Ser Tyr Thr Cys Arg Ala Val Val
    2450                2455                2460
Thr Glu Asp Val Ser Glu Gly Val Ile Ala Val Pro Trp His Trp
    2465                2470                2475
Gly Ala Asn Ile Leu Thr Asn Asp Val Leu Asp Pro Glu Ala Lys
    2480                2485                2490
Ile Pro Glu Leu Lys Val Ala Ala Cys Arg Val Glu Lys Ile Gly
    2495                2500                2505
Gly Cys Met Glu Lys Lys Leu Phe Ile Asn Leu Gly Arg Cys Ile
    2510                2515                2520
Ala Cys Arg Ala Cys Glu Val Ala Cys Glu Lys Glu His Gly Ile
    2525                2530                2535
Ser Phe Ile Thr Val Tyr Glu Phe Arg Asp Ile Ala Val Pro Leu
    2540                2545                2550
Asn Cys Arg His Cys Glu Lys Ala Pro Cys Ile Glu Val Cys Pro
    2555                2560                2565
Thr Lys Ala Ile Tyr Arg Asp Glu Asp Gly Ala Val Val Ile Asp
    2570                2575                2580
Glu Ser Lys Cys Ile Gly Cys Tyr Met Cys Ser Ala Val Cys Pro
    2585                2590                2595
Tyr Ala Ile Pro Ile Val Asp Pro Ile Lys Glu Leu Ala Val Lys
    2600                2605                2610
Cys Asp Leu Cys Ala Glu Arg Arg Lys Glu Gly Arg Asp Pro Leu
    2615                2620                2625
Cys Ala Ala Val Cys Pro Thr Asp Ala Ile Ile Tyr Ala Asp Leu
    2630                2635                2640
Asn Glu Leu Met Glu Glu Lys Arg Arg Arg Lys Ala Glu Arg Ile
    2645                2650                2655
Val Glu Ala Gln Arg Lys Ala Val Glu Thr Leu Ala Tyr Phe Gly
    2660                2665                2670
Val Leu Lys Val Glu Leu Cys Val Gly Cys Gly Val Cys Ala Lys
    2675                2680                2685
```

```
Ala Cys Pro His Ser Ala Ile Ser Val Phe Glu Asp Ser Val Arg
2690                2695                2700

Arg Ile Val Phe Asp Pro Lys Lys Cys Glu Glu Cys Ser Phe Glu
2705                2710                2715

Cys Asn Glu Ala Cys Pro Thr Gly Ala Leu Glu Gly Lys Ser Asp
2720                2725                2730

Lys Arg Glu Leu Val Phe Glu Phe Ala Tyr Cys Ala Ile Cys Gly
2735                2740                2745

Lys Arg Leu Asn Ile Val Lys Glu Glu Ala Glu Tyr Leu Ala Lys
2750                2755                2760

Lys Leu Ile Glu Leu Gly Glu Asn Pro Glu Ile Ala Phe Leu Cys
2765                2770                2775

Asp Asp Cys Lys Arg Lys Arg Leu Phe Gly Val Ala Asn Lys Tyr
2780                2785                2790

Glu Ala Tyr Leu Gly Met Ser Gly Met Arg Phe Ala Phe Leu Cys
2795                2800                2805

Arg Glu Arg Pro Glu Pro Thr Gly Lys Lys Ile Ala Val Ile Gly
2810                2815                2820

Ala Gly Pro Ala Gly Leu Ala Ala Thr Gly Tyr Leu Val Cys Gln
2825                2830                2835

Gly His Glu Val His Val Tyr Asp Lys Leu Pro Glu Pro Gly Gly
2840                2845                2850

Leu Met Leu Phe Gly Ile Pro Glu Phe Arg Ile Pro Ile Tyr Arg
2855                2860                2865

Val Arg Glu Gly Tyr Glu Glu Leu Glu Arg Val Tyr Asn Val Lys
2870                2875                2880

Phe Phe Thr Arg Thr Lys Val Tyr Phe Gly Asn Leu Glu Gly Glu
2885                2890                2895

Ser Gly Asp Glu Phe Val Glu Asn Arg Val Asp Phe Lys Glu Leu
2900                2905                2910

Val Glu Lys Tyr Asp Ala Val Leu Ile Ala Thr Gly Thr Trp Lys
2915                2920                2925

Cys Trp Ile Pro Asn Ile Glu Gly Ala Glu Leu Glu Gly Val Phe
2930                2935                2940

Pro Ala Leu Glu Tyr Leu Phe Arg Ile Lys Ser Ala Lys Leu Gly
2945                2950                2955

His Met Asp Trp Gly Lys Val Thr Pro Val Glu Gly Lys Lys Val
2960                2965                2970

Leu Val Val Gly Ala Gly His Thr Ala Val Asp Ala Ala Leu Glu
2975                2980                2985

Ser Val Leu Leu Gly Ala Asp Lys Val Tyr Leu Ser Tyr Arg Arg
2990                2995                3000

Thr Ile Arg Glu Ala Pro Ala Gly Ala Tyr Glu Ile Asn Leu Leu
3005                3010                3015

Gln Gln Arg Gly Val Lys Trp Leu Glu Arg Thr Met Pro Val Arg
3020                3025                3030

Ile Ile Gly Glu Asn Gly Lys Val Arg Ala Val Glu Leu Val Lys
3035                3040                3045

Thr Lys Leu Ser Glu Pro Asp Glu Ser Gly Arg Arg Arg Pro Val
3050                3055                3060

Pro Ile Glu Gly Ser Asn Phe Gln Ile Asp Val Asp Tyr Val Ile
3065                3070                3075

Phe Ala Val Gly Gln Ser Pro Thr Pro Pro Phe Ala Glu Glu Ile
```

-continued

```
            3080             3085              3090

Asp Ile Ala Val Asp Lys Lys Gly Arg Ile Val Asp Asn Arg
    3095             3100              3105

His Met Thr Ser Arg Glu Gly Val Phe Ala Ala Gly Asp Val Val
    3110             3115              3120

Leu Gly Pro Ser Lys Val Gly Lys Ala Val Lys Asp Gly Leu Tyr
    3125             3130              3135

Ala Ala Glu Ala Met His Met Trp Leu Met Gly Arg Met Thr Arg
    3140             3145              3150

Arg Ile Leu His Val Asp Tyr Ser Leu Cys Ile Gly Cys Glu Thr
    3155             3160              3165

Cys Glu Ala Val Cys Asp Phe Leu His Gly Gly Lys Pro Asn Ile
    3170             3175              3180

Arg Ile Tyr Tyr Thr Val Thr Gly Leu Pro Ile Pro Ile Asn Cys
    3185             3190              3195

Arg His Cys Glu Arg Ala Pro Cys Met Asp Val Cys Pro Ala Gly
    3200             3205              3210

Ala Ile Tyr Arg Asp Ser Asp Gly Ala Ile Ile Asn Pro Asp
    3215             3220              3225

Lys Cys Ile Gly Cys Tyr Met Cys Leu Ala Val Cys Pro Phe Gly
    3230             3235              3240

Val Pro Ser Phe Asp Val Lys Thr Lys Ala Val Thr Lys Cys Asp
    3245             3250              3255

Met Cys Ala Asp Arg Arg Arg Leu Gly Met Glu Pro Ala Cys Ala
    3260             3265              3270

Glu Met Cys Pro Ala Glu Ala Ile Phe Phe Gly Lys Pro Glu Glu
    3275             3280              3285

Val Glu Asp Arg Ile Arg Arg Thr Ala Glu Arg Ile Ala Arg
    3290             3295              3300

Glu Arg Ile Ala Ala Val Asp Met Glu Gly Val Gly Arg Met Leu
    3305             3310              3315

Met Leu Trp Glu Ser Gln Ile Pro Ile Asn Gln Val Phe Glu Leu
    3320             3325              3330

Arg Cys Arg Ser Met Thr Tyr Phe Gly Val Gly Ala Ile Asn Lys
    3335             3340              3345

Phe Tyr Asp Ile Ala Lys Asp Leu Lys Glu Asn Arg Gly Ile Thr
    3350             3355              3360

Lys Val Ile Leu Val Thr Gly Lys Ser Ser Tyr Lys Lys Cys Gly
    3365             3370              3375

Ala Trp Asp Val Val Lys Pro Ala Leu Glu Glu Tyr Gly Ile Glu
    3380             3385              3390

Tyr Val His Tyr Asp Lys Val Gly Pro Asn Pro Thr Val Asp Met
    3395             3400              3405

Ile Asp Glu Ala Thr Gln Leu Gly Lys Glu Phe Gly Ala Gln Ala
    3410             3415              3420

Val Ile Gly Ile Gly Gly Gly Ser Pro Ile Asp Ser Ala Lys Ser
    3425             3430              3435

Val Ala Ile Leu Leu Glu Tyr Thr Asp Lys Thr Ala Arg Asp Leu
    3440             3445              3450

Tyr Glu Leu Lys Phe Thr Pro Thr Lys Ala Lys Pro Ile Ile Ala
    3455             3460              3465

Val Asn Thr Thr His Gly Thr Gly Thr Glu Val Asp Arg Phe Ala
    3470             3475              3480
```

Val Ala Ser Ile Pro Glu Lys Glu Tyr Lys Pro Ala Ile Ala Tyr
    3485                3490                3495

Asp Cys Ile Tyr Pro Leu Tyr Ser Ile Asp Asp Pro Ala Leu Met
3500                3505                3510

Thr Lys Leu Pro Ala Asp Gln Thr Arg Tyr Val Thr Ile Asp Ala
    3515                3520                3525

Leu Asn His Ile Thr Glu Ala Ala Thr Thr Lys Phe Ala Ser Pro
3530                3535                3540

Tyr Ser Ile Leu Leu Ala Gln Glu Thr Ala Arg Leu Ile Phe Asp
    3545                3550                3555

Tyr Leu Pro Glu Ala Leu Ala His Pro Asp Asn Leu Gln Ala Arg
3560                3565                3570

Tyr Tyr Leu Leu Tyr Ala Ser Ala Ile Ala Gly Ile Ser Phe Asp
    3575                3580                3585

Asn Gly Leu Leu His Phe Thr His Ala Leu Glu His Pro Leu Ser
3590                3595                3600

Ala Val Lys Pro Asp Leu Pro His Gly Leu Gly Leu Ala Met Leu
    3605                3610                3615

Leu Pro Ala Val Ile Lys His Ile Tyr Pro Ala Thr Ala Arg Ile
3620                3625                3630

Leu Ala Glu Val Tyr Arg Pro Leu Val Pro Glu Ala Lys Gly Val
    3635                3640                3645

Pro Gly Glu Ala Glu Leu Val Ala Lys Lys Val Glu Glu Trp Leu
3650                3655                3660

Phe Asn Ile Gly Ile Thr Gln Lys Leu Ile Asp Val Gly Phe Thr
    3665                3670                3675

Glu Glu Asp Val Asp Lys Leu Ala Glu Leu Ala Met Thr Thr Pro
3680                3685                3690

Ser Leu Asp Leu Leu Leu Ser Leu Ala Pro Ile Glu Ala Thr Lys
    3695                3700                3705

Glu Thr Val Ala Ala Ile Tyr Arg Asp Ser Leu Tyr Pro Leu Asn
    3710                3715                3720

Lys

<210> SEQ ID NO 5
<211> LENGTH: 1658
<212> TYPE: PRT
<213> ORGANISM: Thermococcus onnurineus NA1

<400> SEQUENCE: 5

Met Glu Val Ile Phe Leu Phe Ile Val Ile Leu Ser Val Ala Ser
1               5                   10                  15

Phe Ile Gly Val Phe Ser Arg Ser Ala Ile Leu Thr Lys Leu Val Asn
            20                  25                  30

Ala Leu Ser Ala Leu Gly Ser Leu Thr Ile Ala Tyr Ala Gly Ile Val
        35                  40                  45

Gly Leu Lys Glu Ser Val Glu Leu Asn Ile Thr Leu Leu His Leu Lys
    50                  55                  60

Ser Asp Ser Ile Ile Asn Ala Phe Ser Thr Leu Thr Leu Lys Val Asp
65                  70                  75                  80

Pro Leu Ser Gly Phe Phe Met Ile Ile Leu Gly Ile Leu Gly Phe Cys
                85                  90                  95

Thr Ser Val Tyr Gly Ile Ala Tyr Leu Asp Met Tyr Lys Gly Asp Lys
                100                 105                 110

```
Arg Leu Tyr Ala Phe Asn Tyr Pro Leu Phe Leu Phe Met Phe Leu
            115                 120                 125
Val Leu Val Ser Trp Asn Leu Leu Trp Phe Val Val Phe Trp Glu Leu
130                 135                 140
Met Thr Leu Phe Ser Gln Phe Leu Val Ala Phe Glu Arg Asn Glu Lys
145                 150                 155                 160
Thr Leu Ile Ala Thr Leu Lys Tyr Phe Cys Met Thr Lys Ala Ala Ala
                165                 170                 175
Asp Phe Met Leu Ile Ala Ile Val Leu Val Leu Ile Thr Ile Ser Gly
            180                 185                 190
Gly Gly Asp Tyr Asp Ile Leu Ser Ser Gln Leu Val Asn Tyr Phe Arg
        195                 200                 205
Ser His Pro Leu Glu Met Tyr Leu Val Ser Ala Gly Phe Met Ile Gly
    210                 215                 220
Leu Gly Val Lys Ala Ala Leu Val Pro Phe His Val Trp Leu Pro Asp
225                 230                 235                 240
Ala Tyr Val Glu Ala Pro Ser Asn Val Ser Ser Leu Leu Ser Gly Ala
                245                 250                 255
Met Glu Lys Met Pro Val Tyr Met Met Phe Arg Phe Phe Leu Ser Phe
            260                 265                 270
Thr Pro Leu Thr Pro Asn Ile Gly Leu Leu Ile Ala Leu Phe Gly Thr
        275                 280                 285
Leu Thr Leu Phe Phe Gly Thr Met Tyr Ala Leu Lys Gln Thr Asp Ser
    290                 295                 300
Lys Arg Leu Leu Ala Tyr His Ser Val Gly Gln Ile Gly Tyr Val Val
305                 310                 315                 320
Phe Ala Leu Gly Ala Gly Ile Tyr Leu Leu Ser Lys Gly Tyr Thr Thr
                325                 330                 335
Phe Gly Ala Leu Ala Leu Met Ala Ser Leu Phe His Ala Leu Asn His
            340                 345                 350
Ala Phe Phe Lys Gly Leu Leu Phe Leu Thr Ala Gly Ser Ile Leu Tyr
        355                 360                 365
Arg Thr Gly Ser Arg Asp Leu Asp His Leu Gly Gly Leu Ala Arg Phe
    370                 375                 380
Met Pro Ile Thr Ala Phe Ala Ala Leu Ile Gly Ser Leu Ser Ile Ala
385                 390                 395                 400
Gly Met Pro Pro Phe Asn Gly Phe Val Ser Lys Trp Met Ile Tyr Val
                405                 410                 415
Ser Thr Leu Pro Thr Pro Thr Leu Val Ser Leu Phe Gly Ala Leu Ala
            420                 425                 430
Leu Phe Ile Ser Ala Val Thr Thr Ala Ser Phe Val Lys Tyr Phe Thr
        435                 440                 445
Ser Ile Phe Val Arg Pro Pro Ala Lys Glu Ile Thr Val Lys Glu Val
    450                 455                 460
Pro Val Ser Met Trp Ala Ser Gln Leu Ile Leu Ala Val Leu Cys Val
465                 470                 475                 480
Ile Phe Gly Val Tyr Pro Ala Leu Pro Leu Glu Ala Ile Ser Lys Ala
                485                 490                 495
Val Asp Ser Val Gly Val Thr Thr Pro Ser Ile Thr Val Phe Pro Gly
            500                 505                 510
Leu Ile Val Ser Asp Gly Ile Gly Asn Ile Ala Pro Leu Ala Leu Leu
        515                 520                 525
```

-continued

```
Val Phe Ser Gly Ala Leu Thr Ala Val Leu Ala Ile Phe Pro Tyr
            530                 535                 540
Lys Ile Ser Leu Pro Val Trp Thr Thr Gly Thr Arg Ser Leu Ala
545                 550                 555                 560
Met Arg Leu Pro Ala Ser Ser Tyr Tyr Ala Ser Phe Glu Glu Phe
                565                 570                 575
Glu Asp Val Tyr Ser Trp Gly Glu Trp Cys Val Cys Thr Thr Lys Arg
            580                 585                 590
Leu Trp Asp Ala Thr Lys Ala Val Leu Ser Asn Phe Glu Glu Val Ser
            595                 600                 605
Phe Asp Leu Asp Lys Met Met Thr Gly Ala Trp Leu Met Leu Leu Ile
            610                 615                 620
Leu Leu Thr Ile Leu Gly Gly Val Leu Leu Met Asn Ala Val Tyr Ala
625                 630                 635                 640
Ala Leu Asn Leu Ile Phe Ile Val Leu Phe Ala Pro Leu Leu Asp Gly
                645                 650                 655
Ile Glu Arg Lys Val Lys Ala Arg Leu Gln Ser Arg Gln Gly Pro Pro
                660                 665                 670
Leu Ile Gln Thr Trp Leu Asp Leu Leu Lys Leu Phe Arg Arg Pro Asn
                675                 680                 685
Val Arg Pro Arg Glu Ser Val Arg Trp Leu Phe Glu Pro Ala Pro Ala
690                 695                 700
Ile Ala Leu Val Ser Val Leu Ala Ala Ser Leu Phe Ile Pro Ser Leu
705                 710                 715                 720
Leu Pro Gly Ser Leu Asp Thr Trp Gly Asp Ile Ile Ala Phe Ile Tyr
                725                 730                 735
Leu Ser Thr Leu Ser Ala Val Ala Ile Ala Leu Gly Ala Phe Ser Thr
                740                 745                 750
Gly Ser Pro Tyr Ala Gln Ile Gly Ser His Arg Glu Val Ser Ile Ile
            755                 760                 765
Met Ala Glu Glu Phe Ser Leu Ala Phe Ile Val Ala Ala Leu Ala Ala
770                 775                 780
Ser Ser Gly Gly Leu Ser Phe Ser Arg Leu Phe Pro Leu Gln Leu Lys
785                 790                 795                 800
Val Ser Thr Ile Thr Gly Ala Leu Ala Phe Ala Val Met Ala Tyr Val
                805                 810                 815
Ala Gly Ala Arg Ile Pro Phe Asp Val Ala Glu Ala Glu Pro Glu Ile
            820                 825                 830
Val Glu Gly Pro Phe Ile Glu Phe Ser Gly Lys Gly Leu Gly Met Leu
            835                 840                 845
Lys Leu Ser Ile Tyr Val Lys Arg Leu Leu Leu Thr Thr Ile Leu Leu
850                 855                 860
Asn Phe Phe Leu Pro Gln Asp Gly Thr Val Arg Val Leu Val Tyr Val
865                 870                 875                 880
Ile Gly Leu Val Ile Ser Val Tyr Ala Ser Ile Glu Ala His
                885                 890                 895
Tyr Gly Arg Phe Arg Thr Lys Asp Ala Ala Arg Phe Leu Lys Arg Phe
            900                 905                 910
Ala Ile Val Gly Ile Leu Ser Trp Ile Leu Gly Val Val Gly Trp Met
                915                 920                 925
Val Phe Asp Ile Leu Lys Gly Cys Lys Ile Leu Glu His Asn Asp Lys
            930                 935                 940
Met Thr Val Ala Glu Val Gly Ala Ser Asn Ile Arg Glu Ile Ala Arg
```

```
                945                 950                 955                 960
        Ala Leu Phe Glu Arg Gly Tyr Tyr Ser Ser Gly Met Gly Val Asp
                        965                 970                 975
        Glu Arg Pro Ile Asn Gly Arg Phe Ala Met Tyr His Ile Phe Asn Cys
                        980                 985                 990
        Asp Thr Glu Gly Arg Tyr Val Val Leu Lys Ile Thr Ser Pro Glu Gly
                        995                1000                1005
        Ser Pro Glu Val Pro Ser Ile Thr Pro Val Ile Lys Gly Ala Glu
                1010                1015                1020
        Trp Ser Glu Arg Glu Ala Met Asp Met Leu Gly Ile Val Phe Ser
                1025                1030                1035
        Gly His Pro Lys Pro Glu Arg Leu Ile Leu Pro Asp Asp Trp Pro
                1040                1045                1050
        Glu Gly Val Tyr Pro Leu Arg Lys Asp Phe Pro Tyr Asn Lys Lys
                1055                1060                1065
        Leu Pro Pro Ser Lys Pro Ile Glu Lys Glu Arg Glu His Lys Lys
                1070                1075                1080
        Asp Val Met Glu Ile Pro Leu Gly Pro Tyr His Pro Ser Leu His
                1085                1090                1095
        Glu Pro Glu Tyr Phe Glu Leu Tyr Val Lys Gly Asp Lys Val Val
                1100                1105                1110
        Asp Ala Glu Tyr Arg Gly Phe His Ile His Arg Gly Met Glu Lys
                1115                1120                1125
        Leu Ala Glu Ser Arg Met Thr Ile Asn Gln Ile Pro Phe Leu Ala
                1130                1135                1140
        Glu Arg Ile Cys Gly Ile Cys Gly Cys Thr His Ser Ala Ala Tyr
                1145                1150                1155
        Cys Gln Ala Val Glu Asp Ala Ala Gly Ile Tyr Val Pro Glu Arg
                1160                1165                1170
        Ala Gln Tyr Ile Arg Thr Ile Met Leu Glu Val Glu Arg Ile His
                1175                1180                1185
        Ser His Leu Leu Trp Phe Gly Val Val Cys His Leu Leu Gly Phe
                1190                1195                1200
        Asp Ser Gly Phe Met His Ile Trp Arg Ala Arg Glu Tyr Ile Met
                1205                1210                1215
        Asp Ile Ala Glu Leu Ile Thr Gly Asn Arg Lys Thr Tyr Gly Ile
                1220                1225                1230
        Asn Ile Val Gly Gly Val Arg Arg Asp Ile Thr Glu Asp Lys Lys
                1235                1240                1245
        Glu Lys Thr Leu Lys Leu Leu Asp Met Val Glu Lys Glu Ser Arg
                1250                1255                1260
        Glu Val Leu Asp Asn Ile Ala Glu Met Lys Glu Leu Arg Glu Arg
                1265                1270                1275
        Met Glu Gly Val Gly Val Leu Pro Lys Lys Glu Ala Arg Glu Ile
                1280                1285                1290
        Gly Val Val Gly Pro Met Ala Arg Ser Ser Gly Ile Asp Thr Asp
                1295                1300                1305
        Val Arg Arg Asp His Pro Tyr Ala Ala Tyr Lys Asp Leu Asp Phe
                1310                1315                1320
        Lys Val Pro Val Tyr Lys Glu Gly Asp Val Phe Ala Arg Phe Leu
                1325                1330                1335
        Val Arg Tyr Glu Glu Ile Phe Glu Ser Phe Asn Met Ile Arg Gln
                1340                1345                1350
```

| Ala | Leu | Glu | Asn | Met | Pro | Pro | Gly | Glu | Leu | Ile | Asn | Asp | Glu | Tyr |
| | 1355 | | | | 1360 | | | | 1365 | | | | | |

Glu Ile Pro Pro Phe Lys Leu Gly Ile Gly Val Thr Glu Ala Pro
1370          1375              1380

Arg Gly Glu Asn Ile His Ala Val Ile Thr Trp Gly Glu Asn Met
1385          1390              1395

Ile Tyr Arg Trp His Pro Arg Ala Ala Thr Tyr Asn Asn Leu Pro
1400          1405              1410

Ala Val Pro Ile Met Leu Arg Gly Asn Asp Val Ala Asp Ala Pro
1415          1420              1425

Leu Ile Ile Ala Ser Ile Asp Pro Cys Phe Ser Cys Thr Asp His
1430          1435              1440

Val Ser Ile Ile Asp Ser Glu Ser Gly Lys Ile Leu Trp Arg Gly
1445          1450              1455

Pro Leu Lys Glu Gly Val Arg Arg Val Met Val Lys Asn Ser Leu
1460          1465              1470

Trp Val Phe His Leu Asn Ser Gly Ser Cys Asn Gly Cys Asp Ile
1475          1480              1485

Glu Ile Leu Asn Ile Phe Ala Pro Arg Asn Asp Val Glu Arg Leu
1490          1495              1500

Gly Ile Lys Leu Val Gly Ser Pro Arg His Ala Asp Ala Ile Ala
1505          1510              1515

Phe Thr Gly Pro Ile Thr Arg Glu Cys Leu Pro Lys Val Ile Asp
1520          1525              1530

Ala Leu Lys Ala Val Pro Glu Pro Lys Val Val Leu Ala Ile Gly
1535          1540              1545

Ala Cys Ala Cys Gly Gly Gly Ile Trp Tyr Asp Thr Tyr Ser Val
1550          1555              1560

Ile Gly Gly Val Lys Glu Leu Tyr Arg Ile Leu Lys Glu Glu Tyr
1565          1570              1575

Asn Met Glu Pro Pro Ala Thr Val Phe Ile Pro Gly Cys Pro Pro
1580          1585              1590

Lys Pro Glu Ala Ile Ile Tyr Gly Val Ala Val Ala Ser Gly Met
1595          1600              1605

Leu Glu Ser Lys Gln Lys Lys Thr Val Tyr Val Glu Pro Glu Glu
1610          1615              1620

Ser Val Ala Asn Glu Lys Leu Met Ile Ala Glu Leu Ile Ser Glu
1625          1630              1635

Thr Glu Lys Thr Arg His Phe Met Pro Gly Ile Val Ile Arg Gly
1640          1645              1650

Val Glu Asp Glu Pro
1655

<210> SEQ ID NO 6
<211> LENGTH: 1145
<212> TYPE: PRT
<213> ORGANISM: Thermococcus onnurineus NA1

<400> SEQUENCE: 6

Leu Ser Glu Ile Thr Leu Asn Lys Val Cys Arg Ile Ala Gly Glu Ala
1               5                   10                  15

Lys Leu Val Leu Tyr Glu Glu Asn Gly Thr Val Gln Asp Ala Leu Phe
            20                  25                  30

Ile Ala Thr Ala Pro Ile Arg Gly Phe Glu Lys Leu Val Val Gly Lys

```
                35                  40                  45
Asn Pro Leu Phe Ala Val Glu Ala Val Met Arg Ile Cys Gly Leu Cys
 50                  55                  60

His Ala Ser His Gly Ile Ala Met Ser Glu Ala Ile Glu Asn Ala Ile
 65                  70                  75                  80

Gly Ile Ile Pro Pro Arg Asn Gly Ile Leu Met Arg Glu Ala Leu Gly
                 85                  90                  95

Leu Val Asn Arg Ile Gln Ser His Met Leu Glu Phe Leu Met Val Ala
                100                 105                 110

Gly Asp Leu Leu Ile Glu Glu Lys Arg Glu Glu Val Leu Phe Gln Leu
                115                 120                 125

Met Asp Phe His Ala Lys Ile Ser Asp Tyr Leu Leu Lys Met Gly Gly
                130                 135                 140

Ala Ala Thr His Pro Pro Asn Leu Thr Val Gly Gly Met Phe Ser Val
145                 150                 155                 160

Pro Lys Trp Ser Val Phe Asn Asn Leu Lys Ala Arg Leu Pro Lys Leu
                165                 170                 175

Thr Gly Gln Trp Glu Glu Ile Ala His Leu Leu Thr Asp Glu Asp Ile
                180                 185                 190

Gln Thr Glu Val Ala Asp Glu Leu Arg Glu Lys Lys Ala Glu Asn Asn
                195                 200                 205

Tyr Leu Val Ser Ser Leu Phe Tyr Gly Asp Arg Phe Asn Ile Asn Ala
                210                 215                 220

Glu Arg Ile Glu Thr Met Pro Tyr Tyr Glu Tyr Arg Lys Asp Asn Pro
225                 230                 235                 240

His Ser Lys Glu Ser Thr Thr Leu Ile Ala Phe Tyr Gly Gly Glu Lys
                245                 250                 255

Val Glu Ala Gly Pro Arg Ala Arg Met Lys Val Tyr Arg Glu Phe Thr
                260                 265                 270

Asp Ser Ser Leu Tyr Gly Leu His Thr Ala Arg Val Gln Asp Thr Thr
                275                 280                 285

Leu Ala Leu Ile Arg Leu Glu Glu Ile Leu Asp Ser Ile Lys Met Asp
                290                 295                 300

Glu Pro Phe Arg Thr Lys Asn Ile Val Phe Gly Pro Gly Lys Gly Val
305                 310                 315                 320

Gly Val Tyr Glu Ala Pro Arg Gly Thr Leu Ile His Leu Ile Glu Leu
                325                 330                 335

Gly Asp Glu Gly Arg Val Val Ser Ser Lys Ile Ile Val Pro Thr Met
                340                 345                 350

Phe Asn Ile Pro Val Met Glu Glu Met Ala Lys Gly Leu Ser Val Lys
                355                 360                 365

Ala Ala Glu Ala Val Met Arg Leu Tyr Asp Pro Cys Ile Pro Cys Thr
                370                 375                 380

Thr His Val Val Arg Leu Gly Gly Met Glu Lys Leu Lys Val Leu His
385                 390                 395                 400

Val Asp Val Gly Gly Cys Glu Gly Cys Asn Val Ser Ile Ile Arg Ala
                405                 410                 415

Tyr Pro Lys Leu Met Asp Leu Ile Glu Leu Asp Ile Ser Tyr Leu Arg
                420                 425                 430

Lys Asp Glu Cys Lys Leu Asp Glu Tyr Asp Val Ala Ile Ile Thr Gly
                435                 440                 445

Gly Ala Cys Met Asn Glu Pro Arg Ile Leu Glu Glu Leu Lys Glu Ile
450                 455                 460
```

```
Arg Glu Lys Ala His Thr Val Val Ala Phe Gly Ser Cys Ala Thr Phe
465                 470                 475                 480

Ser Gly Ile Leu Arg Phe Cys Arg Gly Gly Gln Glu Pro Arg Pro Asp
                485                 490                 495

His Arg Asn Phe Gln Pro Ile Asn Ser Val Ile Lys Val Asp Tyr Ser
            500                 505                 510

Ile Pro Gly Cys Pro Pro Thr Pro Gln Met Leu Gln Ser Phe Phe Lys
        515                 520                 525

Phe Tyr Ile Asn Gly Asp Glu Arg Arg Leu Arg Leu Phe Lys Val Ser
    530                 535                 540

Ala Asp Ile Lys Lys Leu Ser Gly Phe Asp Leu Ile Asp Asp Ile Val
545                 550                 555                 560

Leu Thr Gly Leu Cys Ile Gly Cys Gly Ala Cys Glu Leu Ser Cys Pro
                565                 570                 575

Thr Asn Ala Ile Lys Leu Ile Asp Lys Arg Pro Asn Leu Val Gln Glu
            580                 585                 590

Lys Cys Ile Arg Cys Gly Thr Cys Tyr Ile Arg Cys Pro Arg Ala Ser
        595                 600                 605

Gln Ile Leu Ser Met Gly Gly Ala Arg Met Met Ser Val Ser Glu Asn
    610                 615                 620

Leu Leu Gly Asn Val Phe Gly Ile Tyr Leu Ala Arg Ala Thr Asp Glu
625                 630                 635                 640

Glu Ile Leu Lys Arg Lys Val Ala Ser Gly Gly Ala Val Thr Ala Leu
                645                 650                 655

Leu Ala Tyr Ala Leu Glu Lys Gly Leu Ile Asp Gly Val Val Thr Ala
            660                 665                 670

Lys Arg Thr Glu Gly Leu Glu Gly Gln Ala Val Val Ala Arg Thr Arg
        675                 680                 685

Glu Glu Leu Leu Glu Thr Ala Gly Asn Lys Trp Ser Ile Val Pro Phe
    690                 695                 700

Ala Ser Arg Met Lys Ala Lys Ile Glu Glu Glu Asp Leu Lys Asn Val
705                 710                 715                 720

Ala Val Val Cys Leu Pro Cys Gln Ala Gln Phe Phe Gly Gln Met Arg
                725                 730                 735

Asp Phe Pro Leu Leu Glu Ser Asp Phe Gly Glu Arg Ile Lys Tyr Ile
            740                 745                 750

Val Ser Leu Phe Cys Ile Gly Thr Phe Ala Phe Glu Ala Phe Leu Asn
        755                 760                 765

Tyr Leu Arg Met Lys His Gly Ile Met Ala Gln Asp Ile Lys Asp Ile
    770                 775                 780

Val Leu Lys Gly Asp Phe Leu Glu Ile Tyr His Gly Asp Ser Val Leu
785                 790                 795                 800

Ser Leu Pro Ile Lys Glu Val Tyr Ser Tyr Leu Gln Ala Gly Cys Leu
                805                 810                 815

Val Cys Thr Asp Tyr Thr Gly Thr Trp Ser Asp Ile Ser Ala Gly Phe
            820                 825                 830

Val Glu Ser Glu Arg Gly Trp Thr Val Leu Ile Thr Arg Asn Leu Lys
        835                 840                 845

Ala Glu Glu Leu Val Lys Ser Ala Glu Lys Asp Gly Tyr Ile Glu Leu
    850                 855                 860

Arg Asp Gly Ser His Val Met Gly Glu Val Leu Lys Ala Ala Arg Glu
865                 870                 875                 880
```

```
Lys Leu Ala Arg Ala Gln Lys Asn Met Met Tyr Leu Leu Ile Lys
                885                 890                 895

Lys Val Lys Ile Leu Lys Trp Gln Asp Gly Leu Val Pro Thr Glu Asp
            900                 905                 910

Tyr Ile Cys Val Glu Glu Thr Phe Glu Ile Phe Ala Val His Glu Lys
        915                 920                 925

Asp Glu Glu Phe Leu Ala Glu Leu Pro Ala Ser Pro Asn Gln Leu Lys
    930                 935                 940

Glu Leu Gly Ala Gly Phe Val Val Cys Gly Tyr Glu Arg Pro Glu
945                 950                 955                 960

Asp Ile Val Asp Val Trp Val Glu Gly Lys Glu Ile Tyr Val Lys Leu
                965                 970                 975

Lys Asp Thr Pro Ala Thr Gly Glu Leu Val Val Lys His Thr Pro Cys
            980                 985                 990

Gly Asp Pro Tyr Arg Met Lys Glu  Gly Arg Ile Leu Ser  Arg Lys Gly
        995                 1000                1005

Glu Glu  Val Lys Ile Thr Pro  Gly Leu Val Leu Lys  Ile Ser Ser
    1010                1015                1020

Thr Met  Thr Thr Leu Ala Glu  Thr Trp Arg Lys Thr  Gly Gly Thr
    1025                1030                1035

His Trp  Ala Ala Leu Phe Asp  Leu Asn Ala Asn Val  Val Ala Phe
    1040                1045                1050

Ser Glu  Asp Ile Gly Arg His  Asn Ala Val Asp Lys  Val Val Gly
    1055                1060                1065

Tyr Ala  Val Leu Asn Gly Leu  Asp Leu Glu Arg Leu  Ile Leu Ala
    1070                1075                1080

Ser Ser  Gly Arg Met Pro Tyr  Gly Met Val Arg Lys  Ala Val Asn
    1085                1090                1095

Ala Gly  Ile Pro Val Val Val  Thr Lys Ser Pro Pro  Thr Asp Lys
    1100                1105                1110

Gly Val  Glu Leu Ala Arg Glu  His Gly Val Thr Leu  Ile Gly Phe
    1115                1120                1125

Ala Arg  Gly Arg Arg Phe Asn  Val Tyr Ser Gly Glu  His Arg Leu
    1130                1135                1140

Leu Phe
    1145

<210> SEQ ID NO 7
<211> LENGTH: 2903
<212> TYPE: PRT
<213> ORGANISM: Thermococcus onnurineus NA1

<400> SEQUENCE: 7

Met Glu Glu Leu Phe Ile Leu Ser Phe Ser Ile Pro Leu Val Gly Gly
1               5                   10                  15

Leu Leu Leu Phe Lys Leu Asp Gly Lys Arg Ala Asp Tyr Phe Met Leu
                20                  25                  30

Ile Thr Val Ile Leu Ala Thr Ile Leu Asn Leu Ala Gly Val Tyr Glu
            35                  40                  45

Phe Tyr Ser Ser Gly Met Pro Thr Ile His Lys Thr Leu Val Ser Ser
        50                  55                  60

Thr Thr Leu Gly Glu Val Tyr Gly Leu Leu Ile Asp Pro Met Ser Val
65                  70                  75                  80

Cys Val Gly Leu Val Val Ile Thr Ala Gly Leu Leu Phe Met Ile Tyr
                85                  90                  95
```

```
Ala Lys Asp Tyr Met Ser Pro Glu Asn Lys Glu His Pro Val Tyr Glu
            100                 105                 110

Asp Lys Gly Arg Phe Tyr Ala Trp Met Val Leu Phe Ile Gly Ala Thr
            115                 120                 125

Leu Ala Phe Ile Tyr Ser Ser Val Leu Gln Leu Leu Ile Phe Phe
        130                 135                 140

Glu Ile Met Ser Leu Ala Cys Trp Gly Val Ala Gly Tyr Tyr Gly Ser
145                 150                 155                 160

Lys Lys Ala Lys Arg Ala Ala Tyr Lys Ala Leu Leu Val Thr Asn Phe
                165                 170                 175

Gly Ala Val Ile Gly Leu Tyr Thr Ala Val Gly Ile Gly Ile Thr His
            180                 185                 190

Leu His Asp Leu Ser Ile Phe Ala Tyr Ser Gly Leu Asn Asp Ser Leu
        195                 200                 205

Lys Leu Val Val Phe Ile Gly Val Met Ile Ala Ala Phe Thr Lys Ser
    210                 215                 220

Ala Gln Phe Pro Leu Tyr Ser Trp Leu Pro Asp Ala Met Val Ala Pro
225                 230                 235                 240

Thr Pro Ala Ser Ala Phe Leu His Gly Ala Ala Met Val Glu Met Gly
            245                 250                 255

Val Tyr Leu Leu Ala Arg Phe Ile Gln Phe Met Asn Pro Ile Pro Lys
        260                 265                 270

Glu Gly Phe Tyr Val Met Ala Ala Leu Ile Ile Ala Thr Gln Ile Ile
        275                 280                 285

Cys Ile Leu Met Tyr Pro Leu Gln Lys Ser Ala Lys Arg Leu Leu Ala
    290                 295                 300

Tyr Ser Thr Ile Ala Glu Ser Gly Leu Met Tyr Val Ala Leu Ala Thr
305                 310                 315                 320

Ala Val Leu Gly Leu Gln Gly Gly Leu Gln Ala Ser Met Phe Gln Leu
            325                 330                 335

Phe Asn His Ala Tyr Ile Lys Gly Leu Ala Phe Leu Thr Ala Gly Thr
        340                 345                 350

Phe Ser Tyr Ala Leu Gly Thr Leu Glu Met Asp Arg Ile Lys Gly Leu
        355                 360                 365

Ile Lys Ser Pro Val Val Gly Tyr Ser Trp Thr Phe Ala Leu Leu Gly
    370                 375                 380

Leu Ala Gly Val Pro Pro Phe Gly Val Phe Phe Gly Lys Leu Gly Ile
385                 390                 395                 400

Leu Ser Asn Ala Lys Ala Met Glu Glu Ser Val Leu Ile Ile Ala Met
            405                 410                 415

Phe Val Leu Leu Leu Asp Ser Ala Val Phe Leu Met Val Ser Leu
        420                 425                 430

Lys Arg Ile His Gly Met Val Phe Ser Glu Gly Gly Glu Glu Val Glu
    435                 440                 445

Ile Thr Pro Leu Met Lys Ala Val Met Val Ile Leu Leu Val Leu Ala
        450                 455                 460

Met Leu Ala Pro Tyr Ile Ala Tyr Pro Leu Ile Val Lys Val Gly Trp
465                 470                 475                 480

Met Phe Asp Val Thr Leu Thr Leu Ser Leu Asp Arg Thr Ala Val Phe
                485                 490                 495

Phe Val Leu Asn Val Ala Ile Leu Gly Ile Ala Ala Leu Val Ala Ser
            500                 505                 510
```

-continued

Phe Arg Tyr Met Arg Ile Tyr Glu Phe Lys Pro Lys Ile Pro Tyr Tyr
             515                 520                 525

Pro Thr Leu Ala Ile Phe Ile Val Ser Met Leu Leu Ile Pro Met Val
         530                 535                 540

Gln Asp Trp Leu Ser Phe Leu Phe Leu Trp Glu Ile Met Thr Leu Ala
545                 550                 555                 560

Ser Tyr Phe Leu Ile Ile Tyr Asp Trp Pro Glu Ser Val Lys Lys
                 565                 570                 575

Ala Gly Trp Lys Tyr Phe Val Thr Met His Leu Phe Asp Thr Ser Pro
             580                 585                 590

Leu Met Leu Ala Val Thr Met Tyr Tyr Ala Phe His Gly Thr Phe Asn
         595                 600                 605

Phe Gly Ala Ile Thr Glu Tyr Ser Asn Ala Ile Val Ala Leu Phe Leu
         610                 615                 620

Leu Gly Phe Ala Ala Lys Ala Gly Leu Phe Pro Leu His Phe Trp Leu
625                 630                 635                 640

Pro Asp Ala His Pro Ala Ala Pro Ser Pro Val Ser Ala Leu Met Ser
                 645                 650                 655

Gly Ala Met Val Glu Leu Gly Leu Tyr Gly Thr Ile Arg Val Leu Asn
             660                 665                 670

Ala Val Gly Trp Ser Val Ala Thr Trp Ile Val Tyr Leu Ile Gly Ala
         675                 680                 685

Met Ala Val Leu Ser Met Leu Ala Ala Ile Phe Ser Tyr Ala Leu Gln
         690                 695                 700

Asp Asp Val Lys Arg Leu Phe Ala Trp Ser Thr Ile Asp Asn Met Gly
705                 710                 715                 720

Trp Met Tyr Leu Leu Ile Leu Ala Gly Leu Leu Gly Val Ser Gly Val
                 725                 730                 735

Glu Lys Gly Val Asp Tyr Tyr Val Val Ala His Gly Leu Ala Lys Ala
             740                 745                 750

Ala Ala Phe Ile Ser Thr Gly Ala Leu Leu Tyr Val Phe Gly Thr Arg
         755                 760                 765

Ser Leu Lys Lys Ala Lys Gly Met Met Asn Thr Asp Ser Leu Thr Ala
770                 775                 780

Gly Leu Met Met Ala Ser Ile Phe Ala Leu Glu Gly Val Pro Pro Phe
785                 790                 795                 800

Asn Leu Phe Met Asn Lys Leu Asn Val Ile Lys Thr Leu Leu Thr Val
                 805                 810                 815

Ser Pro Ala Leu Ala Tyr Phe Thr Ala Leu Glu Trp Val Ile Ala Phe
             820                 825                 830

Ile Leu Phe Leu Arg Val Val His Ala Tyr Ile Leu Ser Glu Gly Glu
         835                 840                 845

Pro Glu Ala Lys Arg Lys Leu Ala Gly Ser Ile Ala Leu Ser Val Ile
850                 855                 860

Val Leu Leu Ile Leu Ser Met Val Ser Gln Phe Val Cys Asp Tyr Ile
865                 870                 875                 880

Trp Val Arg Trp Met Glu Gly Leu Phe Thr Leu Ala Val Ile Leu Tyr
                 885                 890                 895

Phe Leu Ser Ile Pro Ala Ala Leu Ala Leu Lys Arg Ser Phe Lys Ala
             900                 905                 910

Ser Ile Ser Ile Gly His Ile Leu Thr Ala Leu Ala Ser Ile Ala Leu
         915                 920                 925

Leu Ala Phe Thr Phe Val Ser Ile Pro Asp Ile Leu Ser Gly Lys Ala

```
                930             935             940
Ile Glu Phe Thr Tyr Asp Leu Gly Val Ala Gln Ile Pro Phe Gln Ile
945                 950             955                 960

Asp Gly Leu Ser Leu Ile Met Cys Phe Ile Phe Gly Ala Leu Gly Leu
            965             970             975

Ala Ala Ser Ile Tyr Ser Pro Arg Tyr Met Ala Ile Tyr Glu Lys Ser
        980             985             990

Gly Arg Gly Trp Met Tyr Ile Thr Ile Tyr Ser Val Phe Met Leu Ser
    995             1000            1005

Met Ile Leu Ile Val Thr Ile Ala Asn Met Phe Trp Phe Ile Phe
    1010            1015            1020

Leu Trp Glu Val Met Thr Phe Thr Ser Tyr Leu Leu Thr Ile Trp
    1025            1030            1035

Glu Ser Asp Lys Glu Asp Val Arg Lys Ala Gly Trp Lys Tyr Phe
    1040            1045            1050

Val Thr Met His Ile Val Ser Thr Leu Pro Leu Ile Ile Ala Leu
    1055            1060            1065

Ala Leu Leu Tyr Ala Asp Val Ser Ser Ile Glu Gly Leu Asn Phe
    1070            1075            1080

Glu Ser Leu Ala Ala Leu Lys Leu Ser Pro Val Phe Tyr Ala Leu
    1085            1090            1095

Phe Leu Ile Gly Phe Gly Ser Lys Ser Gly Val Val Pro Leu His
    1100            1105            1110

Phe Trp Ala Pro Glu Ala Tyr Thr Val Ala Pro Ser Asn Val Ser
    1115            1120            1125

Ala Leu Met Ala Gly Ala Leu Glu Lys Val Ala Val Tyr Ala Leu
    1130            1135            1140

Ile Arg Thr Thr Cys Phe Ile Met Lys Pro Asn Glu Thr Phe Gly
    1145            1150            1155

Tyr Ala Val Ala Leu Leu Gly Thr Val Thr Leu Thr Val Gly Thr
    1160            1165            1170

Leu Tyr Ala Leu Lys Gln Thr Asp Ala Lys Arg Leu Leu Ala Tyr
    1175            1180            1185

His Ser Ile Gly Gln Ile Gly Tyr Ile Trp Leu Gly Met Gly Val
    1190            1195            1200

Gly Ile Val Phe Ile Ala Arg Gly Asp Met Tyr Ser Ala Phe Gly
    1205            1210            1215

Ala Ile Ala Leu Ala Ser Ser Leu Tyr His Leu Val Asn His Thr
    1220            1225            1230

Phe Phe Lys Gly Leu Leu Phe Leu Ser Thr Gly Ser Ile Phe Tyr
    1235            1240            1245

Arg Thr Arg Ser Arg Asp Leu Asn Gln Leu Arg Gly Leu Ala Lys
    1250            1255            1260

Leu Met Pro Phe Thr Ala Leu Phe Thr Phe Ile Ala Ala Met Ser
    1265            1270            1275

Ile Ala Gly Thr Pro Pro Phe Asn Gly Phe Met Ser Lys Trp Met
    1280            1285            1290

Ile Tyr Gln Ser Thr Phe Leu Ser Gly Asn Gly Leu Ile Val Phe
    1295            1300            1305

Phe Gly Val Met Ala Leu Phe Ile Ser Ala Ala Thr Leu Ala Ser
    1310            1315            1320

Phe Ile Lys Phe Tyr Thr Thr Ala Phe Gly Gly Glu Pro Thr Glu
    1325            1330            1335
```

```
Phe Thr Lys Asp Ala Glu Glu Val Pro Ser Pro Met Leu Ile Ala
    1340                1345                1350

Lys Gly Phe Leu Ala Ser Leu Cys Ile Leu Leu Gly Leu Val Pro
    1355                1360                1365

Ser Leu Ile Leu Pro Ile Leu Leu Ser Pro Gly Ala Ala Leu Ala
    1370                1375                1380

Gly Ile Asp Val Ser Gly Leu Met Asp Thr Asn Tyr Trp Leu Val
    1385                1390                1395

Thr Ile Lys Ala Pro Leu Met Pro Thr Gly Ala Glu Ser Tyr Phe
    1400                1405                1410

Lys Pro Leu Leu Phe Ala Thr Leu Phe Gly Val Ile Phe Leu Gly
    1415                1420                1425

Met Tyr Leu Leu Phe Pro Ile Ser Lys Lys Thr Tyr Arg Pro Trp
    1430                1435                1440

Thr Leu Gly Glu Pro Val Ala Met Glu His Tyr Lys Phe Lys Ala
    1445                1450                1455

Ile Asn Tyr Tyr Glu Pro Phe Glu Glu Tyr Ile His Pro Leu Tyr
    1460                1465                1470

His Thr Gly His Val Leu Ser Glu Phe Gly Ser Ala Leu Ile Gly
    1475                1480                1485

Ala Val Ala Asn Ala Tyr Val Ser Thr Thr Arg Ala Leu His Arg
    1490                1495                1500

Val Cys Asp Ser Ile Ser Lys Ser Val Ala Gly Ile Gly Lys Glu
    1505                1510                1515

Tyr Glu Lys Lys Cys Pro Glu Val Tyr Leu Asp Glu Tyr Phe Leu
    1520                1525                1530

Ala Pro Leu Val Lys Ile Val Arg Val Ser Gly Val Leu Leu Asp
    1535                1540                1545

Glu Gly Phe Met Arg Pro Asn Ala Ala Phe Thr Ile Ala Leu Val
    1550                1555                1560

Thr Leu Ala Val Ile Leu Ala Leu Met Val Leu Met Thr Leu Glu
    1565                1570                1575

Lys Ile Ala Phe Ala Ala Leu Ser Leu Met Ile Ile Ile Leu Leu
    1580                1585                1590

Pro Pro Leu Leu Asp Gly Ile Ser Arg Lys Ile Lys Ala Thr Val
    1595                1600                1605

Gln Glu Arg Gln Gly Pro Pro Val Phe Gln Thr Tyr Tyr Asp Leu
    1610                1615                1620

Ser Ser Leu Leu Ser Met Glu Pro Ile Leu Pro Thr Asp Arg Leu
    1625                1630                1635

Gly Phe Leu Ile Ala Pro Tyr Val Ala Phe Ala Ser Ala Val Ser
    1640                1645                1650

Ala Ala Leu Leu Leu Pro Phe Gly Asn Phe Val Pro Val Ala Phe
    1655                1660                1665

Thr Gly Asp Ile Phe Val Phe Leu Tyr Val Leu Ala Ile Phe Ser
    1670                1675                1680

Ile Ser Met Met Met Ala Gly Phe Leu Val Asn Asn Thr Tyr Ser
    1685                1690                1695

Asn Ala Gly Ala Asn Arg Glu Met Met Leu Ile Leu Ser Val Glu
    1700                1705                1710

Pro Ile Leu Gly Ile Ala Ile Gly Ile Leu Ala Leu Lys Thr His
    1715                1720                1725
```

```
Ser Leu Ser Val Ser Gly Ile Pro Leu Asn Leu Ser Leu Thr Pro
    1730            1735            1740

Ser Val Val Leu Ala Phe Ile Phe Leu Ala Tyr Ala Val Tyr Thr
    1745            1750            1755

Glu Cys Ala Phe Ile Pro Phe Asp Ile Ala Glu Ala Glu Thr Glu
    1760            1765            1770

Ile Leu Glu Gly Pro Leu Val Glu Tyr Ser Gly Lys Leu Leu Gly
    1775            1780            1785

Ile Phe Lys Trp Ala Met Leu Ile Lys Arg Val Ala Leu Ile Trp
    1790            1795            1800

Leu Phe Ala Ser Phe Ile Val Ile Pro Val Met Lys Gly Phe Val
    1805            1810            1815

Asp Ile Thr Thr Pro Tyr Gly Gly Ala Val Thr Leu Ala Ala Gln
    1820            1825            1830

Leu Val Leu Leu Val Val Phe Tyr Val Met Ser Ala Ile Ile Glu
    1835            1840            1845

Ser Thr Thr Ala Arg Met Lys Val Ile Gln Ala Ile Arg Gln Asn
    1850            1855            1860

Thr Val Ile Phe Leu Ala Gly Ile Val Ala Leu Val Ile Ala Ser
    1865            1870            1875

Leu Gly Trp Met Ser Glu Val Ile Lys Phe Asn Glu Ala Leu Lys
    1880            1885            1890

Lys Lys Arg Val His Arg Gly Asp Glu Lys Ala Lys Val Thr Arg
    1895            1900            1905

Glu Tyr Leu Asp Glu Ile Ile Glu Lys Phe Gly Glu Lys Ile Arg
    1910            1915            1920

Asp Val Lys Gln Ala Ala Tyr Asn Gln Trp Ile Ile Thr Val Glu
    1925            1930            1935

Arg Glu Asp Leu Pro Glu Ile Val Leu Tyr Phe Leu Asn His Pro
    1940            1945            1950

Glu Trp Lys Glu Thr Gln Leu Ser Ser Met Val Ala Thr Asp Glu
    1955            1960            1965

Arg Pro Leu Asn Gly Lys Phe Ser Ile Thr Tyr Trp Leu Ser Val
    1970            1975            1980

Asn Gly Lys Ala Gly Asp Phe Tyr Leu Gly Val Arg Ala Tyr Leu
    1985            1990            1995

Pro Glu Asp Asp Pro Arg Phe Thr Ser Ile Ala Ala Lys His Arg
    2000            2005            2010

Gly Ala Asn Trp Tyr Glu Arg Glu Ala Met Glu Met Leu Gly Leu
    2015            2020            2025

Thr Ala Glu Gly His Pro Asp Pro Arg Arg Leu Val Leu Pro Asp
    2030            2035            2040

Asp Trp Pro Ser Cys Val Tyr Pro Leu Arg Lys Asp Phe His Tyr
    2045            2050            2055

Ser Asn Ser Pro Pro Gly Glu Lys Phe Tyr Pro Tyr Lys Glu Pro
    2060            2065            2070

Lys Lys Asp Glu Ile Val Val Pro Tyr Gly Pro Tyr His Val Ala
    2075            2080            2085

Leu Glu Glu Ala Ala His Phe Arg Leu Tyr Val Lys Gly Glu Thr
    2090            2095            2100

Ile Thr Asp Val Asp Tyr Arg Gly Phe Tyr Ala His Arg Gly Ile
    2105            2110            2115

Glu Lys Ile Ser Glu Gly Arg Leu Thr Tyr Asp Gln Val Cys Phe
```

```
                2120                2125                2130
Ile Ala Glu Arg Ile Cys Gly Ile Cys Gly Cys Thr His Ser Thr
            2135                2140                2145
Ala Tyr Cys Gln Ala Val Glu Asn Ala Gly Gly Ile Glu Val Pro
            2150                2155                2160
Glu Arg Ala Glu Tyr Ile Arg Thr Ile Val Leu Glu Ile Glu Arg
            2165                2170                2175
Leu His Ser His Leu Leu Asn Phe Gly Ile Val Ser His Leu Val
            2180                2185                2190
Gly Tyr Asp Tyr Gly Phe Met Lys Ala Trp Arg Ile Arg Glu His
            2195                2200                2205
Val Met Trp Leu Ala Glu Arg Leu Thr Gly Asn Arg Lys Thr Tyr
            2210                2215                2220
Gly Met Leu Leu Val Gly Val Arg Arg Asp Leu Leu Glu Tyr
            2225                2230                2235
Arg Lys Ser Leu Ile Glu Asp Val Leu Lys Ile Lys Thr Glu
            2240                2245                2250
Phe Ser Glu Leu Val Asp Glu Ala Ile Ser Thr Ser Thr Phe Val
            2255                2260                2265
Lys Arg Leu Glu Gly Val Gly Val Leu Pro Tyr Lys Val Ala Lys
            2270                2275                2280
Glu Trp Asp Val Asp Gly Pro Leu Gly Arg Gly Ser Gly Arg Asp
            2285                2290                2295
Phe Asp Val Arg Arg Asp His Pro Tyr Ala Ala Tyr Lys Tyr Leu
            2300                2305                2310
Asp Phe Lys Val Pro Val Tyr Lys Glu Gly Asp Val Leu Ala Arg
            2315                2320                2325
Ala Leu Val Arg Ile Glu Glu Val Phe Glu Ser Ile Trp Ile Ile
            2330                2335                2340
Glu Gln Ala Leu Asp Gln Met Pro Gly Gly Asp Ile Leu Ala Glu
            2345                2350                2355
Tyr Lys Glu Ile Pro Pro Tyr Ser Glu Ala Ile Gly Met Thr Glu
            2360                2365                2370
Ala Pro Arg Gly Glu Asn Ile His Tyr Val Met Thr Gly Glu Asn
            2375                2380                2385
Asn Lys Val Tyr Arg Tyr Arg Ala Arg Ala Ala Thr Tyr Asn Asn
            2390                2395                2400
Leu Pro Ala Val Pro Asp Met Met Arg Gly Tyr Thr Ile Ala Asp
            2405                2410                2415
Ala Pro Leu Ile Val Ala Ser Ile Asp Pro Cys Tyr Ser Cys Thr
            2420                2425                2430
Glu Arg Val Gln Val Val Asp Val Glu Ser Gly Lys Val Arg Val
            2435                2440                2445
Leu Ser Glu Thr Glu Phe Asn Lys Leu Ser Ile Lys Ala Ser Arg
            2450                2455                2460
Arg Val Met Ala Val Thr Leu Lys Tyr Pro Phe Val Lys Leu Glu
            2465                2470                2475
Ala Pro Pro Glu Tyr Arg Gly Ile Pro Gln Ile Asp Ala Thr Leu
            2480                2485                2490
Cys Ile Gly Cys Gly Ala Cys Val Asn Ala Cys Pro Pro Asp Ala
            2495                2500                2505
Leu Leu Arg Ile Asp Asp Tyr Asn Arg Gly Val Arg Glu Ile Val
            2510                2515                2520
```

```
Leu Asp Val Gly Arg Cys Ile Arg Cys Ala Arg Cys Glu Glu Val
2525                2530                2535

Cys Pro Thr Gly Ala Ile Lys Leu Thr Asn Leu Phe Glu Ala Ala
2540                2545                2550

Ser Pro Asp Arg Met Asp His Val Glu Val Val Arg Leu Arg Leu
2555                2560                2565

Val Lys Cys Lys Asn Cys Gly Arg Tyr Ala Asp Phe Thr Glu Arg
2570                2575                2580

Gln Val Arg Lys Ala Leu Gln Ile Leu Pro Glu Glu Ile Ile Glu
2585                2590                2595

Arg Glu Ala Leu Glu Glu Lys Val Trp Ile Cys Arg Asp Cys Arg
2600                2605                2610

Arg Lys Gly Thr Val Asp Gly Thr Ile Glu Ala Ser Lys Glu Val
2615                2620                2625

Val Leu Met Ser Gly Lys Pro Lys Leu Arg Ser Ile Trp Val Phe
2630                2635                2640

His Leu Asn Thr Gly Ser Cys Asn Gly Cys Asp Ile Glu Ile Ile
2645                2650                2655

Asp Val Leu Thr Pro Phe Tyr Asp Val Glu Arg Phe Gly Ile Lys
2660                2665                2670

Leu Val Gly Ser Pro Arg His Ala His Ala Leu Leu Val Ser Gly
2675                2680                2685

Pro Leu Thr Arg Gln Ala Tyr Tyr Gly Ala Lys Glu Thr Ile Lys
2690                2695                2700

Ala Met Pro Pro Glu Pro Arg Val Ile Val Ala Ile Gly Thr Cys
2705                2710                2715

Thr Cys Ser Gly Gly Ile Phe Tyr Asn Gly Tyr Pro Val Tyr Arg
2720                2725                2730

Arg Pro Glu Ser Gly Arg Glu Gly Ser Glu Tyr Pro Arg Arg Gly
2735                2740                2745

Gly Ile Ala Glu Leu Ile Ala Asp Leu Arg Asp Glu Gly Glu Lys
2750                2755                2760

Val Gly Pro Val Ile Tyr Ile Pro Gly Cys Pro Pro Arg Pro Glu
2765                2770                2775

Glu Ile Ile Tyr Gly Ile Ala Gln Leu Val Gly Leu Val Glu Lys
2780                2785                2790

Lys Leu Ser Tyr Gln Glu Tyr Ser Asp Glu Leu Val Pro Phe Lys
2795                2800                2805

Leu Pro Glu Gly Pro Leu Glu Glu Arg Ile Arg Leu Thr Leu Met
2810                2815                2820

Glu Arg Leu Arg His Leu Val Gly Tyr Leu Asp Arg Glu Lys Ile
2825                2830                2835

Leu Glu Asp Phe Met Gly Leu Val Lys Glu Ala Glu Lys Ser Glu
2840                2845                2850

Asn Pro Arg Glu Glu Leu Ala Arg Leu Val Lys Asp Tyr Ala Ala
2855                2860                2865

Lys Cys Gly Asp Val Arg Leu Gly Phe Cys Met Met Leu Leu Glu
2870                2875                2880

Arg Glu Tyr Trp Arg Val Lys Asp Ala Leu Asp Ala Gly Lys Glu
2885                2890                2895

Phe Val Tyr Trp Val
2900
```

<210> SEQ ID NO 8
<211> LENGTH: 1387
<212> TYPE: PRT
<213> ORGANISM: Thermococcus onnurineus NA1

<400> SEQUENCE: 8

```
Met Phe Gly Tyr Trp Asp Ala Leu Tyr Phe Val Ile Phe Ile Ile
1               5                   10                  15

Gly Leu Ile Ile Ala Trp Met Leu Asn Glu Trp Ala Lys Lys Ser Gly
            20                  25                  30

Met Gly Thr Arg Glu Ala Gly Asp Gly Thr Lys Val Phe Ile Ser Gly
            35                  40                  45

Glu Asp Pro Asp Lys Val Ile Pro Gly Phe Glu His Tyr Glu Gly Tyr
    50                  55                  60

Tyr Thr Gly Lys Asn Val Met Trp Gly Leu Thr Tyr Ala Leu Lys Arg
65                  70                  75                  80

Phe Phe Ala Leu Leu Arg Asn Glu His Thr Gly Leu Leu Thr Asp Tyr
                85                  90                  95

Val Ser Tyr Leu Leu Ile Thr Thr Ala Phe Val Leu Gly Val Ile Leu
            100                 105                 110

Ile Trp Gly Met Ser Ile Lys Val Pro Ala Asp Gln Asn Arg Thr Asn
            115                 120                 125

Gly Thr Thr Ser Glu Arg Glu Met Leu Glu Lys Arg Ile Ala Gln Leu
    130                 135                 140

Cys Arg Phe Ile Gly Arg Ser Pro Trp Val Phe His Val Asn Ser Gly
145                 150                 155                 160

Ser Cys Asn Gly Cys Asp Ile Glu Ile Ile Ala Ala Leu Thr Pro Arg
                165                 170                 175

Tyr Asp Ala Glu Arg Phe Gly Val Lys Leu Val Gly Ser Pro Arg His
            180                 185                 190

Ala Asp Val Leu Leu Val Thr Gly Pro Val Thr Asp Gln Ser Leu Glu
            195                 200                 205

Arg Val Lys Leu Val Tyr Glu Gln Thr Pro Asp Pro Lys Ile Val Ile
    210                 215                 220

Ala Val Gly Ser Cys Pro Thr Gly Gly Ser Val Phe Tyr Glu Ser Pro
225                 230                 235                 240

Phe Thr Asn Ala Pro Leu Ser Asn Ile Ile Pro Val Asp Val Tyr Val
                245                 250                 255

Pro Gly Cys Pro Pro Arg Pro Glu Ala Ile Leu Tyr Gly Val Val Leu
            260                 265                 270

Ala Leu Glu Lys Leu Ala Lys Ile Leu Lys Gly Glu Val Pro Glu Gly
            275                 280                 285

Glu Glu Met Ala Asp Asp Asn Arg Ile Met Glu Asn Val Asp Asn Val
    290                 295                 300

Arg Glu Pro Thr Lys Glu Asp Thr Val Ala Glu Thr Ile Lys Ser Arg
305                 310                 315                 320

Phe Pro Asn Ala His Val Glu Ile Arg Glu Asn Lys Trp Gly Arg Lys
                325                 330                 335

Arg Val Trp Val Ile Val Pro Arg Glu Asp Tyr Lys Ala Leu Met Lys
            340                 345                 350

Phe Leu Leu Glu Leu Asp Pro Glu Ala His Tyr Ser Ile Gly Ile Glu
            355                 360                 365

Gln Asp Tyr Gly Glu Glu Ile Gly Tyr Met Ser His Ile Leu Leu His
    370                 375                 380
```

```
Tyr Asp Asn Ala Pro Ala Val Ser Leu Leu Val Asp Val Arg Val Pro
385                 390                 395                 400

Lys Asp Asp Pro Val Ile Pro Asp Ile Ser Asp Ile Phe Pro Ile Ala
                405                 410                 415

Leu Gln Tyr Glu Arg Glu Ala Ala Glu Met Met Gly Ile Val Phe Glu
            420                 425                 430

Gly Ile Pro Asp Ser Arg Arg Leu Phe Leu Pro Asp Asp Phe Pro Glu
        435                 440                 445

Gly Ile Tyr Pro Leu Arg Leu Asp Glu Lys Gly Ile Pro Glu Glu Ile
    450                 455                 460

Val Lys Asn Ala Gly His Pro Tyr Tyr Leu Lys Gly Gly Asp Lys Met
465                 470                 475                 480

Thr Lys Lys Val Glu Tyr Trp Ile Lys Ile Pro Phe Gly Pro Ile His
                485                 490                 495

Pro Gly Leu Glu Glu Pro Glu Lys Phe Ile Leu Thr Leu Asp Gly Glu
            500                 505                 510

Arg Ile Val Asn Val Asp Val Lys Leu Gly Tyr Asn Leu Arg Gly Leu
        515                 520                 525

Gln Trp Ile Ala Tyr Arg Arg Asn Tyr Val Gln Ile Met Tyr Leu Ala
    530                 535                 540

Glu Arg Ile Cys Gly Ile Cys Ser Phe Ser His Asn His Thr Tyr Thr
545                 550                 555                 560

Arg Ala Val Glu Glu Ala Ala Gly Ile Glu Val Pro Glu Arg Ala Glu
                565                 570                 575

Tyr Ile Arg Ala Ile Ile Gly Glu Leu Glu Arg Val His Ser His Leu
            580                 585                 590

Leu Asn Leu Gly Val Leu Gly His Asp Ile Gly Tyr Asp Thr Val Leu
        595                 600                 605

His Leu Thr Trp Leu Ala Arg Glu Arg Val Met Asp Val Leu Glu Ala
    610                 615                 620

Ile Ser Gly Asn Arg Val Asn Tyr Ser Met Val Thr Ile Gly Gly Val
625                 630                 635                 640

Arg Arg Asp Ile Asp Glu Lys Gly Lys Arg Leu Ile Leu Asp Met Ile
                645                 650                 655

Lys Tyr Tyr Arg Ser Ile Met Pro Gln Ile Glu Glu Val Phe Leu His
            660                 665                 670

Asp Pro Thr Ile Glu Ala Arg Leu Arg Asp Cys Ala Val Ile Ser Lys
        675                 680                 685

Arg Val Ala Leu Glu Gln Gly Ala Val Gly Pro Thr Ala Arg Ala Ser
    690                 695                 700

Gly Leu Lys Val Asp Ala Arg Trp Ser Glu Arg Leu Gly Val Tyr Pro
705                 710                 715                 720

Asp Leu Gly Val Lys Pro Val Met Pro Gln Asp Val Thr Gly Glu Lys
                725                 730                 735

Pro His Gly Asp Val Phe Asp Arg Ala Ala Val Arg Ile Gly Glu Ile
            740                 745                 750

Tyr Gln Ser Leu Asp Met Leu Glu His Ala Leu Asp Gln Met Pro Glu
        755                 760                 765

Gly Lys Ile Lys Thr Phe Pro Lys Asp Asn Ile Leu Val Ala Lys Leu
    770                 775                 780

Lys Ile Met Val Asp Gly Glu Gly Ile Gly Arg Tyr Glu Ala Pro Arg
785                 790                 795                 800
```

-continued

Gly Glu Leu Val His Tyr Val Arg Gly Lys Gly Ser Asp Lys Pro
                805                 810                 815

Leu Arg Trp Lys Pro Arg Glu Pro Thr Phe Pro Asn Leu Phe Ala Val
            820                 825                 830

Ala Lys Gly Val Thr Gly Asp Gln Val Ala Asp Phe Val Leu Ala Val
            835                 840                 845

Ala Ser Ile Asp Pro Cys Leu Ser Cys Thr Asp Arg Val Ala Val Val
850                 855                 860

Gln Asp Gly Lys Lys Arg Ile Leu Thr Glu Thr Asp Leu Leu Arg Leu
865                 870                 875                 880

Ser Ile Lys Lys Thr Arg Glu Ile Asn Pro Glu Val Lys Gly Asp Pro
                885                 890                 895

Thr Pro Val Gly Phe Gly Cys Ser Arg Met Asp Val Met Ala Asn Ile
            900                 905                 910

Ile Tyr Pro Val Ala Gly Leu Ile Gly Leu Tyr Ala Phe Val Ser Leu
            915                 920                 925

Ala Ser Leu Val Trp Glu Gly Ile Asp Arg Lys Leu Val Ala Arg Met
930                 935                 940

Gln Arg Arg Val Gly Pro Pro Leu Leu Gln Pro Leu Tyr Asp Phe Phe
945                 950                 955                 960

Lys Leu Ala Ser Lys Glu Thr Ile Ile Pro Asn Thr Ala Asn Phe Met
                965                 970                 975

Phe Arg Ala Ala Pro Val Leu Ala Leu Ala Thr Ala Ile Ala Leu Leu
            980                 985                 990

Ala Tyr Thr Pro Met Gly Phe Ala Pro Leu Leu Ala Ser Lys Gly Asp
            995                 1000                1005

Val Ile Val Phe Ile Tyr Leu Leu Thr Leu Ile Gly Phe Phe Lys
    1010                1015                1020

Ile Leu Gly Gly Ile Ser Ser Gly Ser Pro Tyr Ala Lys Ile Gly
    1025                1030                1035

Ala Ala Arg Glu Ala Ala Ile Met Val Ser Arg Glu Pro Ala Met
    1040                1045                1050

Met Leu Ala Leu Phe Ala Ile Ile Trp Arg Leu Gly Lys Leu Gly
    1055                1060                1065

Val Asn Lys Pro Phe Ser Met Glu Val Phe Tyr Gln Tyr Asn Ile
    1070                1075                1080

Trp Glu Ile Gly Thr Pro Leu Ser Leu Ile Gly Ala Val Ile Leu
    1085                1090                1095

Leu Tyr Val Phe Val Ile Trp Leu Ala Ser Glu Ile Glu Val Gly
    1100                1105                1110

Tyr Phe Asn Ile Pro Asp Ala Glu Glu Glu Ile Ala Glu Gly Leu
    1115                1120                1125

Leu Ala Glu Tyr Ser Gly Arg Tyr Leu Ala Leu Leu Lys Leu Thr
    1130                1135                1140

Lys Ala Leu Lys Thr Tyr Ile Ala Ala Ser Leu Val Val Ala Ile
    1145                1150                1155

Phe Phe Pro Trp Gly Ile Ala Asp Tyr Phe Asn Leu Thr Gly Leu
    1160                1165                1170

Pro Ala Asn Val Val Asn Leu Leu Phe His Thr Leu Lys Val Phe
    1175                1180                1185

Ile Leu Leu Phe Ala Val Gln Ser Val Phe Arg Ala Thr Thr Gly
    1190                1195                1200

Arg Leu Lys Ile Thr Gln Ala Val Asp Phe Leu Trp Lys Asn Val

```
                    1205                1210                1215
Phe Leu Ala Ser Leu Ile Gly Thr Leu Leu Ile Ala Met Glu Val
            1220                1225                1230

Ile Met Val Arg Leu Ser Pro Leu Ile Pro Thr Val Leu Arg Asn
            1235                1240                1245

Met Phe Lys Lys Pro Ala Thr Asn Leu Phe Pro Ala Thr Glu Pro
            1250                1255                1260

Val Pro Val Pro Asp Asn Phe Arg Gly Gln Leu Lys Tyr Asn Val
            1265                1270                1275

Asp Lys Cys Val Gly Cys Arg Met Cys Val Thr Val Cys Pro Ala
            1280                1285                1290

Gly Val Phe Val Phe Leu Pro Glu Ile Arg Lys Val Ala Leu Trp
            1295                1300                1305

Thr Ala Arg Cys Val Tyr Cys Ser Gln Cys Val Asp Val Cys Pro
            1310                1315                1320

Thr Ala Ala Leu Gln Met Ser Asp Glu Phe Leu Leu Ala Ser Tyr
            1325                1330                1335

Asn Asn Tyr Asp Asp Lys Phe Ile Pro Leu Lys Pro Glu Lys Val
            1340                1345                1350

Glu Glu Ile Lys Lys Lys Leu Glu Glu Gln Lys Lys Ala Lys Ala
            1355                1360                1365

Ala Ala Ala Ala Lys Lys Ala Met Glu Lys Lys Glu Ala Gly Lys
            1370                1375                1380

Glu Ala Lys Lys
    1385

<210> SEQ ID NO 9
<211> LENGTH: 854
<212> TYPE: PRT
<213> ORGANISM: Thermococcus onnurineus NA1

<400> SEQUENCE: 9

Met Gly Met Ala Glu Lys Arg Ile Ser Val Val Cys Pro Trp Cys Ser
1               5                   10                  15

Val Gly Cys Arg Phe Tyr Ile Val Asn Val Asn Gly Tyr Pro Lys Lys
            20                  25                  30

Ile Glu Phe Asp Tyr Asp His Asp Ile Arg Asn His Gly Lys Leu Cys
        35                  40                  45

Pro Lys Gly Val Ala Ala Phe Gln His Leu Arg His Pro Asp Arg Leu
    50                  55                  60

Lys Lys Pro Leu Lys Arg Val Gly Glu Arg Gly Glu Lys Phe Lys
65                  70                  75                  80

Glu Ile Ser Trp Glu Glu Ala Ile Lys Glu Ile Ala Gln Lys Leu Ser
                85                  90                  95

Glu Ile Lys Glu Lys Tyr Gly Ser Glu Ala Leu Ala Phe Leu Gly Ser
            100                 105                 110

Glu Arg Cys Ser Ile Glu Glu Asn Tyr Val Leu Gln Lys Leu Ala Arg
        115                 120                 125

Ala Leu Gly Thr Asn Asn Ile Glu Tyr Val Cys Arg Met Cys Gln Ser
    130                 135                 140

Thr Ala Val Ala Gly Lys Gly Met Val Leu Gly His Pro Gly Leu Thr
145                 150                 155                 160

Asn Pro Phe Glu Asp Ile Leu Lys Ala Lys Val Ile Val Leu Trp Gly
                165                 170                 175
```

```
Tyr Asn Pro Ala Ala Thr Asn Pro Val Phe Gly Gln Tyr Ile Glu
                180                 185                 190

Lys Ala Ile Leu Asp Asn Asn Ala Thr Leu Ile Val Val Asp Pro Arg
            195                 200                 205

Lys Thr Lys Thr Ala Lys Tyr Ala Asp Ile His Leu Gln Pro Tyr Pro
    210                 215                 220

Gly Thr Asp Leu Ala Ile Ala Leu Ala Met Leu Asn Val Ile Ile Thr
225                 230                 235                 240

Glu Glu Leu Tyr Asp Lys Asp Phe Val Ala Glu Arg Ala Glu Gly Leu
                245                 250                 255

Glu Glu Leu Ala Lys Thr Val Glu Lys Tyr Thr Pro Glu Trp Ala Glu
            260                 265                 270

Lys Val Ser Gly Val Pro Ala Glu Leu Ile Arg Lys Ala Ala Ile Thr
        275                 280                 285

Phe Ala Thr Ala Gly Thr Ala Ala Leu Leu Thr Asn Glu Gly Val Asn
    290                 295                 300

Gln His Ala Asn Gly Thr Arg Thr Val Met Ala Ile Thr Glu Met Met
305                 310                 315                 320

Val Leu Cys Gly Tyr Phe Gly Lys Glu Gly Val Met Ser Gly Ala Ile
                325                 330                 335

Pro Gly Ala His Asn Gly Met Gly Ala Gly Leu Met Gly Ile Gly Pro
            340                 345                 350

His Glu Leu Pro Gly Arg Phe Pro Leu His Ala Glu Glu His Lys Arg
        355                 360                 365

Arg Ile Glu Glu Ala Trp Gly Phe Lys Ile Pro Glu Lys Pro Gly Ile
    370                 375                 380

Thr Tyr Val Glu Met Ile Asp Ala Ile Leu Glu Gly Lys Leu Lys Ala
385                 390                 395                 400

Leu Tyr Val Met Gly Thr Asn Pro Ala Lys Ala Leu Pro Asn Leu Lys
                405                 410                 415

Lys Ala Glu Glu Ala Phe Lys Asn Ile Glu Phe Leu Val Val Gln Asp
            420                 425                 430

Ile Phe Leu Thr Glu Thr Ala Lys Tyr Ala Asp Ile Val Leu Pro Ala
        435                 440                 445

Ala Ala Trp Phe Glu Lys Asp Gly Thr Ala Ile Ser Phe Glu Arg Arg
    450                 455                 460

Val Gln Arg Ser Phe Lys Ala Ala Asp Ala Pro Gly Glu Ala Lys Pro
465                 470                 475                 480

Asp Trp Glu Ile Leu Val Met Leu Ala Lys Glu Leu Gly Phe Gly Glu
                485                 490                 495

Tyr Phe Asn Tyr Ser Asp Ala Asp Ile Leu Arg Glu Ile Asn Arg
            500                 505                 510

Ile Ile Pro Pro Leu Ala Gly Ala Thr Pro Glu Arg Leu Lys Lys Asn
        515                 520                 525

Leu Lys Gly Cys Met Ile Pro Cys Pro Asp Glu Asn Thr Glu Val Pro
    530                 535                 540

Arg Leu Phe Val Gln Gly Phe Leu Thr Pro Asn Gly Lys Ala Gln Leu
545                 550                 555                 560

Ile Pro Val Glu Tyr Lys Glu Pro Gly Glu Val Pro Asp Glu Glu Tyr
                565                 570                 575

Pro Phe Trp Leu Thr Asn Tyr Arg Phe Val Gly His Phe His Thr Gly
            580                 585                 590

Thr Met Ser His Arg Ser Lys Ser Leu Ser Lys Arg Trp Pro Glu Glu
```

```
                595                 600                 605
Tyr Ile Glu Ile Asn Glu Asn Asp Ala Lys Arg Leu Gly Ile Lys Asp
    610                 615                 620

Gly Asp Leu Val Arg Val Glu Thr Arg Arg Ala Ala Leu Val Leu Arg
625                 630                 635                 640

Ala Lys Val Thr Pro His Ile Arg Glu Gly Val Val Ala Ala Pro Trp
                645                 650                 655

His Trp Asp Phe Asn Tyr Leu Thr Thr Asp Val Leu Asp Glu Tyr Ala
                660                 665                 670

Lys Met Pro Glu Leu Lys Thr Ala Ala Cys Arg Ile Ser Lys Val Glu
            675                 680                 685

Gly Met Ser Lys Lys Ile Phe Ile Asp Phe Lys Arg Cys Ile Ala Cys
            690                 695                 700

Lys Ala Cys Glu Val Ala Cys Glu Met Glu His Gly Glu Ala Arg Ile
705                 710                 715                 720

Arg Val Phe Glu Phe Pro Asp Leu Thr Ser Val Ala Phe Asn Cys Arg
                725                 730                 735

His Cys Glu Lys Ala Pro Cys Met Glu Val Cys Pro Val Asn Ala Leu
            740                 745                 750

Ser Lys Asp Asp Gly Ala Val Val Leu Asp Pro Leu Lys Cys Ile
            755                 760                 765

Gly Cys Leu Met Cys Gly Leu Ala Cys Pro Phe Gly Ile Pro Lys Ile
770                 775                 780

Asp Glu Tyr Asn Lys Ile Met Asp Lys Cys Asp Leu Cys Ala His Arg
785                 790                 795                 800

Arg Ala Glu Gly Lys Leu Pro Ala Cys Val Ser Ala Cys Pro Thr Glu
                805                 810                 815

Ala Leu Lys Tyr Gly Asp Ile Asn Asp Val Leu Trp Ala Arg Glu Gly
            820                 825                 830

Lys Ile Val Ala Glu Leu Lys Asp Ile Gly Asp Arg Thr Asn Val Leu
            835                 840                 845

Glu Ala Tyr Leu Ile Arg
    850

<210> SEQ ID NO 10
<211> LENGTH: 630
<212> TYPE: PRT
<213> ORGANISM: Thermococcus onnurineus NA1

<400> SEQUENCE: 10

Met Ala Gly Lys Lys Val Pro Ser Lys Gln Val Ser Ile Thr Pro Gly
1               5                   10                  15

Val Gly Lys Leu Ile Glu Lys Ala Glu Glu Asp Gly Val Lys Thr Ala
            20                  25                  30

Trp His Arg Phe Leu Glu Gln Gln Pro Gln Cys Gly Phe Gly Leu Leu
        35                  40                  45

Gly Val Cys Cys Lys Asn Cys Thr Met Gly Pro Cys Arg Ile Asp Pro
    50                  55                  60

Phe Gly Val Gly Pro Thr Lys Gly Val Cys Gly Ala Asp Ala Asp Thr
65                  70                  75                  80

Ile Val Ala Arg Asn Ile Val Arg Met Ile Ala Ala Gly Thr Ala Gly
                85                  90                  95

His Ser Asp His Ser Arg Asp Val Val His Val Phe Lys Gly Ile Ala
            100                 105                 110
```

-continued

```
Glu Gly Lys Phe Lys Asp Tyr Lys Leu Thr Asp Val Glu Lys Leu Lys
            115                 120                 125
Glu Leu Ala Lys Ile Leu Gly Val Glu Thr Gly Lys Ser Glu Asn
        130                 135                 140
Glu Ile Ala Leu Glu Val Ala His Ile Leu Glu Met Glu Phe Gly Lys
145                 150                 155                 160
Gln Asp Glu Glu Pro Val Arg Leu Leu Ala Thr Ala Pro Lys Lys
                165                 170                 175
Arg Ile Lys Val Trp Glu Lys Leu Gly Val Leu Pro Arg Ala Ile Asp
                180                 185                 190
Arg Glu Ile Cys Leu Ser Met His Arg Thr His Ile Gly Cys Asp Ala
            195                 200                 205
Asp Pro Ala Ser Leu Leu Leu His Gly Val Arg Thr Ala Leu Ala Asp
        210                 215                 220
Gly Trp Cys Gly Ser Met Met Ala Thr Tyr Leu Ser Asp Ile Leu Phe
225                 230                 235                 240
Gly Thr Pro Lys Pro Ile Lys Ser Leu Ala Asn Leu Gly Val Leu Lys
                245                 250                 255
Glu Asp Met Val Asn Ile Ile Val His Gly His Asn Pro Ile Leu Ser
            260                 265                 270
Met Lys Ile Ala Glu Ile Ala Gln Ser Glu Glu Met Gln Lys Leu Ala
        275                 280                 285
Glu Gln Tyr Gly Ala Lys Gly Ile Asn Val Ala Gly Met Cys Cys Thr
        290                 295                 300
Gly Asn Glu Val Leu Ser Arg Met Gly Val Gln Val Ala Gly Asn Phe
305                 310                 315                 320
Leu Met Gln Glu Leu Ala Ile Ile Thr Gly Ala Val Glu Ala Val Ile
                325                 330                 335
Val Asp Tyr Gln Cys Leu Met Pro Ser Leu Val Asp Val Ala Ser Cys
            340                 345                 350
Tyr His Thr Lys Ile Ile Thr Thr Glu Pro Lys Ala Arg Ile Pro Gly
        355                 360                 365
Ala Ile His Val Glu Phe Glu Pro Glu Lys Ala Asp Glu Ile Ala Lys
        370                 375                 380
Glu Ile Ile Lys Ile Ala Ile Glu Asn Tyr Lys Asn Arg Val Pro Ala
385                 390                 395                 400
Lys Val Tyr Ile Pro Glu His Lys Met Glu Leu Val Ala Gly Phe Ser
                405                 410                 415
Val Glu Ala Ile Leu Glu Ala Leu Gly Gly Thr Leu Glu Pro Leu Ile
            420                 425                 430
Lys Ala Leu Gln Asp Gly Thr Ile Lys Gly Ile Val Gly Ile Val Gly
        435                 440                 445
Cys Asn Asn Pro Arg Val Lys Gln Asn Tyr Gly His Val Thr Leu Ala
450                 455                 460
Lys Glu Leu Ile Lys Arg Asp Ile Leu Val Val Gly Thr Gly Cys Trp
465                 470                 475                 480
Gly Ile Ala Ala Ala Met His Gly Leu Leu Thr Pro Glu Ala Ala Glu
                485                 490                 495
Met Ala Gly Pro Gly Leu Lys Ala Val Cys Glu Ala Leu Gly Ile Pro
            500                 505                 510
Pro Cys Leu His Met Gly Ser Cys Val Asp Cys Ser Arg Ile Leu Leu
        515                 520                 525
Val Leu Ser Ala Leu Ala Asn Ala Leu Asn Val Asp Ile Ser Asp Leu
```

-continued

```
            530                 535                 540
Pro Val Ala Gly Ser Ala Pro Glu Trp Met Ser Glu Lys Ala Val Ala
545                 550                 555                 560

Ile Gly Thr Tyr Phe Val Ala Ser Gly Val Phe Thr His Leu Gly Val
                565                 570                 575

Ile Pro Pro Val Leu Gly Ser Gln Lys Val Thr Lys Leu Leu Thr Asp
            580                 585                 590

Asp Ile Glu Asp Leu Leu Gly Gly Lys Phe Tyr Val Glu Thr Asp Pro
            595                 600                 605

Val Lys Ala Ala Glu Thr Ile Tyr Asn Val Ile Glu Lys Arg Lys
        610                 615                 620

Lys Leu Gly Trp Pro Ile
625                 630

<210> SEQ ID NO 11
<211> LENGTH: 877
<212> TYPE: PRT
<213> ORGANISM: Thermococcus onnurineus NA1

<400> SEQUENCE: 11

Met Ser Glu Arg Leu Val Pro Val Cys Pro Tyr Cys Gly Val Gly
1               5                   10                  15

Cys Arg Leu Tyr Ile Arg Ser Val Asp Gly Tyr Pro Val Gly Ile Glu
                20                  25                  30

Tyr Ala Lys Asp Ile Pro Asn Ile Ser Asn Glu Leu Gly Lys Leu Cys
            35                  40                  45

Pro Lys Gly Asn Ala Val Val Glu Tyr Leu Leu Ala Lys Asp Arg Leu
        50                  55                  60

Lys Arg Pro Leu Lys Ala Lys Glu Gln Gly Lys Phe Val Glu Ile Ser
65                  70                  75                  80

Trp Ser Glu Ala Ile Lys Glu Val Ala Glu Arg Leu Lys Ala Tyr Ala
                85                  90                  95

Lys Asp Asp Pro Asn Gln Leu Met Phe Phe Gly Ser Ala Arg Thr Phe
            100                 105                 110

Asn Glu Pro Asn Tyr Leu Val Gln Lys Leu Ala Arg Met Leu Gly Thr
        115                 120                 125

Asn Asn Val Asp His Cys Ala Arg Leu Cys His Ala Pro Thr Val Thr
    130                 135                 140

Gly Leu Lys Ala Val Phe Gly Ala Gly Ala Met Thr Asn Thr Tyr Lys
145                 150                 155                 160

Asp Ile Glu Glu Ala Asn Val Ile Phe Ile Ile Gly His Asn Tyr Ala
                165                 170                 175

Glu Thr His Pro Val Gly Phe Arg Tyr Val Leu Lys Ala Lys Glu Arg
            180                 185                 190

Gly Ala Lys Val Ile Val Ala Asp Pro Arg Phe Thr Arg Thr Ala Trp
        195                 200                 205

Phe Ala Asp Ile Phe Leu Gln His Tyr Pro Gly Ser Asp Ile Ala Leu
    210                 215                 220

Ile Asn Gly Leu Ile His Val Ile Lys Glu Arg Leu Tyr Asp Glu
225                 230                 235                 240

Lys Phe Val Arg Glu Arg Cys Val Gly Phe Asp Glu Val Val Ala Ala
                245                 250                 255

Val Glu Lys Phe Thr Pro Glu Phe Val Glu Lys Val Thr Gly Val Pro
            260                 265                 270
```

-continued

```
Ala Glu Leu Ile Ile Glu Ala Arg Thr Phe Ala Thr Ala Gly Lys
        275                 280                 285
Gly Val Ile Thr Trp Ala Met Gly Leu Thr Gln His Thr His Gly Thr
290                 295                 300
Glu Asn Val Lys Leu Leu Gly Thr Leu Ala Ala Ile Cys Gly Tyr Gln
305                 310                 315                 320
Gly Lys Glu Gly Ala Gly Cys Ser Pro Met Arg Gly Gln Asn Asn Val
                325                 330                 335
Gln Gly Ala Cys Asp Met Ala Ala Leu Pro Asn Val Phe Pro Gly Tyr
                340                 345                 350
Gln Ala Val Thr Asp Pro Glu Lys Arg Lys Phe Phe Glu Glu Phe Trp
                355                 360                 365
Gly Val Glu Leu Ser Gly Glu Val Gly Leu Thr Thr Val Glu Ala Ala
        370                 375                 380
Tyr Ala Ala Asp Lys Gly Lys Val Lys Ala Tyr Tyr Val Met Gly Glu
385                 390                 395                 400
Asn Pro Val Ile Ser Glu Ala Asn Ala Asn His Val Met His Thr Leu
                405                 410                 415
Glu Lys Leu Glu Phe Met Val Val Gln Asp Ile Val Pro Thr Pro Thr
                420                 425                 430
Met Glu Tyr Ala Asp Ile Val Leu Pro Ala Ala Ala Met Leu Glu Asn
        435                 440                 445
Glu Gly Ser Leu Thr Asn Thr Glu Arg Arg Val Gln Trp Ser Phe Gln
        450                 455                 460
Ala Val Lys Pro Pro Gly Glu Ala Arg Pro Asp Trp Trp Ile Leu Ser
465                 470                 475                 480
Glu Val Gly Lys Ala Ile Gly Phe Asp Lys Thr Gly Ser Gly Gly Phe
                485                 490                 495
Val Tyr Asn Asp Ala Ala Asp Val Leu Arg Glu Ile Asn Ala Cys Thr
                500                 505                 510
Pro Gln Tyr Arg Gly Ile Thr Pro Glu Arg Leu Lys Glu Asn Leu Ala
        515                 520                 525
Gly Leu His Trp Pro Cys Pro Ser Glu Asp His Pro Gly Thr Arg Val
530                 535                 540
Leu Tyr Lys Glu Lys Phe Leu Thr Pro Ser Gly Lys Ala Asn Leu Ala
545                 550                 555                 560
Ala Val Pro Glu Tyr Lys Gly Pro Val Glu Met Pro Asp Glu Glu Tyr
                565                 570                 575
Pro Phe Leu Leu Thr Thr His Arg Tyr Val Gly Met Tyr His Thr Ala
                580                 585                 590
Thr Met Thr Met Arg Ser Cys Ala Leu Lys Lys Arg Trp Pro Glu Pro
        595                 600                 605
Leu Ala Glu Ile His Pro Asp Asp Ala Val Lys Leu Gly Ile Lys Ser
        610                 615                 620
Gly Asp Trp Val Lys Val Thr Arg Arg Gly Ala Tyr Pro Ile Lys
625                 630                 635                 640
Ala Lys Val Thr Arg Ala Val Lys Lys Gly Val Ile Ala Val Pro Trp
                645                 650                 655
His Trp Gly Ala Asn Val Leu Thr Asn Asp Ala Leu Asp Pro Val Ala
                660                 665                 670
Lys Ile Pro Glu Thr Lys Ala Cys Ala Cys Asn Val Ala Lys Ile Thr
        675                 680                 685
Glu Glu Glu Ala Arg Lys Leu Met Glu Lys Leu Pro Pro Leu Ile Pro
```

```
                690                 695                 700
Lys Ile Glu Val Val Arg Gly Met Ala Arg Lys Thr Val Phe Ile Asp
705                 710                 715                 720

Phe Ser Lys Cys Ile Glu Cys Arg Ala Cys Glu Val Ala Cys Glu Arg
                725                 730                 735

Glu His Ser Gly Met Ser Phe Ile Ser Val Phe Glu Trp Gln Glu Met
            740                 745                 750

Ala Ala Met Ala Leu Asn Cys Arg His Cys Glu Lys Ala Pro Cys Val
        755                 760                 765

Glu Val Cys Pro Thr Asn Ala Leu Tyr Arg Asp Lys Asp Gly Ala Val
770                 775                 780

Leu Leu Ala Pro Gln Lys Cys Ile Gly Cys Leu Met Cys Gly Ile Val
785                 790                 795                 800

Cys Pro Phe Gly Ile Pro Glu Leu Asp Leu Ile Asn Lys Ile Met Gly
                805                 810                 815

Lys Cys Asp Leu Cys Ala His Arg Arg Ala Glu Gly Lys Leu Pro Ala
            820                 825                 830

Cys Val Glu Thr Cys Pro Thr Asp Ala Leu Ile Tyr Gly Asp Phe Asn
        835                 840                 845

Glu Ile Val Lys Lys Arg Arg Glu Lys Phe Thr Glu Lys Thr Ile Glu
850                 855                 860

Leu Ala Lys Thr Ala Glu Arg Ile Pro Leu Thr Gly Val
865                 870                 875

<210> SEQ ID NO 12
<211> LENGTH: 4194
<212> TYPE: DNA
<213> ORGANISM: Thermococcus onnurineus NA1

<400> SEQUENCE: 12
atgggattcc taagcagact gttcggtggg aagaaggaaa ccgacactga ggaaattcag      60
atagtctcga ggaagccagt tggaaagttc cacgttgaga aggtcttcca catcatggga     120
cgcgaaaccc tcgtggggac cgtggagaga ggagtaatct atccaggcta caaggttaag     180
ggaaagaaag ccgcagtgat ctacaggata gagaaaggta gaaaggctgt ggattttgtc     240
gtcgacggag acaaggctgc actcattctc gagggaatta ctaaagcgga gagggagat     300 acccttgaag tctatcagtc gtgaatgata atcgagttga gggagttcac gagagttgaa     360
ggcaacggca agccgagat agttgtcgag aacggtgaag ttaaggacgt caggctcaaa     420
atcgttgaag ggccgcgctt cttcgagctg ctgactttgg gaaggcatta ctatgacgtt     480
ccagacttgg aagcgaggat atgcgccata tgctacctct cacacagcgt cgcctcggtt     540
ctgggcatag agaaggcctt cggagttgaa gtttcggagg agatccagct cctaagagag     600
ctcggcctca tcggtgaatt actggagagc cacgcactcc acctgtacct gtcgttgct     660 ccagacgttt tcggttatcc tgacgcgata agaatggcta cgaagcacgg ggagctcgtc     720
aaggaggggc ttgcactgaa ggccttcggc aacagtataa gggaactcat tggaggaagg     780
gagatccacg gcataaacgt taaacccggt ggatttggca ggtatccgac ggttgaggaa     840
cttgaaaaca tcgagaggga gagtggggcc tcctgagac tcgcaaggag agcggtgagg     900
ctattcgctt cgcttgagcc tacggcgaa aaggcgggac acttcgtcgc gacggacggc     960
tacctatggg gcgacaagct gatttccgat gaggatggct cttttccacta caccgagaga    1020 atagaggaac gctcactggt ttacagcttc gcaaagcaga gccgctataa gggtgagccc    1080
```

-continued

```
ttcttcgttg gcgcactgcc gaggctcctg ctcaaagcag agatgctgac acccacagcg      1140
aagaggctct tcgaggagca cagggaaaag ctcgccaccg gttacgtcag ctacaacaac      1200
ctcgctcagg ccatagagct cgtctacgcg cttgaaaggg cgggagagat agcaaagaaa      1260
ctcctcgaca agggcataaa gggtgaaaac gttcccgttg aagtcaaaga aggcgagggc      1320
atagggtacg tggaagcgcc tagggtgtc ctaatacatc actaccgcat tgactctggg       1380
ggcaaaatcg cctactcgaa catcataacg cccacggctt taaaccacgc tatgatggag      1440
gcaagcctgt tcaaggaagc gagaaaactc tacggagaga cggacgagac ggtactcgtc      1500
cagaggctgg aggaaacggt tagagccttt gatccgtgca tttcctgttc agtgcacatc      1560
gtgaagcttt agatgatgga caagctcaag ttggccgtct tcgagcttac cgactgcggc      1620
ggctgtgcgc tgaatattct cttcctctac gagaagctgt ttgacctgct cgagttctac      1680
gagataacgg agttccacat ggcgaccagc ctaagcgagg ggagccacta cgacgtggcc      1740
ctcgtaaccg gaacggtctc aagccagcgc gacctagcgc tcctcaagga ggcaagaaac      1800
cactccgact acctcatagc cctcggaacc tgcgcaacgc acggctcggt tcaggctagc      1860
gtcgagggga gcataaggga gaagctgaag agggtctatg gagatgaggg caacccgatg      1920
agggcgctga ctcgaagcc cgtcgttgag tacgtcgccg ttgatttcgc cctcccaggc       1980
tgtccctacg acaaaaacga ggtatatcag gttctgatgg acattgccaa aggcattgag      2040
ccggtaaaga aagactaccc cgtctgcgtc gagtgcaagc tcaacgaata cgaatgtgtt      2100
ctcgtgaaga agggcctccc ctgcctcggt ccaataacct acggcggctg caacgctgct      2160
tgtatacgct ccgggctggg atgcataggc tgtcgcgggc cgttgcccgg cgaggtgaat      2220
cctgcaagtg agtacgagat actcaaggat ctgggctacg atgatgacta catcctcagg      2280
aagttcaaga ccttcgcgag gtgggagcca tgaatgagcg agaatccaca tcaaacttac      2340
gatgcgcgca ttctggaagt gaaggaccta acacccaggg agaagctctt cacgctccgc      2400
ttcttagacc cggaaattgg cgaacacttc acattcaagc ccggccagtt cgtcatcgtc      2460
gatatacggg gcttcggtga gttccccata agcctctgct cctcaccaac gagaaaagga      2520
tacattcagc tctgcatcag aaaagccgga aggatgacca agttcatcca tcagatgaaa      2580
gagggagaag tggtgggcat ccgcgggccc tacggcaacg gcttcccgat ggagaaaatg      2640
gagggctcga atctactcct ggtcgccggt ggactcggta tggcaccccct ccgctcggtt     2700
ctctggtacg cgatagacac cggaaagtac gagcacgtct ggctcctcta cggcaccaaa     2760
gcctacgagg acatactctt ccgcgacgag ataatccacc tgctgaagca cggcgacgcg     2820
gttggctgca gcgtaaagct cgcctatgag gtcgaaagcc cctcgtgcat ctacctcgag     2880
cggggcttct tcgacagggt gtgcaagggt gtcgttaccg acctcttccg cggggaggag     2940
ttcgacgtcg acaaggctta cgccctcatc tgtgggccgc cggttatgta ccgcttcgtc     3000
atcaaggagc tcctagacag gaaactctcg ccgggcagga tatacatgac cctcgagagg     3060
cgcatgcgct gcggaatagg caagtgcggc cactgtatag tgggaacgag cacctccata     3120
aagtacgtct gcaaggacgg ccccgtcttc acatactggg atgctctctc cacgaggggg     3180
ttgatatgat tgagatatgt aaaactatca tctgagaact ttagctcatt ttttgaatct     3240
ctaaggaatt ggggcaaagt ctacgctccc atcaaaagag gaagcattta cacattccaa     3300
gaagttcacg agctaggaga gatagaactc aactatacaa ggacaatgct acctccaaaa     3360
aagttcttcg tgaggccaag ggacgaaatt cttcgcctga agaacggtcg ctgggaaaat     3420
ggaaccgacg cagagccgat agttctcttc ggcctccact cctgcgatat gcacgggctc     3480
```

```
aagattctcg ataaggtcta tctcgacgag cccgccgacc cgtactacaa ggcgaggcgc    3540
gagaaaacct tcatagttgg gataagctgc atgcccgacg agtattgctt ctgcaagagt    3600
ctcggcacgc actttgccat ggacggcttt gacctattcc tgcacgagct tcccgacgga    3660
tggctcgtca ggataggaag tgtgagggga cacgaggtag tctgggagaa cggtgagctc    3720
ttcgaggagg tgaccgacga ggacttgaag cacttcaagg agttcgagga gaggcgcgca    3780
aatgcgttcc agaaggagat cccgcaggaa ggactcgcag acatgctcga tttggcctac    3840
aacagcccgg tctggaagga gtacgccgag atatgcctgg cctgcggcaa ctgcaacatg    3900
gtctgtccta cctgccgctg ctacgaggtc tgcgataact ggatcagcgc ctacgacgcc    3960
gtcagagaga gacgctacga ctcctgcttt atggagaacc acggactggt tgccggaggc    4020
cacaacttca ggccaactag actcgacaga ttcaggcaca gatactactg caagagctac    4080
ttcgatccct cctcgggtta taactgcgta ggttgtggaa ggtgtgacga gttctgcccg    4140
gcgaagatag agcacgtcaa ggttcttgag gaggtcaggg ggtcgctgag atga    4194
```

<210> SEQ ID NO 13
<211> LENGTH: 7506
<212> TYPE: DNA
<213> ORGANISM: Thermococcus onnurineus NA1

<400> SEQUENCE: 13

```
atgaacgcct ctcccttcat tatatctttt ttgatccccc tgctcctcgg tccactcctg      60
ttcaaattag acggtagaaa ggccgatgta ttcatgctca tcgccgttgt gtcttccttc     120
ctggctaatc ttgtgggagt cctcgaatac ctgaaagtcg gtggcgctca tcatatcgtt     180
tacctcgaaa cttcttccct cggtgaggtc tacggcgtta taatcgaccc aatgagcgtt     240 tggtcggtt ttgtcgtgag cttggctggc gtgctgttcc ttctctacgc ggtggactac     300
atgagcgaga gaaacaagca gcaccccgtc tactctgata agggcaggtt ctatgcttgg     360
atggtcatct tcgttggagc tacgctggca ttcatatact cctccacgac gcttcagctg     420
ctcatattct tcgagataat gggactcgcc tgctggggtg tcgttgggta ttataagggc     480
ccaaaagccg agagggctgc atacaaggcc ctgcttgtgc cgaacttcgg tgccatggtg     540
ggcctctaca ccaccgttgg cattggcatc ctcaagctcc atgatttgag catctatgcg     600
ctccagaacc tgaatgatga gctcaagctt ctcgtgttcc ttggcgtaat ggttgcggcc     660
tttaccaaga gcgcccagtt cccgctctat tcatggcttc cggatgcaat ggcggcgccg     720
acacctgctt ccgcttttct ccacggtgct gcaatggttg aaatgggcgt ttacctgctc     780
gccagggtca cccagttcat gcaaccgatt ccggagacag cttctacgt tatgctcgtc     840 ttcgtgtcgc taactttact catagcaatt ctctactacc cgctccagaa ggacgccaag     900
agactccttg cttattcaac catagcagag gcaggagtga tgtacgttgg cgtgctctat     960
gccgtgcttg gctctgtcta tggtctccag gcggccatgt tccagctggc taaccacgct    1020
ttcgtcaagg gtcttgcctt cctcaccgcg ggaaccttca gttacgcttt tggaacgctc    1080
gacatggaga agattagggg cctcggaaag ctcgttccgg tcgttggtgc aagctggttc    1140
ttagcccttc tcggcctggc tggagttcct ccgctcggcc tgttcttcag caaggcgtat    1200
ctcttcatga acgcgtcttc aataaccagc tgggttggct ggattccgct cttcctagtg    1260
ttggccgatg ccacggtttt ccttgcggta tctctcggat ggattaagag gatggtattc    1320
agcgagcccc tccaggagag tgcagaagtt tccccgctga tgcgctttgt cctcgtagtc    1380
```

```
ctaatagtcc tgtccatcgt tgcgccgttc ctaagcgtga agctcgtgac tcagataggg    1440
ttcatggggt gaatgatgga aattccaatc gcgctctact cactctcagc gatttccggc    1500
ctgattggag actttaagcg gagcattaag atttcaagcg tcctctcagc catagcatcc    1560
ctatcccttc tgggcatagc tgcccacgcc tgtccaggg ggcttcccgt tcaggagagc     1620
tttttgggca ttcccctaat catagacagc ctctccctcc cgttcctgtt catcatagcc    1680
ctgctcagcc ttgtggtttc agtgtattcc atttcatata tggaagtcca cagagatacc    1740
ggaagaccac tggcgtacac catcctctac ggcacgttcg tgctgtcgat tgtattcgtg    1800
gctctgacgt caaacctgct ctggttcgtc ttcttctggg agctgatgac cctaacttcc    1860
ttcatcttcg tgagctggag ggagcaggac gctggaatta aatacctcct cacgatgcag    1920
ctcgccaaca cggtgcccct cttcgtggcc ctcggcataa tctactccgc cactggaagc    1980
ttcagcgttg attacgccac gcttagggag gttgcatctt ccctttctcc agtccagctc    2040
aagctgctct acgcgatgtt cctcgtgacg ttccttgcaa aatctggaag cgtgcccttc    2100
cagttctggg tgcccgatgc atacgaagcc gctcccagca atatagcctc gctgatggcc    2160
ggcgtcatgg agaagatggc ggtttacggt ctgataaggc tcctctgcaa cgccctgcca    2220
tgcagtgaag gcattggtta cgttctcgtt atcgtcggca tacttaccat gaccttcgga    2280
accctctacg ccctcagaga gactcacgca aagaggctcc tcgcttactc aagcgttgga    2340
caaatgggct acatctggtt cgcggtgggc atgggcatga tcttcctgac gatgggcatg    2400
gagagcctgg cttacctggc cttcctcgcc ggagtcttcc actccttcaa tcacacactc    2460
ttcaaggggc tgctctttct catctcgggc aacttcgagt actccgccgg aaccgctgac    2520
ctcaacgagc ttggtggttt gaggagggca atgccgtact cgtcgctctt caccgtcata    2580
ggtgcgctct ccctcgctgg agtgcccctc ttcagcggtt tcctctccaa gtggatgatt    2640
taccaggccg gctactactc tggaatcggc ctcttcgtct ttggctccgt aatggcggtg    2700
tttatgagcg ccgtaacctt ggcatattcg ctcaagctct acacctctgc ctttggggc     2760 gaaccgaacg agagaactga gaacgccagg gaagtcccgt cgggtatgct cctcggtgag    2820
ggaattattg ccttaacttc acttgccgtt ggaatacttc cggctattgc ttacccgata    2880
ttaacgattt cattgaatgg cggcgacgtc accgttacaa tgggctcgat atccactgac    2940
tttgagtact ctctcgccaat agccctgctc cttgcggttt cattcattgc ggttgcttca    3000
tacttcgtct tcaggccaaa gacgaccaat gtcaaaccct ggaacactgg agcgcttttc    3060
ctgccggagg agaggtatgg agcgaaggcc agggactatt acaggcagta ctttaccgag    3120
atggagggcc tctacaagct tggaagcgcc gctggcaagg tcggaagggt ccttctctct    3180
gctctgatgt ccgtctacct cgttctcgcc aggggcctcg tctacaccgg cagggagaag    3240
aagcgctcct tcacccttga cgagcttcgc caccgcaccg tcaggtacct ggacgaggca    3300
ttcttcgcgc cgatgatgga tctactcaaa aacatcgccg tgctggcagc gggcatctcg    3360
gtgtccatgg acgagctctt cctggcttca atgctgacca cggtgataat actcgcactc    3420
cttgtgttgt gaatggacta cgtaagcatt atcgctgctc cgatcgtcct cttcctcctt    3480
ccaccgttcc ttgacggaat agggagaagg ataaaggcga ggattcagta caggagagga    3540
ccgcctataa tgcagacgtt ctacgacctc gaaaagcttc tcaagctgcc gtcagtgctt    3600
ccaactgagg gcccaatctt caggctggcc ccgtacatag ccctggcatc tgccattgcc    3660
ggcggcctaa tgcttccctt cggaagcgag ccggtgttgg cttttggaaa gagcctcata    3720
gtgttcttct acgtcatggc gatggtcagc gtagtgatga tacttgctgc tttctccgtc    3780
```

```
cagaacgcgt tctctcacat aggtggacac agagaggtca tgctgatact ctcgattgag    3840
ccagtgctgg ccgtcgtctt cggtgtcctg gcattcaagc ttggaacgct caacgtcgct    3900
gagatgcctt tcagtgctaa cctctcgctt tccgttgccc tagcttacat cttgctggct    3960
tacgcggtct acgttgaggg cggattcgtt ccatttgaca tagctgaggc agaaaccgaa    4020
gtaatcgggg gcccgctcac cgagtacagc ggaaggctcc tcggagtctt caagtacgcc    4080
ctgctcgtca gagggttgt cctgctctgg ctgctggcgt ctatgattgt gattcccgcc    4140
atgaggtctc tcggtataac aagctcaatg gcactgctcg tcgcccagct ggtcgttacg    4200
tttctgcttt attcgcttgc cgtggccgtt gaggctgcaa acgcccgcct gaggatcgac    4260
caggcggttt cccttaacaa gaaggtcttc ctgatgtccc ttgctgtcct gataatagcg    4320
ctggtggggt ggtgaatgga gtgcagcgtg tgtgcgggtg gatgcagatc ggctgaagtt    4380
gaggacgtcc ttgaggatgg tcatctaaag gaattcgtgg agaagtttag gggagcgatc    4440
ttcgagtgca agaagctgac gaggaaccag tacctgttca tcgttgatag ggaggcactt    4500
ccggagatgg tcctccactg gcacaaccat tccgagctaa agaaaccca cttctcgatg    4560
ggaacaggaa ccgatgagag gaacatcgcc ggaaagttca cctacgctcc ggtaataaac    4620
gttgccgttg agcctggaaa cggggagagg aactactggg ttattctgaa ggcctacctc    4680
gacgaggaca acccggagtt ccctccata gccgcgaagc ttccagcagc cctctgggcg    4740
gagagggaag tctatgatct gcttggcttc aaccccaaag gccatcccga cctgaggagg    4800
ctcgtcctgc cggaggactg gccggagggt gtttacccgc tcaggaagga ccatgactac    4860
aaggcctcgc cgatggatac gccaaagtgc tactacaagc ccgggccgcc cgacacaatg    4920
acggttccga ttggtccgta ccacctggcg ctcgacgagc cggcccactt caggatattc    4980
gtcaagggg aaacggtggt tgacgttgac taccgcggct tctactccca cagggaatc    5040
gagaagatag gagagggaag actgacctac aatcaggtgc tcttcatagc cgagagaata    5100
tgtggaatct gtggcttcca gcactcgacg agctacgccc aggcggttga aaacatagcc    5160
ggcgttgaaa tccccgagag ggccatgtac ataaggacga taatgctgga gatagaaagg    5220
attcactccc acatgctctg ggccggtgtt gcggctcacc tgacgggctt tgacacggga    5280
ttcatgcacg cttggcgcgt cagagagcct gttatgtggc tcgcagagag gctcacagga    5340
aacaggaaga cctacggaat caacatcgtc ggaggagtta ggagggactt cctcgactac    5400
cgcaaggaga tgataatgga gaagatcaag gagctcagga ggcaggtcga agagttcatc    5460
gaaatagcga ccggtacggc aaccttcgtc aagagggccg aggggttgg aattctgccg    5520
tacaaggtgg ccaaggctta ctcagtcctt ggtccgaacg gaagggccag tgggaggaac    5580
attgacatta gaagggatca gccgttcgca gcatacaagg atttggactt caaggttcca    5640
gtctacaagg agggcgacgt cttggcaagg ttcctcatca ggatggacga ggtgctcgag    5700
agcatctgga taatagagca ggccattgac cagatgccgg aggagacgt cttcgtgccg    5760
ataggggagc ttccggagta tgaagaggcc ctaggctaca gtgaagctcc aagggcgaa    5820
gtcatccact acgtcatgac tgacaagaag aacaaggtct accgctggaa ggttagagcc    5880
ccgacctaca acaaccttcc agctgttccg gagatgctca agggctacag cgttgccgat    5940
gccccgctca tcatagcgag catagatccg tgctactcct gtacggagag ggttcagata    6000
gtggacgttg agaccggaaa ggcccagacc ctgaacgagc agcagttcaa catgctctca    6060
atacagaagg gcaagggggt ggcctgaatg gcccaggcga tttccttcac cgacaggctc    6120
```

```
aagttctgga agcgaccaga ggaggacgtt aagaaggctc ccgtcacgac ttcttatcct   6180
tttgttgata tcgaaaagcc gccggaatat aggggcatac ctcgcataga tcctcacctc   6240
tgcattggtt gtggagcctg tgttagggcc tgtccaccgg acgcgctcac gatagagtgg   6300
gacttcgaga acgggaggaa gaggatagtc ttcaacgccg cgcgctgcat aaggtgccac   6360
cgctgcgtcg aggtttgtcc aaccggtgcg atgcagggca caacgaggtt cgagatagcg   6420
acgccgaaca aggaggacct catcgaggtc gttgaccaca agctctacag atgcccgcgc   6480
tgtgggcggt acgaggagtt caccgagagg cagatag gga agatgttcca gattctgccg   6540
gaggaagtca ttgaccagca cggcatagct gagagggctt ttctctgcag ggagtgcagg   6600
atggaggaga gcgccaagac cttggcggtt caagggccct atgcggatag ccttctcctt   6660
tccctctatc cgagaggctc aaaggtgatg ggtgagagga gatgaatgag cgggttgaag   6720
tccgtttggg tcttccacgt tgacagtggg agctgcaacg gctgcgacat agagatactc   6780
gacgtgctca cgccctatta cgacgccgag aggcttggga taaagctcgt gccgagtcca   6840
agacatgccg atgccctcct cgtttcaggc ccactcacga ggcagactta ctacgctgtc   6900
aaagcagcct acgaggcgat gccgccgaag ccgaggatag ttgtggccat aggcacctgc   6960
gcgtccagtg gtggtatatt ctacaacggt tacccaatct acaacccgaa ccctgagagg   7020
ggaagcgaca ggctcaggac gggtggaata gaggtccttt tggcggagta cgggaaaaag   7080
cccgacatgt acattccagg atgtccaccg agtccgagg agatactata tgggctggcc   7140
cagctcctcg gcctgaagga gaagaagatg aagggcgagt actactatgc agacgagatt   7200
gagttcgttc ttccagagag acccatcgag gagaggattc acctgacgct cagagaatcc   7260
ctgaggcgcg tcgtggggta cttcgacagg gagaaggttc tcgaggactt catggccctc   7320
gtggaaaagg ctcaggagag cgagaacccg agggagaggc tccacgagct agtcatcgga   7380
tacttcctga gggagaagga ttcccgtgtg aagttcgcga taaggttcct cgaaaacgag   7440
tactggaggt tgaaggatgc ctacgaaaag aggcacctgg cacttgttaa agctggtgta   7500
cgttaa                                                              7506

<210> SEQ ID NO 14
<211> LENGTH: 2982
<212> TYPE: DNA
<213> ORGANISM: Thermococcus onnurineus NA1

<400> SEQUENCE: 14
atggtggact ggagactctt tgaacctctc tttaattatg cgagaaagaa gagcctttgg     60
attgtgtcgt tctgtaccgg atgcggcggt atagagatgc cgcccctcat gacgtcaagg    120
tatgacctag agcgattcgg tatgataccg gacccgagtc aagacagta cgacctcttc     180 ctcatcacgg gctacgttac gccaaagacc ctcaaaagaa tcataatcac ctacgaaatg    240
gcacctgatc caaagtacgt cctggcgcac ggctcctgcc cgctcaacgg tggaatctac    300
tgggacgcct acaacgctat caagcacctc gacaagtaca tcccggtcga tgtcgtcata    360
gccggatgca tgccgcggcc agaggcagtc atggacggaa tccagaagat aatggagatg    420
attgagaacg aacagcagag cggatggaag aggtacaagg agaactacga gtggtacaag    480
aagaaccagg acgagctctt cggcgaagga tggcgtgaga gggaagccag aaggtggatc    540
ccatggctgg tggacaagaa aaaggaggag tgaatggggg aagttaagtg ggagagagag    600
cagatgctct tgacaaaat ccttgaaaaa gccccctacg ccgagggcaa ggtgcggcgc    660
gaacggagga ttgagttcag cattccggca gacaggataa gggacttcct catgctgctc    720
```

```
agggataacg acttcgagct catgctccag ataacgaccg tcgactggcc caacgacggt      780
gagcttgagc ttatctatca gatgtggagc gtgacccaca gaacccacgc catggtcaga      840
acacggattc cgagggatct cgataaggca aggatgccaa ccgtcaagga tatctaccct      900
gtggctgaga cctacgagag ggacgcccac gacttctttg gagtctactt cgagggcaat      960
gagaagatgg agatgccgtg gatcctcgac gataccgagc aggggctctt cccgcacaga     1020
aaggacttcg acatgctgac ctacgtgaag aagaagtaca agctgctcga caggttcgat     1080
gaggataagg acaactacgt gatttgaatg gtttcacaga atgagctcat tcgggaagcg     1140
agagaaaatg ggatggatct gctcccaatc gataaggaca cttacgagtt gttctttggc     1200
ccacagcaca tggctactga gaacttcagc ataatcctca agatggacgg tcacagggtt     1260
gtgaaggcta tagccaaccc cggcttcctc cacaggggct ttgagaagct cgccgagtac     1320
aggccgtggc acacgaacat agcgctcctc cttagaatct gtgttccaga gccagacgtc     1380
cccgaggcaa tatactcaat ggccgttgat gagataatcg gctgggaggt tccagagagg     1440
gctcagtgga ttagaacaac cgtcctcgaa atggcgaggg tttccgcata tctgttctgg     1500
ataatgggtc tcagcttcaa gctcggtgtc tacactgccg gtcagtgggc tgctgcctac     1560
agggagaggc tgatggccct cttcgagcaa ctgaccggtg ccagggtcta tcacatatac     1620
accatccccg gcggtgtcag gagggacatt ccgggcgaca agtggcttcg ccagctcaag     1680
gacaccgtcg agtacatcag gagcaagtta tcagacttcg acaaccttgt cttcgagaac     1740
tacgttgccc acaggaggct tgagggaatt ggagtgatgg acaagaagtt tgccctcgcc     1800
gaaggcgtca ctgggccaaa cctcagagcc accggcgttc cctacgacgt gaggagggca     1860
gatccatacc tgctctatcc agagctcgac ttcgaggttc ccgtcctgaa ggagggcgat     1920
gccctcgcga gggctttgat aaggcgcttc gagcttgagc aggatcttta catcctcgac     1980
cagctcctcg agatgggacc gccgagcgga ccgtataagg ttgaagatcc caagctcaag     2040
aatctcccga ggtttaaggt tccggctgga gatgcatttg cccacgtgga atcaacgaag     2100
ggcgactttg gtgcctatgt cgtcagtgat ggaaagcaca agccgtacag agtgcagata     2160
aggggcccaa gtatagccca cggagtcagg gttctcgagc agctcttggt tggagcaaga     2220
atagccgacg tccccgtgat attgatgagc cttgacaact gtccaccaga cattgacagg     2280
tgaatggagg ttgattttaa ggtcgcccca gaggagaaag tcaggaagaa gccatcattc     2340
atcaagccct ggatgggcct caagtacctc ttcaagaagc ccgttactat caagatacccc    2400 tacgagaggg tacagatagc taaggactac aggggattcc acaccctaga ctggaagaag     2460
tgtgtcggct gtaacttctg cggccagata tgtccggcga gggcaataga gatgacctgg     2520
atagaagtgg atggcaagat ggagaagagg ccacatccaa agatagacta tggcaggtgt     2580
accttctgtg agttctgtgt cgacgtctgt ccacctggag cgctgggctt catcgagaac     2640
tacatcctca ccaccgagtg gaaggacgag gagctgagc tctttgactg ggttccaatc     2700
catccagaca gttcaggga gataaacgag aagttccccg actacagatt cccggtggag     2760
aagatagagt tcaacaagga aacgaaggag gtcaccctact acctgagaga cggagaggtc     2820
atgaagttca agatactcgg ctacggcatc agaccgccga agccaccgac aaagcctgct     2880
cagaaggcag ccgcaaaagc agcggaaaag aatgatacca agcctgttga aaagcccact     2940
gagaagaagg aagctgggaa gatagaagaa aagaaagaat ga                       2982
```

<210> SEQ ID NO 15

<211> LENGTH: 11208
<212> TYPE: DNA
<213> ORGANISM: Thermococcus onnurineus NA1

<400> SEQUENCE: 15

| | | | | | |
|---|---|---|---|---|---|
| atggagaccc | taatcctcgc | cctcggcaac | gaacttatga | aggatgatgg | tgtcggcctg | 60 |
| aaagtcggca | ggcttttggc | ggaaaaaggt | tacaacgttc | tagaagttgg | cacagacata | 120 |
| ttcatgctcc | agagccatta | cagtggagag | gaaaggctca | taatcatcga | cgccatactt | 180 |
| agcgaaaagt | tcaagccggg | agaaataatc | cacgtgagcg | gcggtgaagt | tttcgagaag | 240 |
| ctgaaagctg | aaattaggag | tgcgcacttc | atggggcaa | tagacgggct | caaactcctc | 300 |
| atggcactcg | atgaaaggct | tgccaacgtt | gaaatccact | tcattggtat | tgttgctaag | 360 |
| gaaatcaacc | tgggtatgga | actgaccgag | gaagttaggg | aagcccttcc | gaaggctgtt | 420 |
| gagctcgttg | aagaattagt | caaaaaataa | atgaagaacc | tctaccttcc | aatcaccgtt | 480 |
| gatcacatag | cgcgtgtaga | gggcaagggc | ggcgttgaaa | tagtcgttgg | tgatgacggg | 540 |
| gtcaaggagg | tcaagctcaa | catcattgag | ggtccgaggt | tctttgaggc | gataaccata | 600 |
| ggcaagaagc | tcgacgaggc | tttggccgtt | tatcctagga | tatgctcctt | ctgttcagca | 660 |
| gcccacaagc | tcactgccgt | cgaggcggct | gaaaaggcag | ttggctttga | ggtacgcgag | 720 |
| gagatacagg | ccctcaggga | ggttctctac | attggagaca | tgatagagag | ccacgcgctc | 780 |
| cacctctacc | tcctcgtcct | gccagattac | atgggctact | ccaacccgct | caaaatgctt | 840 |
| gacaagtaca | agaaagagat | caacattgcc | cttgacctta | agaacctcgg | aagctggatg | 900 |
| atggacgagc | ttggtgcaag | ggccatccac | caggaaaacg | tcgtcatggg | tggttttggc | 960 |
| aagctccccg | acaagactac | gctggagaag | atgaagaaga | ggctccagga | ggcccttcca | 1020 |
| cttgcagaat | acaccttcga | gctgttctcc | aagcttgagc | agtacgagga | agtcgagggg | 1080 |
| ccgataatcc | atatggccgt | caggccgagg | ggagacgtct | acggcatata | cggcgacgcc | 1140 |
| ataagcgtca | gcgacggttt | cgagttcccg | agcgagggct | acaagaagca | catggttgag | 1200 |
| cgcgttgtgg | agcacagctt | cgccaagcac | agcttctaca | acggggagaa | gcccttcatg | 1260 |
| acgggagcca | tatcgcgcgt | tgtcaaccat | gctgataagc | tctacggaag | ggcaaaggag | 1320 |
| ctctacgaga | gccacaagga | cttactcagg | ccaaccaacc | ccttcgccaa | caacctcgcc | 1380 |
| caggcgcttg | agttagtgta | cttcatggag | aggggcatcg | accttatcga | cgaggccctc | 1440 |
| gctaaatggc | cgataaggcc | gagggacgag | gtagatgtaa | aggacggctt | cggtgtcagc | 1500 |
| accaccgagg | caccgcgtgg | aatcctcgtc | tacgccctag | aagtcaagga | cggaagagta | 1560 |
| gcttacgcgg | atatcataac | gcccacagcc | ttcaatctcg | ccatgatgga | ggttcatgta | 1620 |
| cgcatgatgg | ctgagaagca | ctacaacgac | gatcctgaga | ggctgaagct | ccttgctgag | 1680 |
| atggtcgtca | gggcctacga | cccgtgcatc | tcctgttcgg | tgcacgtggc | gaggctttag | 1740 |
| atggagggga | aggttcgtat | agggttttac | gctctcacct | catgctacgg | ctgtcagctc | 1800 |
| cggttcgcca | tgatggacga | gatacttcag | ctgctcccga | acgctgaaat | cgtctgctgg | 1860 |
| tacatgcttg | accgtgacag | cagtgaagat | gagcccgtcg | atatagcctt | catcgaagga | 1920 |
| agcgtttcaa | cagaggaaga | ggttgaactc | gtcaagaaga | tacgcgagaa | cgccaagata | 1980 |
| gtcgttgcag | ttggggcgtg | tgcaacccag | ggtgggttc | agagctggga | gaaggataag | 2040 |
| agcctcgaag | agctatggaa | ggccgtttac | ggcgatggga | aggttaagtt | cgagccgaag | 2100 |
| atggccgaac | ccctcgaaaa | actacatcaa | ggttgactac | gcatctacgg | ttgcccacct | 2160 |
| gagaagaagg | acttcatcta | tgccataggt | accttcctcg | ttggttcttg | gccagaggac | 2220 |

```
atcgattacc cggtctgtct tgagtgcaga ctgaaggdta acacatgcat tctcatcgag    2280
aagggcgagc cgtgccttgg cccgataacg agagcgggct gtgacgcaag atgcccgagc    2340
tacggaatag catgcatagg atgtagaggg gcgataggct acgacgttgc atggttcgac    2400
tcacttgcca ggacgttcaa ggaaaagggc ctcaccaagg aagaaatcct cgaaagaatg    2460
aagattttca acgcacacaa tccaaagctg gaggagatgg tcgataaggt ctttcagttt    2520 caggggggtga aagaatgaat gaacgaggct cacgtctgca tgtgtcacga caatccctac    2580
gcccttgaca gggtcaaggt tctcagagtg taccgtttaa cagaaacaga gaagctattt    2640
ctgttcaggt ttgaagatca agagatagcc gagaactgga cctttaagcc aggacagttc    2700
gttcagctta ccatacccgg tgttggcgaa gtcccgataa gcatctgctc gtctcccatg    2760
aagagaggat tctttgagct ctgtatcaga aaggcgggaa gagtcaccac agttgttcac    2820
aagctcaagc cgggcgacac tgtccttgtc cgcgggccgt acggaaacgg cttccctgtc    2880
gatgagtggg aagggatgga cctactcctc atcgccgcag gattaggaac agccccactc    2940
aggagcgtct tcctctacgc catggacaac cgctggaagt acggaaacat aaccttcatc    3000
aacaccgccc gttacggaaa ggacctcctc ttctacaagg aacttgaagc catgaaggat    3060
ctcgcagagg ccgagaacgt ccagataatt cagagcgtaa ccagagatcc tgactggccc    3120
ggcagacatg gaaggcctca gaagttcata gtcgaggcca ataccaaccc gaagaacacc    3180
gcgatagcta tctgcggtcc gccgaggatg tataaggcgg tcttcgaggc gctcatcaat    3240
tacggttacc gccctgagaa catctatgta acgctggaaa ggaaaatgaa gtgtggaata    3300
ggcaagtgcg gccactgtaa cgtcggaacg agtactagct ggaagtacgt ctgcagagat    3360
ggaccggttt tcacgtactt cgacatagta tcaacgccgg gactgctgga ctgaatgaga    3420
tacgtcaagc ttccaaaaga aaatacatat gaattttttag aaagactaaa aaacctcgga    3480
aagctgtacg ccccagtgaa aatttccgat cagttctatg attttagaga aattgacgac    3540
gtcagaaaga ttgaattcaa ctacacgaga accctgatgc cgccgaagaa gttcttcttc    3600
gcaccaaggg agaagatgtt cgagttcagc atctcaaaag cagagtatag ggaagtaatc    3660
cccgaagtcg agcccttcgt cctcttcggt ctccacgcct gcgacatcta cggtctgaag    3720
atactcgaca gcgtatatct ggatgagtac ccagacaagt actacaaagt caggcgtgaa    3780
aaaggcataa tcatcggtat aagctgtatg cccgacgagt actgcttctg caacctgctc    3840
aggacggact tcgagcacga cggctttgat ctgttcttcc acgagctccc tgacggctgg    3900
ctgataagga tagggacccc caccggtcat aggatagtcg acaagaacat caagctcttc    3960
actgaagtcg cacaggagga catctgcaac ttcagagagt tcgagaggaa gcgcgcccag    4020
gcttttaggt atcatgagga gtgggacaac atccactacc tcctcgagct ggagatggag    4080 cacccccctct gggagaaaga ggccgagaag tgcttcgcct gcggcaactg cagcacggtg    4140
tgtccgacct gccgctgcta tgaggttcag gacatcgtca acctcgacgg agacacggga    4200
tacagggaaa ggcgctggga ctcgtgtaag ttcaggagcc acggactggt cgcgggcggc    4260
cacaacttca ggccgacgaa gaaggaccgc ttcataaacc gctatctctg taagatgtcc    4320
ttccactgga cacttggaat taacttctgt gtgggctgtg aagatgtgac tgccttctgt    4380
ccggcgggca ttgatttcgt gaagaacctc agaattatag ctggattgga ggatgcatcc    4440
tgcccgtcaa agctgagcga ggaaattcca agaaaggtt ttgcatatgc caacaacatt    4500
agaggtgaag acatatgaat ggcacagaat aattcactcg tgctgtatga tgttcatgag    4560
```

```
accgtggatg tgtgctcaaa cgttggctgt gttaagacca aggccactcc atcaaggctg    4620
ctctttgcgg gttcatggc tggtgcatac atagcctttg gattcatttt tgccatagtc    4680
gctagtgcaa gcttccatcc aaagctgggc actttcccaa acctatctct cttcaagctg    4740
cttctgggtg cagttttccc agtcggtctc atagccgtcc ttcttggcgg tgcggacctc    4800
tggacgggca acgcccatat agtaacactt tcgaaaatga cgggcagggc gagcgttaag    4860
gatgtgctct acaactggat cggcagctac acaggcaatt tcgtaggctc ggtcttcttg    4920
gcattcttgg cagtttacgg aacggggctc atggcaggtg gtttgttcaa ggacgttctg    4980
ataggcattg gcaactacaa agtggcgctc acccccatgga aggccctctg gctgggaata    5040
ggctgtaact ggcttgtgaa cgtggcgata tggctctaca ttcgcgccaa agacactgcc    5100
gggaaggtaa tcgtaacctg gttcccgatc ttcgccttcg ttgccatagg ttttgagcac    5160
agcatagcca atatgtgggc cataagcgcc agcatatttg cctcggacgg tgcgataagc    5220
tgggtccagt tcttccacaa cataatccca gtcacgatag gaaatgccat cggaggcttc    5280
ctctttgtgg gcttctacca ctggtacctc gctgacggta gaaatgccat aaagagctg    5340 attgactttg tcgaggtgct ggcactcttc gtctttatca tggtgcttat cccagcggga    5400
atagcctacg ccctcagcgg tctcggaaac attgccacat ggcttgtgcc actcatcata    5460
agtgtctatg gagttgtgat gacgtattta gtaaggagag cgctgtgaat ggaggagttt    5520
aagattggcc tgtgcccata ctgtgggatg gggtgcaggt tttacataaa gactcttaac    5580
gggcagccca taggaataga gccgtatccc ggtggtgtta atgaaggaaa gctctgtcca    5640
aagggtgtcg ccgccgttga cttcctcaga cacaaagata ggctgaaaaa gccgctcaag    5700
agaactgaaa acggcttcgt cgagataagc tgggaacagg cgataaagga gattgctgaa    5760
aagcttctgg agatacgcga gaagtacggg ccggatacgt taggcttctt ctcaagtgcc    5820
cgttgttcca acgaggagaa ctacctcctg cagaaaatag cccgccttct gggcaccaac    5880
aacgtcgacc actgcgcgag gctctgtcac gcctcaacgg tcgtcggtct tgctcagacg    5940
gttggcgctg ccgctcagag cggctcctac acggacatac ccaaggctaa ggtactcctg    6000
atatggggat acaacccgtc agaaacccac ccggttctca tgcgctacat cctccgcgcg    6060
agggacaacg gggccaagat aatcgtcgta gatccgagga agacgaggac tgtctggttc    6120
gccgatatgc acctccagct taagcctgga acggacatag tcctagccaa cgccatgatg    6180
cacgtcatca ttgaagaaag gctctatgac agggagttca tcatgaaccg gacgaagggc    6240
tttgagaagc tcatagcagc tgtccagaag tacacgccag aatacgccga ggaaataacc    6300
ggtgttcccg ccaagctcat cagagaagcc gctataacct ttgctactgc cggacggggc    6360
atcgtgatgt gggcaatggg actgacgcag cacgtcactg gggcggccaa cgttaaggcc    6420
ctcgctgatc tggctctgat ctgtggctac gtcggaagag aaggaacagg tctcttcccg    6480
atgcgcggtc agaacaatgt tcaggggagca tgtgacatgg cagccttgcc aaacgtcttt    6540
ccaggctatc agaaggtaac tgacgacgag aagaggaagc acgtggcgga aatttggggc    6600
gttgaagatc tgccctcgaa gccgggcctt actattccag agatgattga tgcggctgct    6660
aaaggcgagt tgaaggcact ctacataatg ggcgagaatc cggtcatgag cgatccgaac    6720
acgaagcacg ttatcgaggc tctcaagaac ctcgaacttc tcgttgttca ggatatattc    6780
ctcaccgaaa cggccgagct ggctcactac gtgctcccag cagccgcata cgccgagaag    6840
gaaggatcat tcaccgcgag cgagaggcgc gtccagtgga acttcaaggc gattgagccg    6900
ccaggagaag ccaaaccgga ctgggagata ctgacgatgc ttggaaaggc tctcggcctg    6960
```

```
ccaaagttcg actactcaga cgttgaagat attacgaggg agataaccct cgttgctccg   7020
cagtaccgtg ggataacccc cgagaggctc aagcgagagg ttatgggtgt gcagtggccg   7080
tgcccgagcg aggatcatcc tggaacgccg aggctgcacg tcgagcgctt cgccacccc    7140 gacgaaaagg ccaacataat ccccgtagag ttcaagccac ctgcagaaga gcccgatgag   7200
gagtacccat tcatactgac gacattccgc atcgtcggcc agtaccacac actcacgatg   7260
agtaacagga gtgaaagctt gaagaagcgc tggtccagcc cgtacgccca gataagtccg   7320
gaagatgcaa agaagctggg tatacaggat ggtgaaatga taaggatagt tacgagacgt   7380
ggaagctaca cctgcagggc ggtcgttact gaagatgtct cggaaggggt gatcgcagtt   7440
ccgtggcact ggggggccaa tatactcacg aacgatgtcc tcgatccaga agcaaagatt   7500
cccgagctga aggtggccgc atgtaggggt gagaagattg gggggtgctg aatggagaaa   7560
aagctgttca taaacctcgg gcgctgcatt gcctgccgcg cctgcgaggt ggcctgtgag   7620
aaggagcacg gaatttcatt catcacggtc tatgagttca gggacatagc ggttcccctc   7680
aactgccgcc actgtgagaa ggctccgtgt atcgaagtct gcccgacgaa ggccatctat   7740
cgcgacgaag atggcgcagt tgtgatagac gagtccaagt gtatcggctg ctacatgtgt   7800
tcggccgtct gccctacgc gattccgata gttgacccga taaaggagct ggctgtgaag   7860
tgtgacctat gtgccgaaag aaggaaggag ggcagagatc cgctctgcgc tgcggtctgt   7920
cccaccgatg cgataatcta cgctgacctc aacgagctga tggaagagaa gaggaggcgc   7980
aaggccgagc gcatcgtcga agcccagagg aaggcggtcg aaacgctcgc ctacttcggg   8040
tgagtgctga aggtggagct ctgtgtgggg tgtgggttt gtgcaaaggc ctgcccccac    8100
tcggccattt cagtttttga agatagtgtg aggaggatag tcttcgaccc gaagaaatgc   8160
gaagaatgct cctttgagtg caacgaagcc tgcccaacgg gggcgctgga agggaagtca   8220
gacaaagggg agctggtctt tgagtttgcc tactgtgcca tctgcgggaa aaggctcaac   8280
atcgtgaagg aagaagccga atatcttgca aaaaagctga ttgagctggg tgaaaaccct   8340
gagattgcct ttctctgtga tgactgcaag aggaaaaggc tgtttggcgt tgccaacaaa   8400
tatgaggctt acctggggtg aatgagcggg atgaggtttg cgttcctgtg tagggaaaga   8460
ccagaaccaa ctgggaagaa gatagccgtt atcggagccg gaccggcagg cttggcggca   8520
actggctacc ttgtctgtca gggtcatgag gttcatgttt acgacaagtt gccggagcct   8580
ggaggattaa tgctatttgg cataccagag ttcaggattc caatataccg cgttagagaa   8640
ggctatgaag aattagaaag ggtctacaat gtcaagttct tcaccagaac caaagtgtac   8700
ttcgggaatc tggaaggaga atcaggagac gagttcgttg agaacagggt agacttcaag   8760 gaactcgtg agaagtacga tgcggtacta atagcaacag gaacgtggaa gtgctggatt   8820
ccaaacattg agggagcgga gcttgagggt gtcttcccgg ccctcgagta tctctttagg   8880
ataaagagcg ccaagctcgg ccacatggat tggggcaagg tcacaccagt ggagggcaag   8940
aaagtgctgg tcgttggtgc cggccacaca gccgtcgatg ccgcattgga gagcgttctc   9000
ctcggagcgg ataaggtgta cctcagttac cgcaggacga aagggaggc tcctgcgggg   9060 gcctacgaga ttaacctcct ccagcagagg ggtgtgaagt ggctggagag gacgatgccg   9120
gtcaggataa taggtgagaa cggaaaggtc agagctgtgg agctggtgaa gaccaagctc   9180
agtgaacccg acgagagcgg caggaggaga cctgttccaa tagaaggttc gaacttccag   9240
atagacgtgg attatgtcat cttcgccgtc ggtcagagcc ccactccacc cttcgcagaa   9300
```

```
gagatcgata tagccgtcga taagaagggc aggatcgtag ttgataacag gcacatgacg    9360
agcagggaag gtgttttcgc cgcaggagac gtcgttttag gcccgtcaaa ggttggtaag    9420
gctgttaagg atggcctgta tgctgctgag gccatgcaca tgtggctgat ggggaggtga    9480
atgacgagga gaatccttca cgttgattac agcctttgta ttggctgtga gacgtgtgag    9540
gcagtctgtg acttcctcca cggtggcaag cccaacataa ggatttacta cactgtcacc    9600
ggacttccga ttccaataaa ctgccgccac tgcgagaggg caccctgtat ggacgtctgt    9660
cctgcaggtg caatttaccg cgacagcgac ggagccatca taataaaccc tgacaagtgc    9720
ataggctgct acatgtgtct tgccgtctgt ccatttggcg tgccgagctt tgacgtcaag    9780
actaaggcag tcacgaagtg cgatatgtgt gccgacagga aaggcttggg catggaacct    9840
gcctgcgccg agatgtgtcc cgcagaggca atattctttg gaaagcccga agaggtcgag    9900
gacaggataa gacgcaggac tgccgagagg atagcacgcg agaggatagc tgccgtagac    9960
atggaaggtg ttgggaggat gctttaaatg ttgtgggagt cccagatccc cataaatcag   10020
gtgttcgaac ttcgctgcag atccatgaca tacttcggtg ttggagccat taacaagttc   10080
tacgacatag ccaaggatct taaggaaaac cgcggcataa ccaaggtcat tctcgtcact   10140
ggaaagagtt catacaagaa gtgtggcgcc tgggacgttg tcaagcccgc ccttgaggag   10200
tacggtattg agtacgtcca ctacgataag gtcggcccaa acccaaccgt tgatatgatc   10260
gatgaggcca cccagctcgg taaagagttt ggagcccagg ctgttattgg cattggtggt   10320
ggaagtccaa ttgacagcgc caagagcgtt gcgattctgc tggagtacac cgacaagact   10380
gccagggacc tttacgagct taagttcacc ccaacgaagg ccaagcccat catagccgtg   10440
aacacgactc acggaactgg aactgaagtc gacaggttcg cagtggcttc gattccggag   10500
aaggagtaca agccggccat agcctacgac tgtatctacc cactctactc catcgacgac   10560
ccggcgctta tgacaaagct tccggccgac cagactcgct acgtaaccat tgatgccctt   10620
aaccacatca cagaggccgc caccaccaag tttgctagcc cttactcaat acttctcgcc   10680
caggagaccg ccaggctgat attcgactac ctcccagagg ccctggctca cccggacaac   10740
ctgcaggcca ggtactacct gctctacgcc tccgcgatag cgggtatatc cttcgacaac   10800
ggcctgctcc acttcaccca cgctcttgag cacccgctca gcgccgtaaa gccagacctt   10860
ccacacggac ttggcctcgc catgctcctg ccggcagtta tcaagcacat ctacccggcc   10920
accgccagga tactcgccga ggtctacagg ccactcgttc cagaagctaa gggagtcccg   10980
ggagaggctg aactcgtcgc aaagaaggtt gaggagtggc tcttcaacat cggaatcact   11040
cagaagctga ttgacgttgg cttcactgag gaggacgttg ataagctcgc cgaactcgcc   11100
atgaccaccc caagcctcga cctgttgctt tcacttgccc cgattgaggc taccaaggag   11160
accgtcgcgg ccatctaccg cgactcactc tacccgctta caagtga              11208
```

<210> SEQ ID NO 16
<211> LENGTH: 4986
<212> TYPE: DNA
<213> ORGANISM: Thermococcus onnurineus NA1

<400> SEQUENCE: 16

```
atggaggtaa tttttctttt tattgtcatt attctgtcag ttgcatcttt cattggagtc      60
ttttcgagga gcgcaatttt aacgaagtta gtaaatgctc tctccgctct tggctcattg     120
acaatagcct atgccgggat tgtaggtctt aaagagagcg ttgaattaaa tatcactctg     180
ttacatctga aatcggattc cattatcaat gcgttctcaa ctctaacact caaagtcgac     240
```

```
ccgctgtcag gcttttcat gataatactc ggaattctgg gcttctgtac atcggtttat      300
ggtattgcat acttagacat gtataaagga gacaagagac tatatgcctt caactatccc      360
ctcttcctgc tcttcatgtt ccttgttctc gtctcatgga atctcttgtg gttcgttgtg      420
ttttgggaac tgatgactct cttctcccag ttcctggtag cgtttgaaag gaacgagaag      480
actctcattg cgaccctcaa gtacttctgc atgactaaag ccgcagcaga ctttatgctg      540
atagccatag tattggtact cataacaatc tctggcggag gtgattacga tatcctctcg      600
tcccagctcg taaactattt ccgctctcat cctctggaga tgtatcttgt aagtgctgga      660
ttcatgatcg gacttggtgt caaggccgcc cttgtgccgt tccacgtatg gcttccagac      720
gcatacgtgg aggcaccaag taacgtctcg tcattgctca gtggggccat ggaaaaaatg      780
ccagtgtata tgatgttccg ctttttcctg agtttcaccc cactaacccc taatattggt      840
ctactcatag cactgttcgg aacattaacc ctgttttttg gtacgatgta cgcactaaag      900
caaacagact caaagcgcct actggcctac catagtgtcg gccagatagg ttacgttgtc      960
tttgcccttg gggcagggat atatctcctt tccaaggggt acaccacatt cggagctctt     1020
gcccttatgg catccctatt ccacgctctc aaccatgcat tcttcaaggg actgctcttc     1080
ctaacagcag gctcgatcct ttatagaact ggaagcaggg atttggacca cttgggagga     1140
ctagcgagat ttatgccgat aacggcattt gctgcactga taggttctct ttccatagct     1200
gggatgccac cattcaacgg cttttgttagc aagtggatga tatacgtttc aacacttccg     1260
actccgactc tcgtttccct gtttggggcc ctagcactat tcataagcgc tgtaacaacc     1320
gcatctttcg ttaagtactt cacttccatc tttgtaagac cgcctgccaa ggagataacg     1380
gtcaaagaag tcccagtatc aatgtgggcg tcccagttga ttctcgcagt tctttgtgta     1440
atttttggtg tttatccagc attgccactg gaagcaatct caaaagcggt tgactcagta     1500
ggcgtgacca ctccatcaat cacggtcttt cccggtctca tagtgtccga cggtattgga     1560
aacatagctc ctctggctct cctggtattc tccggagctc tgaccgcagt gttactagcc     1620
attttcccat acaaaatcag tcttccggtg tggacaactg gcacgagacg gtccctggcc     1680
atgaggcttc cagcgagctc atactatgcc tcctttgagg aagaattcga ggatgtttat     1740
agctggggag aatggtgtgt atgtaccacg aaaagactat gggacgccac aaaagccgtc     1800
ttgtccaact ttgaggaagt atccttcgac ttggacaaga tgatgactgg agcttggcta     1860
atgctcctta tactccttac aatactcggg ggtgttctgt tatgaatgaa tgcagtttat     1920
gctgccctca atctaatctt catagtactc tttgctccgt tattagacgg aatcgagagg     1980
aaagtcaaag caagacttca gtcaagacaa gggccgccgt taatccagac gtggcttgat     2040
ttattaaagc tcttcagaag gccaaacgtc aggcctaggg agtccgtaag atggctgttc     2100
gaaccagcac cagcaatagc gcttgtatct gtattggcgg cgtccctgtt catcccatca     2160
ctgcttcctg gctcttttaga cacatggggg gatataatcg ccttcatata cctctcaacg     2220
ctctcagccg tcgccatagc tctcggagcg ttctcaactg gaagtccata tgcccaaata     2280
ggatcccaca gagaagtttc aatcataatg gcagaggaat tctccttggc ttttatagtg     2340
gccgcactcg cagcatccag tggaggtctc tcgttctcgc gacttttccc cctccaacta     2400
aaagtatcta ccataacagg tgctctggca ttcgcagtta tggcatacgt cgcgggagcc     2460
agaatcccat ttgacgtcgc tgaagccgaa ccagagatag tcgagggtcc cttcatagag     2520
ttcagcggga aaggcctggg aatgttaaag ctctcaatct acgtgaaacg gctacttctc     2580
```

```
accacgatac tcctgaactt cttcctaccc caagatggca cagtgagagt actagtctac    2640
gtcattggac tagtcatcat atcagttgtt tacgcgtcaa ttgaagccca ctatggaaga    2700
ttcaggacta aagacgccgc cagattcctc aagcgttttg caatagttgg aatcctaagt    2760
tggattttgg gagtggtggg gtggtaaatg gtatttgata tcctcaaagg atgtaaaata    2820
ctggagcaca atgataagat gacagtcgcc gaggtcggcg ccagcaatat acgggagatt    2880
gcaagggcgt tattcgagag gggttattac tactctagtg gcatgggagt agacgaacgg    2940
cccataaacg ggaggtttgc aatgtaccac atattcaact gcgatacaga gggaagatat    3000
gtggttctca agataacatc ccccgaaggg agccctgagg taccgtcaat aaccccctgtt   3060 atcaagggtg ctgaatggtc agagagagaa gccatggaca tgctcggcat agttttcagt    3120
gggcatccaa agcccgaaag gcttattcta ccggacgatt ggccagaagg agtctatccc    3180
ttgagaaaag actttcctta caacaaaaag cttccaccgt caaaacccat agaaaaagaa    3240
agggagcaca aaaagacgt catggagata cccctgggac catatcatcc ctcccttcac     3300
gaaccagagt attttgagct ctatgttaaa ggagacaaag tcgtagatgc ggaatacagg    3360
ggatttcaca tccataggggg aatggagaag cttgctgaat cacgaatgac aataaaccaa   3420
atcccattcc tcgcggagag gatatgtgga atctgtggtt gcacccattc cgccgcatac    3480
tgtcaggcag ttgaggatgc tgctggcatc tacgttccgg agagagcaca gtatataagg    3540
acaataatgc ttgaggtaga gagaattcac agccacctcc tttggttcgg ggttgtatgc    3600
catcttctcg gctttgacag cggcttcatg cacatctgga gggctagaga atacataatg    3660
gacatagcag agctcataac cggcaacaga agacctacg gaataaatat tgtcggaggg     3720
gtaagaagag acatcacgga ggataaaaag gaaaaaacgc tgaaacttct ggacatggtt    3780
gaaaaagaga gcagggaagt acttgataac atcgctgaga tgaaggagct cagagaaagg    3840
atggagggtg tcggagttct accgaagaaa gaggccaggg agataggtgt ggtcggtccc    3900
atggccagga gctctgggat tgatactgat gtaaggcgag accatcccta cgcggcttac    3960
aaggacttgg acttcaaagt cccggtttac aaagaagggg acgttttgc aaggttcctc     4020 gtaagatacg aagaaattt tgagagcttc aatatgataa gacaggccct ggaaaatatg     4080
cctccaggag aactgataaa tgacgaatat gagattcctc cattcaaact cggtatcgga    4140
gtcactgaag ctccacgtgg ggagaacatc cacgccgtga acatggggg agagaacatg      4200 atttaccgct ggcatccaag agctgcaacc tataacaacc tcccggcggt tcctataatg    4260
ctcagaggga tgacgttgc agatgctccc taataatag ccagcataga cccatgcttc      4320
tcctgtacag accacgtctc aataattgat tctgaaagcg ggaagattct gtggagaggg    4380
ccgcttaagg agggcgtgag gagggtctga atggtaaaaa atagtctatg gttttttcat    4440
ctcaactccg gctcgtgtaa cggctgtgat atagagatcc taaatatctt tgcaccacga    4500
aacgatgttg aaagactcgg gataaagctc gttggctctc ccagacatgc agacgccata    4560
gcatttaccg gaccaattac aagggagtgt ctgccaaagg ttattgacgc tctgaaagcg    4620
gttccggagc caaaagtggt tctggccata ggagcgtgcg cctgtggagg gggcatatgg    4680
tatgatactt actccgtaat aggtggtgtt aagagctct acaggattct aaaagaagaa     4740
tacaacatgg agcctcccgc gacggttttt ataccctggct gtccccaaa gccagaggcc    4800 ataatctacg gtgtggctgt tgctagtggg atgctagagt caaaacagaa gaagactgtc    4860
tatgtcgagc cggaggaatc tgtggcaaat gagaagctaa tgatcgccga gctcataagt    4920
gaaacagaaa agacgaggca ctttatgccg ggaattgtca tcagggggt tgaggatgag    4980
```

```
                                                            ccttga                                                    4986

<210> SEQ ID NO 17
<211> LENGTH: 3447
<212> TYPE: DNA
<213> ORGANISM: Thermococcus onnurineus NA1

<400> SEQUENCE: 17
ttgagtgaga ttaccctcaa caaagtgtgc cgaatcgccg gtgaggcgaa gctcgtgctg      60
tatgaggaaa acggaacagt tcaagatgca ctcttcatcg ccactgcccc aattagggga     120
tttgagaagc ttgtagtagg caaaaatcca cttttcgcgg tcgaagctgt catgagaatc     180
tgcggtctct gtcatgcgtc ccacggtata gcgatgagcg aggccataga aaatgccatt     240 ggataatac caccaagaaa cggaatactg atgagagaag ccctcggcct cgtgaacagg      300
attcagagcc acatgctcga gttcctcatg gttgctgggg acctgctaat cgaggagaaa    360
agggaagaag ttctgttcca gctcatggac ttccacgcca agatcagcga ctaccttctc    420
aagatgggag gcgcagcaac acatccccca aacctcaccg tgggaggaat gttctctgtc    480
cccaagtgga gcgtcttcaa caacctcaag gcacgccttc caaagctgac cgggcagtgg    540
gaagagatag cacatttgct gaccgatgag gacatccaga cagaagttgc tgatgaactc    600
agggagaaga aagcggaaaa caactacctg gtaagcagcc tgttctacgg ggacaggttc    660
aacataaacg ccgagagaat tgagacaatg ccctattatg aatacagaaa ggacaacccc    720
cactcaaagg agtccaccac actcatagcc ttctacggtg gggaaaaggt tgaagctggc    780
ccaagggcaa ggatgaaagt ttaccgggag tttacagatt cttccctcta tggccttcac    840
accgcgaggt tcaggatac aacgctggca ctcattaggc ttgaagaaat ccttgacagc     900
ataaagatgg acgagccgtt cagaacgaag aacatagttt tcgggccagg caagggtgtt    960
ggagtctacg aggcaccaag gggaacactc atccacttga tcgaacttgg agacgagggc   1020
agggtggttt cctccaagat aatcgtcccc acaatgttca acattcccgt gatggaggag   1080
atggcaaaag gtctgagcgt taaagcggcc gaggccgtta tgcgcctata tgacccatgt   1140
attccatgta cgacccacgt tgtgaggttg gggggatgaa tggagaagct taaggttctt   1200
catgttgatg tagggggttg tgagggatgc aacgtcagta tcattcgcgc atatccaaag   1260
ctcatggact tgatagagct cgacatatca tacctgcgga aggatgagtg taagctcgac   1320
gagtacgacg tggcgataat aaccggtgga gcatgtatga acgaaccaag gattcttgaa   1380
gagctaaagg agataaggga aaaagctcac actgtggtgg ccttcggttc gtgtgcaacc   1440
ttcagcggga tattgcgctt ctgccgcggc gggcaggagc caaggcccga ccacaggaac   1500
ttccagccca taaacagcgt gattaaagtt gattactcca tcccgggctg cccgccaaca   1560
ccacagatgc tccagtcctt cttcaagttc tacatcaacg gtgacgagag aaggctgagg   1620
ctcttcaagg tgagtgccga cataaagaag ctgagcggct tgacctgat agacgatata    1680 gtgcttacgg gcctctgcat aggttgtggt gcctgtgagc tgtcgtgccc gaccaacgca   1740
atcaagctga tagacaagag gcctaacctc gttcaggaga agtgtatccg ctgcggcacc   1800
tgctatataa ggtgtccgcg cgcctcacag attctgtcca tgggtggtgc gagatgaatg   1860
atgagcgttt cagaaaatct tttgggaaac gtctttggaa tttatcttgc gcgggcaacc   1920
gatgaggaaa tactcaaaag aaaggttgcc agcggcggtg cggttacagc cctcttagcc   1980
tacgccctgg agaagggcct catagatggc gttgtaacgg ccaaaaggac agaggggttg   2040
```

```
gagggtcagg ctgtagttgc gaggacaagg gaggagctcc ttgaaactgc cggaaacaag    2100
tggagcatag tgcccttcgc ctccaggatg aaggccaaga tagaggagga agacctaaag    2160
aacgttgccg tggtctgcct ccoctgccag gcccagttct tcggccagat gagggacttc    2220
ccactcctgg aaagcgattt cggagagagg ataaagtaca tcgttagtct cttctgcata    2280
ggaacattcg cattcgaggc attcctcaac tacctcagga tgaagcacgg cataatggcc    2340
caggatatca aggacatagt ccttaagggg gacttcctcg agatatacca cggcgattca    2400
gtgctctcac tgccgataaa agaggtttac tcatacctcc aagccggctg tctggtctgt    2460
actgactaca ccggaacctg gagcgacatc tcggccggct tcgtggagag cgagagggga    2520
tggactgtcc tcataacgcg caaccttaag gcagaagagc tcgttaagag cgccgagaag    2580
gacggataca tagagctgcg cgacggctcc cacgtgatgg gagaagtcct caaagcggcc    2640
agggaaaagc ttgcgagagc gcagaagaac atgatgtatc tgctctgatt gataaagaaa    2700
gtgaaaattc tcaagtggca agatgggctc gttcccaccg aggactatat ctgcgtcgag    2760
gagacctttg aaatcttcgc agtacacgaa aaggacgaag agtttctcgc cgaacttcct    2820
gcttcaccca accagctgaa ggaacttgga gccggattcg tcgtgtgcgg aggctatgaa    2880
agaccggagg acatagttga cgtatgggtt gagggcaagg agatttacgt gaagttgaag    2940
gatacccccg ccacgggcga gctggttgtg aaacacaccc cctgcggcga cccctacaga    3000
atgaaggagg gcagaattct cagcaggaag ggcgaggaag tcaaaataac ccccggcctc    3060
gtattgaaga tatcctccac gatgacaacg ctggctgaga cgtggagaaa gacaggggc    3120
acccactggg cggccctctt cgatttgaac gccaatgtcg ttgccttcag cgaggacata    3180
ggcaggcaca acgccgtcga taaggtcgta ggatacgccg tcctcaacgg actcgacctt    3240
gaaaggctta tcctggcatc gagcggcagg atgccatacg gcatggtaag aaaggcagtc    3300
aacgcgggca ttccagtagt ggtgacgaaa tcaccgccga cggacaaggg cgtggagctc    3360
gccagggagc acgggtaac cctaataggc ttcgcgaggg gaaggcgctt caacgtgtac    3420
tccggggagc atcgattatt gttctaa                                       3447
```

<210> SEQ ID NO 18
<211> LENGTH: 8730
<212> TYPE: DNA
<213> ORGANISM: Thermococcus onnurineus NA1

<400> SEQUENCE: 18

```
atggaagagc tttttattct ttcctttca attccgctgg ttggaggcct tttactgttc      60
aaactcgacg gtaaaagagc ggattacttc atgctcatca ctgtcatcct tgccacaata    120
ctcaatctcg cggagtttta tgagttctat tcctctggga tgcctactat acacaaaact    180
ctcgtgagct ccacaaccct cggtgaggtc tacggtctct tgatagaccc aatgagtgtg    240
tgcgttggcc tggttgtgat aacagccgga ctgctttta tgatctatgc aaaagactat    300
atgagcccgg agaacaaaga gcacccagtc tatgaggata agggtaggtt ttacgcttgg    360
atggtgctct ttatcggagc aacactcgca ttcatttact cctcgtcggt tctccagctg    420
ctgatattct tcgaaattat gagcctcgcc tgttgggtg tagcaggcta ttatggaagt    480
aaaaaggcca aagggcagc atataaagcg ttgcttgtta ccaactttgg agcggtgata    540
ggtctataca ccgcggtagg tataggaatc acacaccttc acgacctgag catatttgca    600
tattctggcc tcaatgacag ccttaaactc gtcgttttta tcgggtcat gatagctgct    660
tttaccaaga gtgcccagtt tccgctttat tcatggctcc cagatgcaat ggtcgcccca    720
```

```
acacctgctt cagccttcct ccacggtgca gcgatggttg agatgggtgt ctacctgctg    780
gccagattca tccagttcat gaatcccata cccaaagaag gattttacgt catggcagcc    840
ctcatcatcg ccactcagat aatctgcatc ctgatgtatc ctctccagaa gagcgcgaag    900
aggctgctcg cctactcaac aatagcagag tctggactga tgtacgtggc ccttgcgacg    960
gcagtcctcg ggttgcaggg gggacttcag gcttcaatgt tccagctatt caaccatgcc   1020
tacatcaaag gtctcgcttt cctgacggct ggaacgttca gctacgccct gggaaccctt   1080
gagatggaca ggataaaggg cctcattaaa tccctgtgg tcggctacag ctggaccttt    1140
gccctgcttg gtttagctgg cgttccacca ttcggcgtgt tcttcggaaa gctgggaata   1200
ctcagcaatg ccaaggcaat ggaagagagc gtcctcatca ttgccatgtt tgttttactt   1260
ctcctcgact cagcagtgtt cctcatggtg tctctgaaga ggatacacgg catggtcttc   1320
agcgagggcg gagaagaagt cgagattaca ccactgatga aggctgtgat ggttatcctg   1380
ctcgtcctgg ccatgctggc cccgtacata gcgtatccac tgatcgtcaa agtggggtgg   1440
tgaatgttcg acgtaacgct cactctttca ctcgatagaa ctgcagtgtt cttcgtactc   1500
aacgtcgcga tactcggcat agcggcgcta gttgcatcgt tcagatacat gaggatatac   1560
gagttcaaac caaagatacc ctactaccca acgctcgcca tcttcatagt ctcgatgctt   1620
ctcatcccaa tggtccagga ctggctcagt ttcctcttcc tctgggagat aatgactctc   1680
gcctcatact tcctgataat ctacgactgg ccggaggaga gcgtcaagaa ggccggctgg   1740
aagtacttcg tgaccatgca cctcttcgac acatctcccc tcatgctggc agtgactatg   1800
tactacgcct tccatggaac gttcaacttt ggggccataa cggagtacag caatgccata   1860
gtcgctctct ttctcctggg atttgcggcc aaggccggcc tcttcccgct ccacttctgg   1920
ttaccggacg cccacccggc cgcaccgagc ccggtctcag ccttgatgag tggtgccatg   1980
gtcgaactcg gcctctacgg aaccatcagg gttctcaatg ctgtgggatg gagcgtcgca   2040
acctggatag tctatctcat cggcgctatg gcagtgctca gcatgctggc tgccatattc   2100
agctacgccc tccaggacga cgtcaagagg ctcttcgcat ggtccaccat cgacaacatg   2160
ggctggatgt atctgctcat cctggcaggc ctccttggcg tttcaggagt ggagaagggc   2220
gttgactact acgtcgtggc acatggactc gcgaaggcgg cggcgttcat atcaacgggt   2280
gccctcctct acgttttcgg tacgaggagc ctgaagaagg caaaaggtat gatgaacact   2340
gacagcctca ccgcgggact catgatggcc tcaatattcg ccctcgaagg tgttccgccc   2400
ttcaacctct tcatgaacaa gctcaatgtg ataaagactc tcctgacggt cagcccggcc   2460
ctggcatact tcacggccct tgagtgggtg atagcgttca tactgttcct cagagtggtt   2520
cacgcctaca tcctcagcga aggtgaacca gaggccaaga gaaagcttgc tggaagcata   2580
gccctctccg tgatagtcct gctcatcctc tccatggtaa gccagttcgt ctgcgactac   2640
atatgggtga ggtggtgaat ggagggactc tttacgctcg ccgtcatcct gtatttcctc   2700
tccatacccg cagcgttagc cctcaaaagg agcttcaagg cttcaatcag cattggccac   2760
atactcacgg ctctagcctc catagctctg ttagcattta cctttgtgtc aataccagat   2820
atcctcagcg ggaaggccat agaattcaca tatgacttag gagtggccca gattccgttc   2880
cagattgatg ggctctcgct gataatgtgc ttcatcttcg gcgccctcgg acttgcagcg   2940
tcaatatatt ccccgagata catggcaatc tacgagaagt caggcagagg ctggatgtac   3000
ataaccatat attcagtgtt tatgctctcc atgatactca tagtaacaat agccaacatg   3060
```

```
ttctggttca ttttcctctg ggaggtcatg acgtttacat cgtacctcct gacgatctgg    3120
gaaagcgaca agaggatgt cagaaaagcc ggctggaagt acttcgtgac catgcacata    3180
gtgagcacac tgccactgat aatcgccctc gccctgctgt atgcagacgt tagctcaatc    3240
gagggactta actttgagag tctagcggcc ttaaaactaa gcccagtatt ctacgccctc    3300
ttcctgatag gctttggaag caagtcaggc gttgtcccgc tgcacttctg ggccccggag    3360
gcctatacgg tcgccccgag caacgtctcc gctctaatgg ctggagcact ggagaaggtc    3420
gcggtctatg ccctgataag gactacatgc tttatcatga agccaaacga gactttcgga    3480
tatgcagttg ccctgcttgg aacagtaacc ctgacagttg gaaccctcta cgcgttgaag    3540
cagaccgatg ccaagagact tttggcctac cacagtatcg gccagatagg ctacatctgg    3600
ctcggcatgg gcgttgggat agttttcata gccaggggag atatgtactc agccttcgga    3660
gccatagccc tagcatcaag tctgtaccac ctcgttaacc acacgttctt caagggactg    3720
ctcttcctgt cgacgggctc aatattctac agaacccgca gcaggatct caaccagctg    3780
agaggtctgg ctaaactgat gcccttacg gcgctcttca cattcatagc cgcaatgtca    3840
atagctggaa ctcctccgtt caacggcttt atgagcaagt ggatgattta tcagtcaacg    3900
ttcctctcgg caacggcct gatagtgttc tttggagtga tggccctctt cataagcgca    3960
gcaacgctgg cttcattcat caagttctac acaaccgcat ttggaggaga acctactgag    4020
tttacgaagg atgctgagga agttccatcc cctatgctca tcgccaaggg cttcctggct    4080
tcactctgca tcctccttgg actggttcca agcctcatcc tgccgatact gctttcgcca    4140
ggggcagccc tagccggtat agatgtctca ggactgatgg acacaaacta ctggcttgtc    4200
acgattaaag ctccgcttat gccgacaggg gcagagagct acttcaaacc gctactcttt    4260
gcgacactct tcggcgtgat cttcctcggc atgtacctgc tcttcccaat ctcaaagaaa    4320
acctacagac cctggaccct cggtgagccc gtggcgatgg agcactacaa gttcaaggcg    4380
ataaactact acgaacctt cgaggagtac atccaccgc tctaccacac cggccacgtt    4440
ctcagcgagt tcggatctgc cctgattggc gcagtcgcca atgcgtacgt ctcaacaaca    4500
agggctctcc acagagtatg cgattctata agcaagagtg tggccgggat cggaaaagag    4560
tacgagaaga agtgccccga agtctaccctt gacgaatact tccttgcccc actggtcaag    4620
atagtgaggg tctcaggagt gcttctagat gagggattca tgaggccaaa tgcagcgttc    4680
acaatagccc tggtaactct ggcggttata cttgccctga tggtgctgtg aatgacgctc    4740
gaaaaaattg cattcgcggc cctttcactg atgataatca tcctccttcc gccctcctc    4800
gacggaataa gcagaaagat caaggctacc gtccaagaga ggcaggggcc cccgtcttc    4860
cagacctact atgacctctc aagcctgctc tcaatggagc cgatccttcc aacgacaga    4920
ctgggcttcc tcatagctcc ctatgtggcc tttgcttcag cagtctcagc cgccctgctc    4980
ctccccttcg ggaacttcgt cccagtggcc ttcacagggg acatcttcgt cttcctctac    5040
gtgctggcga tattctcgat atcgatgatg atggcaggct tcctcgtgaa caacacctac    5100
tcaaacgcgg gtgccaacag ggagatgatg ctcatcctca gcgtggagcc gatactggga    5160
atagcgatag gcatactcgc gcttaagacc cactcgctca gcgtgagcgg aattccactc    5220
aacctcagcc tcacaccctc cgttgtcctc gctttcatct tcctcgccta cgcgtctat    5280
actgagtgcg ccttcatacc cttcgacata gccgaggccg aaacggagat acttgagggt    5340
ccactcgtcg agtacagcgg gaagctgctt ggaatcttca gtgggccat gctgataaag    5400
cgcgtagccc tgatatggct gttcgcgagc ttcatagtca ttccagtcat gaagggttc    5460
```

```
gtcgacatca cgacgcccta cggtggtgca gtaacgctcg cggcacagct ggtactcctg   5520
gtggtcttct acgtcatgtc ggccatcata gagtcaacga cggcccgtat gaaggtaatc   5580
caggccatca ggcagaacac ggtgatattc cttgcgggaa tagtcgcgct ggtgatagct   5640
tccctgggat ggtgaatgtc tgaagttatc aagtttaacg aggctctgaa aaagaagcgc   5700
gtacacaggg gagatgaaaa agccaaagta acgcgggagt acttggatga gattatcgag   5760
aagttcgggg agaagataag ggacgtcaag caggccgctt acaaccagtg gattataacc   5820
gtcgagaggg aagaccttcc ggagatagtc ctctacttcc tcaaccaccc ggagtggaag   5880
gagacccagc tctcatcgat ggtggccacc gacgagaggc ccctaaacgg caagttcagc   5940
atcacctact ggctcagcgt taacggaaag gcgggtgact tctatctcgg cgtcagggct   6000
tacctgccgg aggacgaccc gaggttcacc tcgatagcgg ccaagcacag gggcgcgaac   6060
tggtacgaga gggaagccat ggagatgctc ggcctcactg ccgaaggcca ccccgacccg   6120
aggcggctcg tccttccgga cgactggccg tcctgcgtct acccgctcag gaaggacttc   6180
cactactcga acagcccgcc gggggagaag ttctacccct acaaggaacc gaagaaggac   6240
gagatagtcg tcccctacgg accgtatcat gtggcccttg aagaggcagc acacttcagg   6300
ctctatgtta agggagaaac cataacagac gttgactatc gcggcttcta cgcccacagg   6360
ggcatagaga agatatccga gggaaggcta acctacgacc aggtctgctt catagcggag   6420
agaatatgtg gaatctgcgg ctgcacacac tccacagcct actgccaggc ggttgagaac   6480
gccggaggta tagaggttcc cgagagagcc gagtacatca ggacgatagt cctcgagata   6540
gagagactcc acagccacct gctcaacttt ggaatagtct cccacctcgt tggctacgac   6600
tacggcttca tgaaagcctg gaggataagg gagcacgtga tgtggctcgc ggaaaggcta   6660
acgggcaaca gaaagaccta cggaatgctc cttgtcggcg gcgttaggag agaccttctg   6720
gagtacagaa aatccctgat agaagacgtc ctcaagaaga taaagaccga gttcagtgag   6780
ctcgtcgatg aggcaatctc aacgagcacc ttcgtgaagc gccttgaagg cgttggggtt   6840
ctgccctaca aggtcgccaa ggagtgggac gttgatggac cccttggcag gggctccgga   6900
agggacttcg acgtgagaag ggaccacccg tacgcgggcc tacaagtacct cgacttcaag   6960 gtcccagtct acaaggaggg tgacgttctg gcaagggccc tcgtcagaat agaggaagtt   7020
ttcgagagca tctggataat agagcaggcc ctcgaccaga tgcccggagg agacattctg   7080
gcggagtaca aggagatacc cccgtactcg gaagcgatag gcatgactga ggcaccgagg   7140
ggcgagaaca ttcactacgt catgaccggc gagaacaaca aggtctacag gtacagggcc   7200
agggcggcaa cctacaacaa cctgccggct gttcccgaca tgatgcgcgg ctacaccata   7260
gccgacgccc cgctcatagt ggcgagcata gacccctgct actcctgtac ggagagagtt   7320
caggtagtcg acgtcgaaag cgggaaggtt agggttctca gcgagacgga gttcaacaag   7380
ctctccataa aggcctcaag gagggtctga atggccgtga cgctgaagta ccccttcgtg   7440
aagcttgaag cccctccgga gtacagagga attccacaga tagacgcgac cctctgcata   7500
ggctgcggtg cctgcgttaa cgcctgtccg ccagatgcac tcctcaggat agacgactac   7560
aacagaggag ttagagaaat tgtcctcgat gtgggaaggt gcatccgctg tgctcgctgt   7620
gaggaggtct gtcccaccgg agcgatcaag ctcacgaacc tcttcgaggc cgcttcgccc   7680
gacaggatgg accacgtgga ggttgttagg ctcaggctcg tgaaatgcaa aaactgcggc   7740
aggtacgccg acttcactga gaggcaggtg agaaaggccc tccagattct ccccgaggag   7800
```

-continued

```
atcatcgaaa gggaagctct ggaagagaag gtctggatct gcagggactg caggaggaaa    7860
gggacagttg atggaaccat agaagccagc aaggaggtgg ttctatgaat gagcggaaag    7920
ccgaagctcc gctccatatg ggtcttccac ctcaacaccg gctcgtgcaa cggctgtgac    7980
atcgagataa tcgacgtgct cacaccgttc tacgacgtcg agcgctttgg aatcaagcta    8040
gttggctcgc cgagacacgc tcatgcactc ctcgtctcgg gtccgctcac gagacaggcc    8100
tactacggcg ccaaagagac cataaaggcg atgcctccgg agccaagggt aatagtcgcc    8160
atcggaacgt gcacctgtag cggagggata ttctacaacg gctatccagt ctacagaagg    8220
cccgagagcg gtagggaggg aagcgagtat ccacggaggg gaggtatagc ggagctcatc    8280
gctgacttga gggacgaggg cgagaaggtc ggtccggtca tctacatccc cggctgtcca    8340
ccgagaccgg aggagataat ctacggcata gcacagctcg tgggactcgt cgagaagaag    8400
ctcagctatc aggagtacag cgacgagctg gttcccttca agctcccaga ggggccgctg    8460
gaggagcgca tcaggctgac ccttatggag aggctcaggc acctcgtggg atacctcgac    8520
agggaaaaga tcctcgagga tttcatgggg ctcgttaaag aggccgagaa gagcgagaat    8580
cccagggagg agctggccag gctcgtcaag gactacgccg ccaaatgcgg ggacgttaga    8640
ctgggcttct gtatgatgct tctcgaaaga gagtactgga gggtcaaaga tgccctggat    8700
gctggtaaag agttcgtata ttgggtttaa                                     8730
```

<210> SEQ ID NO 19
<211> LENGTH: 4179
<212> TYPE: DNA
<213> ORGANISM: Thermococcus onnurineus NA1

<400> SEQUENCE: 19

```
atgtttggct actgggacgc tctttacttt gtctttatct ttattatcgg cctcatcata      60
gcatggatgt tgaacgaatg ggccaagaag tctggaatgg gtacgagaga agctggtgat     120
ggcacgaaag tcttcatcag tggtgaggac cggacaagg taatccccgg cttcgagcat     180
tacgaaggtt actacactgg caagaacgtc atgtggggtc tcacatacgc cctcaaaagg     240
ttcttcgccc tcctcaggaa cgagcacaca ggtctgctca ccgattacgt aagctacctg     300
ctcataacga cggctttcgt gctcggagtg atactgattt ggggtgaat gagcatcaag     360
gttcccgctg accagaatag aacaaacgga accacgagtg agcgcgagat gctggagaag     420
agaatagccc agttgtgccg cttcatagga agatcaccct gggtatttca cgtaaacagt     480
ggaagctgca acggctgtga catcgaaatc atagccgccc tgaccccgcg ctatgatgcc     540
gagcgctttg gcgtcaagct cgtgggaagc cccaggcacg ctgatgttct cttagtaaca     600
gggccagtca cagaccagag ccttgaaagg gtcaagcttg tctacgagca gacaccagac     660
ccgaagatag tcatagcagt gggatcgtgc cccactggcg gtagcgtgtt ctatgagagc     720
ccattcacca atgcaccgct gagcaacatc attccggttg acgtctacgt gccaggctgt     780
ccaccaaggc ccgaggccat actctacggc gtcgttttgg cccttgaaaa gctggctaaa     840
atcctgaaag gcgaagttcc ggagggtgaa gagtgaatgg ctgatgataa cagaatcatg     900
gagaatgttg ataatgttag agaaccaacc aaggaagata ctgtcgctga gaccataaag     960
agccgtttcc ccaatgctca cgtggagata cgggagaaca agtgggggaag aaagcgcgtc   1020
tgggtgatcg ttccacgaga agactacaaa gcgctcatga agttcctcct tgaactcgac   1080
ccagaggccc actattcgat aggaatagag caggactacg gggaagagat aggctatatg   1140
agccacatcc tgctgcacta cgacaatgct ccagcagtct cactgctcgt tgatgttaga   1200
```

```
gtacccaaag acgatccagt aattcccgat atcagcgaca tcttcccgat agcactccag   1260
tacgaaaggg aagccgctga gatgatgggc atagtcttcg aaggtatccc cgacagtaga   1320
aggcttttcc ttccggacga cttcccagag ggtatctacc cgctcagact cgacgaaaaa   1380
ggcataccag aagagattgt caagaacgcc ggacacccgt actacctgaa gggggagat   1440 aaatgaatga ccaagaaggt cgagtactgg ataaagatac cgttcggccc aattcatccc   1500
ggcttagagg aacctgagaa gttcatactt acgctcgatg gcgaaaggat agtcaacgtt   1560
gatgttaagc ttggctacaa tctacgtggc ctgcagtgga tagcatacag gagaaattac   1620
gtccagataa tgtacctcgc ggagaggata tgtggtatct gttcgttctc ccacaaccac   1680
acctacacca gagccgttga ggaagcggcc ggaatagaag tgccagagag ggctgagtac   1740
atccgtgcca aataggcga gctcgagagg gttcactccc acctgcttaa ccttggtgtc   1800
ctcggccacg acataggcta cgacacggtc cttcacctca catggctggc acgcgagagg   1860
gtcatggatg ttcttgaagc catctcaggg aaccgcgtga actactcgat ggtaaccata   1920
ggcggtgtga agagacat cgatgaaaaa gggaagcggc tcattcttga tatgataaag   1980
tactacagga gcataatgcc tcagatagaa gaggttttcc tccacgaccc aaccatagaa   2040
gcccgtttga gggactgtgc ggtgataagc aagcgcgtcg cccttgagca gggtgcagtg   2100
ggaccgactg ccagagcttc cggtctaaag gtcgatgcca ggtggagtga gaggcttggt   2160
gtttaccctg acctaggagt taagccagtg atgccacagg acgttacggg agaaaaaccg   2220
cacggtgatg tattcgacag ggcagccgta agaataggag aaatatacca gagcctcgac   2280
atgctcgaac acgcactaga ccagatgcca gagggtaaga taaagacatt cccaaaggac   2340
aacatcttgg ttgccaagct caagattatg gttgacggag agggaatcgg aaggtacgag   2400
gctccacgtg gcgagctggt acactatgtt cgcggaaaga aaggctccga taaaccgctc   2460
cgctggaaac caagggagcc aactttcccg aacctcttcg cagttgccaa gggtgtgaca   2520
ggtgatcagg tggcagactt cgtgctggca gtggcctcga tagatccgtg cctgagctgt   2580
acagacaggg ttgccgtagt acaggatgga agaagagaa ttcttactga aaccgacctg   2640
ctgagactct caataaagaa gacacgcgag ataaaccccg aagttaaagg cgacccaaca   2700
ccggtcggct tcggctgctc gaggtgaatg gacgtaatgg cgaacatcat ttatccggta   2760
gcaggtttaa taggcctta cgctttcgtc tcactggcat cgctcgtctg ggaaggtata   2820
gacagaaagc tcgtcgcaag gatgcagaga agggtaggac cgccgcttct ccagcccctc   2880
tatgacttct tcaagctagc gagcaaggaa acaataatcc ccaacacggc taactttatg   2940
tttagagccg cacctgtact cgccctggca acggccatag cactcctcgc ttacaccccg   3000
atgggctttg ctccactact cgcgagcaag ggagacgtca tcgttttcat atatctcctc   3060
accctcattg gcttcttcaa gatactcggt ggcataagct caggaagccc ctacgcaaag   3120
ataggagctg caaggaagc agcaataatg gtttccagag agcctgccat gatgctggcc   3180
ctattcgcta aatatggcg tcttggaaaa ctcggagtca acaagccatt cagcatggag   3240
gtcttctacc agtacaacat ttgggaaata ggtaccccgc tcagccttat aggtgccgta   3300
atcctccttt acgtcttcgt catttggctg gcaagtgaaa tagaagtcgg atatttcaac   3360
atacccgatg cagaggagga gatagccgag ggactgctcg ccgagtacag cgggcgctac   3420
ctggccctgt aaagctcac gaaggcactg aaaacttaca tagcagcatc gctcgtcgta   3480
gcaatattct tcccctgggg aatagcagat tacttcaacc tcaccggact tccagcaaac   3540
```

| | |
|---|---|
| gtcgtaaacc tgctcttcca tacactcaag gtattcatac tgctctttgc tgtgcagagt | 3600 |
| gtcttcaggg ccactacagg cagactcaaa ataacgcagg cggttgactt cctctggaag | 3660 |
| aacgtcttct tagcttcgct catcggcaca ctccttatcg ccatggaggt gataatgtga | 3720 |
| gtgaggctct ccccactcat ccccaccgtg ctcagaaaca tgttcaaaaa gcctgccacc | 3780 |
| aacctctttc ctgcgactga accagtgccg gttccagata acttcagggg ccagctgaag | 3840 |
| tacaacgtgg acaagtgtgt cggctgcagg atgtgcgtca cagtctgtcc agccggcgtc | 3900 |
| ttcgtcttcc tacctgagat aaggaaggtc gctctgtgga ccgctagatg tgtctactgc | 3960 |
| tcgcagtgtg ttgacgtttg tccgaccgca gccctccaga tgagcgatga gttcctgctg | 4020 |
| gcaagctaca caactacga cgacaagttc atcccgctca agcccgaaaa ggttgaagag | 4080 |
| ataaagaaga aactggagga gcaaaagaaa gcgaaggcag ctgcagctgc caagaaagcc | 4140 |
| atggagaaaa aggaagcagg gaaagaggcc aaaaagtga | 4179 |

<210> SEQ ID NO 20
<211> LENGTH: 2568
<212> TYPE: DNA
<213> ORGANISM: Thermococcus onnurineus NA1

<400> SEQUENCE: 20

| | |
|---|---|
| atgggtatgg cagaaaagcg catatcagtg gtgtgtccgt ggtgttccgt tggttgtaga | 60 |
| ttttacatag taaacgtcaa tggctaccca agaagatcg agttcgacta cgaccacgac | 120 |
| atcaggaacc acggcaagct ctgtccaaag ggtgtcgcag ccttccagca tctcaggcat | 180 |
| ccagacaggc ttaaaaagcc ccttaagagg gttggcgaga ggggtgaagg caagttcaag | 240 |
| gaaataagct gggaagaggc tattaaggaa atcgcacaga agctcagtga aatcaaggag | 300 |
| aagtatggtt cggaggctct tgcttttctc ggaagtgaaa ggtgctccat agaggagaac | 360 |
| tacgttcttc agaagctggc aagggctttg ggaaccaaca acattgaata tgtgtgtagg | 420 |
| atgtgtcagt caacggctgt tgcaggtaag gggatggttc ttggacaccc cggtctgacg | 480 |
| aaccccttcg aggacattct taaggccaaa gttatcgtcc tttggggata caatccagcc | 540 |
| gcaactaatc cggtcttctt cggccagtac attgagaagg caattctcga caacaacgcc | 600 |
| accctcattg tcgttgaccc aagaaaaacg aagactgcca agtacgcaga catacacctg | 660 |
| cagccatatc ccggaaccga ccttgccatt gcgttggcta tgctcaacgt cataatcacc | 720 |
| gaggagctct acgataagga cttcgtggcg gagcgcgcgg agggccttga ggagctcgcc | 780 |
| aagaccgtcg aaaagtacac tccagaatgg gctgagaagg tcagcggcgt tcctgccgag | 840 |
| ctcataagga aggccgcaat caccctttgca acggctggaa ctgccgccct gctgacgaac | 900 |
| gagggagtga accagcacgc caacggaacg aggactgtta tggctatcac tgagatgatg | 960 |
| gttctctgcg gctacttcgg aaaggagggc gtcatgtctg gagctatacc cggtgcccac | 1020 |
| aacggtatgg cgctggtct aatgggtatt ggaccacacg aactgccagg aagattcccg | 1080 |
| ctccacgccg aggagcacaa gaggagaatt gaggaggcat ggggcttcaa gatcccagag | 1140 |
| aagcctggaa tcacttacgt tgaaatgatt gatgcaatcc ttgagggcaa gctcaaggcc | 1200 |
| ctctacgtca tgggaaccaa ccctgccaag gcccttccga acctcaagaa ggctgaggag | 1260 |
| gcctttaaga acatcgagtt cctcgtcgtc caggatatct tccttactga gaccgcgaaa | 1320 |
| tacgccgaca tagtccttcc agcggctgca tggtttgaga aggacggaac cgccataagc | 1380 |
| ttcgagagaa gggttcagag gagctttaag gctgctgacg caccgggaga ggccaagcct | 1440 |
| gactgggaaa tccttgttat gctcgctaag gagctcggct ttggagagta cttcaactac | 1500 |

```
tctgatgcag acgacatcct gagagaaata aacagaatca ttccgcccct tgctggcgcg   1560
acacccgaga ggctcaagaa gaacctcaaa ggctgtatga taccctgccc agacgagaac   1620
actgaggttc cgaggctctt tgtccagggc ttcctcacgc caaacggaaa ggcccagctt   1680
attcctgtgg agtataaaga gcctggagaa gtccccgatg aggagtaccc gttctggctc   1740
accaactaca ggttcgttgg ccacttccac accggaacca tgagccacag gagcaagagc   1800
ctgagcaaga ggtggccaga ggagtacatt gagatcaacg agaacgacgc gaagaggctc   1860
ggcataaagg acggcgacct cgtgagagtc gagaccagga gggcagcgct ggttctcagg   1920
gccaaggtta caccgcacat cagggagggc gtcgttgccg cgccgtggca ctgggacttc   1980
aactacctga ccacggacgt cctcgacgaa tacgccaaga tgccggagtt gaagacggcc   2040
gcgtgtagga tctccaaggt tgaggggtga atgagcaaaa agatatttat cgattttaag   2100
cgctgcattg cctgtaaggc ctgtgaagtc gcctgtgaaa tggagcacgg ggaagcgagg   2160
attagggttt ttgagttccc cgatctgacc agcgtcgcct tcaactgccg ccactgtgaa   2220
aaggctccat gtatggaagt gtgtccagtt aacgcgctct ccaaggacga tgatggcgca   2280
gtcgttctcg atcccctcaa gtgtatcggc tgtctcatgt gcggtctggc ctgtccattc   2340
ggcattccaa agatagacga gtacaacaag ataatggaca agtgcgacct ctgtgcccac   2400
aggagagccg aaggaaagct tcctgcctgt gtctcagcgt gcccaactga ggccctcaag   2460
tacggcgaca taaacgatgt cctctgggcc agagaaggaa agatagtcgc cgagcttaag   2520
gacatcggcg acaggaccaa cgtcctcgag gcctacctca tcagatga                2568

<210> SEQ ID NO 21
<211> LENGTH: 1893
<212> TYPE: DNA
<213> ORGANISM: Thermococcus onnurineus NA1

<400> SEQUENCE: 21
atggccggaa agaaggttcc ctcaaagcaa gtctccataa ctccaggtgt tggaaagctt   60
attgagaaag ccgaggagga tggggtcaag actgcctggc acagattttt ggagcagcag   120
cctcagtgtg gattcggtct cttaggtgtc tgctgtaaga actgtacaat gggaccatgt   180
agaatcgatc cgtttggggt tggcccaact aagggagttt gtggtgcgga tgcagataca   240
atagtagcaa ggaacattgt aagaatgata gcggctggta ctgccggtca cagcgatcac   300
tcaagagatg tagtccatgt attcaagggc attgctgaag gaagttcaa ggactataaa    360 ctaacagatg ttgaaaagct caaagagctg gctaagattc tgggtgtcga acagagggc    420 aagagcgaaa atgaaattgc attggaagtc gcccacattc ttgagatgga gttcggaaaa   480
caggatgagg agccagtaag attacttgca gcaacagcac caagaagag gattaaggtc    540 tgggagaagc taggagtctt accaagagcc atcgacaggg agatatgtct cagtatgcac   600
agaacccaca taggctgtga tgcagaccct gcaagccttc tactgcatgg tgtgaggact   660
gccctggccg acggctggtg cggctcaatg atggccactt atctgagcga cattctcttt   720
ggaacaccaa agccgataaa gtcgctggcg aacctgggag tcttgaagga agacatggtc   780
aacataatcg ttcacggcca caacccgatt ctctccatga aaatagcaga gattgcccag   840
agtgaagaga tgcagaagct tgcagagcag tacggagcaa agggaattaa cgttgctgga   900
atgtgctgta ccgaaacga agttctctca gaaatgggaa ttcaggtcgc tggaaacttc   960
ctaatgcaag agctggcgat tataactggt gcagttgagg ccgtgatagt tgactaccag   1020
```

| | |
|---|---|
| tgcctaatgc cctcattagt tgatgtcgct tcatgttacc acactaagat aataactact | 1080 |
| gagccaaagg ctcgcattcc gggagcaata cacgtcgaat ttgaacctga gaaagcggac | 1140 |
| gagatcgcca aagagatcat caagattgca attgagaact ataagaacag agttccggca | 1200 |
| aaagtctaca ttccagagca caagatgaaa ttggttgctg gatttagtgt cgaggcaata | 1260 |
| cttgaagccc ttggtggaac actggagccc ctcataaaag ccctccagga cggaacaata | 1320 |
| aagggaatcg tcggaatcgt tggatgtaac aatccaaggg tcaagcagaa ctacggtcac | 1380 |
| gtcaccttgg ccaaggagct catcaagagg gacatcctgg ttgttggaac tggttgctgg | 1440 |
| ggaattgctg cagcaatgca tggattacta accccgaag cagctgaaat ggccggtcca | 1500 |
| gggctgaagg cagtatgcga agcgctcgga attccaccat gcctgcacat gggaagctgt | 1560 |
| gttgactgtt cgagaatcct gctggtcttg agtgcccttg ccaatgctct gaatgttgac | 1620 |
| atttcagact tgccagttgc tggctctgct ccagaatgga tgagcgagaa ggcagtggca | 1680 |
| ataggaacct acttcgttgc aagcggcgtc ttcacgcact gggagttat cccaccagtc | 1740 |
| cttggaagcc agaaggttac caaactcctt acgatgaca tcgaggatct ccttggaggg | 1800 |
| aagttctacg ttgagacaga tccagtgaaa gcggcagaaa caatatacaa cgtgataatt | 1860 |
| gagaagagga aaaacttggg atggcccatc taa | 1893 |

<210> SEQ ID NO 22
<211> LENGTH: 2637
<212> TYPE: DNA
<213> ORGANISM: Thermococcus onnurineus NA1

<400> SEQUENCE: 22

| | |
|---|---|
| atgagtgaaa ggctcgtccc cgtggtctgc ccctactgtg gtgtagggtg caggctatac | 60 |
| atcaggagtg ttgatggcta tcccgtaggc atagaatacg ccaaggacat ccccaacatc | 120 |
| tcaaacgaac tcggaaagct ctgccctaaa ggcaacgccg tcgttgagta cctcctcgca | 180 |
| aaggacaggc tcaagagacc cctcaaggcc aaggaacagg gcaagttcgt tgagataagc | 240 |
| tggagcgagg caataaagga ggttgccgag aggctcaagg cttatgccaa ggacgacccg | 300 |
| aaccagctca tgttcttcgg ctctgcgaga acattcaacg agcccaacta cctcgtccag | 360 |
| aagctggcca ggatgctcgg caccaacaac gttgatcact gtgcaaggct ctgtcatgca | 420 |
| ccgaccgtca cgggtctcaa ggctgttttc ggtgccggcg caatgaccaa cacctacaag | 480 |
| gacattgaag aggcaaacgt catcttcatt atcggccaca actacgctga cccacccg | 540 |
| gttggcttcc gctacgtcct taaggccaag gagaggggcg ctaaggtcat agtcgctgac | 600 |
| ccgaggttca ccaggacggc ctggttcgcc gacatattcc tacagcacta cccgggaagc | 660 |
| gacattgcgc tgataaacgg tctcatccac gtcatcatca aggagcggct ctacgacgag | 720 |
| aagttcgtga gggagagatg cgttggcttc gatgaagttg tggcagccgt cgagaagttc | 780 |
| acacccgagt cgtcgagaa ggtaaccggt gtcccggcgg aactcatcat gaagctgca | 840 |
| agaaccttcg cgaccgcagg aaagggtgtc ataacctggg ccatgggtct aacccagcac | 900 |
| acccacggaa ctgaaaacgt caagctcctt ggaacgctcg cggccatttg cggttatcag | 960 |
| ggcaaagaag gtgccggctg ttccccaatg cgcggtcaga acaacgttca gggagcatgt | 1020 |
| gacatggcag ccctgccgaa cgtcttccca ggctatcagg ccgtcactga tcctgaaaag | 1080 |
| aggaagttct ttgaggagtt ctgggggtgtt gagctgagcg gcgaagtgg actgacaact | 1140 |
| gtggaggctg cctacgcggc cgacaagggc aaggtaaagg cctactatgt catgggtgag | 1200 |
| aacccagtca taagcgaggc caacgccaac cacgtgatgc acaccctcga gaagctcgag | 1260 |

```
ttcatggtcg tccaggatat cgtcccgacc ccaactatgg agtatgcaga tatagttctg    1320
ccggccgcgg ccatgctcga gaacgagggt tctctgacca atacagagag gcgcgtgcag    1380
tggagcttcc aggcggtaaa accacccgga gaagcaaggc ccgactggtg gattcttagc    1440
gaggtcggta aggccatcgg ttttgacaag accggatccg gtggattcgt ctacaatgat    1500
gcagccgacg ttctcaggga atcaacgcc tgtactccgc agtatcgcgg tataactcca    1560
gagaggctca aggagaacct tgcaggactc cactggccgt gcccaagcga ggaccatcca    1620
ggaacgaggg tcctctacaa ggagaagttc ctcactccca gcggaaaggc caacctcgcg    1680
gccgttccgg agtacaaggg accagtcgaa atgccggacg aagagtatcc gttcctcctt    1740
acgacccaca gatacgtcgg aatgtaccac accgcaacca tgaccatgag gagctgcgca    1800
ctcaagaagc gctggccaga acccctcgcc gagatacacc cggatgacgc agtgaagctc    1860
ggaataaaga gtggagactg ggttaaggtc gtcacaagga gaggagcata tccgattaag    1920
gcaaaggtca cccgggctgt caagaagggc gtaatagctg tcccgtggca ctggggagca    1980
aacgtcctca ccaacgatgc cctcgacccg gtagcaaaga taccggaaac caaagcctgt    2040
gcctgtaatg tcgccaagat cacagaagaa gaggccagga agctcatgga gaaactccca    2100
ccactcatac ccaagattga ggtcgttagg gggtgaatgg ctagaaagac cgtctttatt    2160
gacttttcaa agtgcatcga gtgccgcgcc tgtgaggtag cttgcgagcg cgaacacagt    2220
ggaatgtcat tcatcagcgt cttttgagtgg caggaaatgg ccgctatggc cctcaactgc    2280
cgccactgtg agaaggctcc ctgtgttgag gtctgtccaa ccaacgccct ctaccgcgac    2340
aaggatggag cagtcctgct cgctccacag aagtgtatcg gctgtctcat gtgcggcata    2400
gtctgtccct ttggaatacc cgagctcgat ctcatcaaca agataatggg caaatgtgac    2460
ctctgcgccc acaggagagc cgaaggaaag cttccagcct gtgttgagac ctgtccaaca    2520
gatgctctca tctacggcga cttcaacgag atagtcaaga agagaaggga gaagtttacg    2580
gagaaaacca tagaactcgc caaaactgca gagcgcatcc cgctgacggg ggtgtga      2637
```

<210> SEQ ID NO 23
<211> LENGTH: 24
<212> TYPE: DNA
<213> ORGANISM: Artificial Sequence
<220> FEATURE:
<223> OTHER INFORMATION: CODH/F primer

<400> SEQUENCE: 23
ggaccatgta gaatcgaycc gtty                                           24

<210> SEQ ID NO 24
<211> LENGTH: 18
<212> TYPE: DNA
<213> ORGANISM: Artificial Sequence
<220> FEATURE:
<223> OTHER INFORMATION: CODH/R primer

<400> SEQUENCE: 24 ttcrttttccg gtacagca                                                 18

<210> SEQ ID NO 25
<211> LENGTH: 21
<212> TYPE: DNA
<213> ORGANISM: Artificial Sequence
<220> FEATURE:
<223> OTHER INFORMATION: Hsp60/F

```
<400> SEQUENCE: 25
atggcacagc ttagtggaca g                                              21

<210> SEQ ID NO 26
<211> LENGTH: 22
<212> TYPE: DNA
<213> ORGANISM: Artificial Sequence
<220> FEATURE:
<223> OTHER INFORMATION: Hsp60/R

<400> SEQUENCE: 26
caaggatttc ctgggctttc tc                                             22

<210> SEQ ID NO 27
<211> LENGTH: 22
<212> TYPE: DNA
<213> ORGANISM: Artificial Sequence
<220> FEATURE:
<223> OTHER INFORMATION: mbh/F primer

<400> SEQUENCE: 27
cacgacatag gctacgacac gg                                             22

<210> SEQ ID NO 28
<211> LENGTH: 22
<212> TYPE: DNA
<213> ORGANISM: Artificial Sequence
<220> FEATURE:
<223> OTHER INFORMATION: mbh/R primer

<400> SEQUENCE: 28
ctggcttaac tcctaggtca gg                                             22

<210> SEQ ID NO 29
<211> LENGTH: 22
<212> TYPE: DNA
<213> ORGANISM: Artificial Sequence
<220> FEATURE:
<223> OTHER INFORMATION: mbx/F primer

<400> SEQUENCE: 29
gcgattcggt atgataccgg ac                                             22

<210> SEQ ID NO 30
<211> LENGTH: 22
<212> TYPE: DNA
<213> ORGANISM: Artificial Sequence
<220> FEATURE:
<223> OTHER INFORMATION: mbx/R primer

<400> SEQUENCE: 30
ccatccttcg ccgaagagct cg                                             22

<210> SEQ ID NO 31
<211> LENGTH: 23
<212> TYPE: DNA
<213> ORGANISM: Artificial Sequence
<220> FEATURE:
<223> OTHER INFORMATION: frh/F primer

<400> SEQUENCE: 31
gtaagctcga cgagtacgac gtg                                            23

<210> SEQ ID NO 32
<211> LENGTH: 23
```

```
<212> TYPE: DNA
<213> ORGANISM: Artificial Sequence
<220> FEATURE:
<223> OTHER INFORMATION: frh/R primer

<400> SEQUENCE: 32
gcaccacaac ctatgcagag gcc                                              23

<210> SEQ ID NO 33
<211> LENGTH: 22
<212> TYPE: DNA
<213> ORGANISM: Artificial Sequence
<220> FEATURE:
<223> OTHER INFORMATION: sulf1/F

<400> SEQUENCE: 33
gcagtacgag gaagtcgagg gg                                               22

<210> SEQ ID NO 34
<211> LENGTH: 22
<212> TYPE: DNA
<213> ORGANISM: Artificial Sequence
<220> FEATURE:
<223> OTHER INFORMATION: sulf1/R primer

<400> SEQUENCE: 34
gagggcctcg tcgataaggt cg                                               22

<210> SEQ ID NO 35
<211> LENGTH: 23
<212> TYPE: DNA
<213> ORGANISM: Artificial Sequence
<220> FEATURE:
<223> OTHER INFORMATION: mch/F primer

<400> SEQUENCE: 35
ctaccggacg attggccaga agg                                              23

<210> SEQ ID NO 36
<211> LENGTH: 23
<212> TYPE: DNA
<213> ORGANISM: Artificial Sequence
<220> FEATURE:
<223> OTHER INFORMATION: mch/R primer

<400> SEQUENCE: 36
ccttatatac tgtgctctct ccg                                              23

<210> SEQ ID NO 37
<211> LENGTH: 22
<212> TYPE: DNA
<213> ORGANISM: Artificial Sequence
<220> FEATURE:
<223> OTHER INFORMATION: mfh1/F

<400> SEQUENCE: 37
gcgaccggta cggcaacctt cg                                               22

<210> SEQ ID NO 38
<211> LENGTH: 22
<212> TYPE: DNA
<213> ORGANISM: Artificial Sequence
<220> FEATURE:
<223> OTHER INFORMATION: mfh1/R primer

<400> SEQUENCE: 38
```
cttgtcagtc atgacgtagt gg                                            22

<210> SEQ ID NO 39
<211> LENGTH: 23
<212> TYPE: DNA
<213> ORGANISM: Artificial Sequence
<220> FEATURE:
<223> OTHER INFORMATION: mfh2/F

<400> SEQUENCE: 39
gacccgaggt tcacctcgat agc                                           23

<210> SEQ ID NO 40
<211> LENGTH: 23
<212> TYPE: DNA
<213> ORGANISM: Artificial Sequence
<220> FEATURE:
<223> OTHER INFORMATION: mfh2/R

<400> SEQUENCE: 40
gcagacctgg tcgtaggtta gcc                                           23

<210> SEQ ID NO 41
<211> LENGTH: 32
<212> TYPE: DNA
<213> ORGANISM: Artificial Sequence
<220> FEATURE:
<223> OTHER INFORMATION: primer

<400> SEQUENCE: 41
cgttgtcttt gcccttgggg cagggatata tc                                 32

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
ggcaattgct tggactgccg aaaagccaat ggc                                33

<210> SEQ ID NO 43
<211> LENGTH: 33
<212> TYPE: DNA
<213> ORGANISM: Artificial Sequence
<220> FEATURE:
<223> OTHER INFORMATION: primer

<400> SEQUENCE: 43
gaagaaatcg cagagggcgc ctatgactat cag                                33

<210> SEQ ID NO 44
<211> LENGTH: 32
<212> TYPE: DNA
<213> ORGANISM: Artificial Sequence
<220> FEATURE:
<223> OTHER INFORMATION: primer

<400> SEQUENCE: 44
gctcctcgct tactcaagcg ttggacaaat gg                                 32

<210> SEQ ID NO 45
<211> LENGTH: 33
<212> TYPE: DNA
<213> ORGANISM: Artificial Sequence

```
<220> FEATURE:
<223> OTHER INFORMATION: primer

<400> SEQUENCE: 45
ggactgctct tcctgtcgac gggctcaata ttc                              33

<210> SEQ ID NO 46
<211> LENGTH: 32
<212> TYPE: DNA
<213> ORGANISM: Artificial Sequence
<220> FEATURE:
<223> OTHER INFORMATION: primer

<400> SEQUENCE: 46
ggacgcactt aaagtcggcg tagccctttg cc                               32

<210> SEQ ID NO 47
<211> LENGTH: 32
<212> TYPE: DNA
<213> ORGANISM: Artificial Sequence
<220> FEATURE:
<223> OTHER INFORMATION: primer

<400> SEQUENCE: 47
aatttaccac cccaccactc ccaaaatcca ac                               32

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
aatggggagg ctgaaactac tgggcaaggc                                  30

<210> SEQ ID NO 49
<211> LENGTH: 29
<212> TYPE: DNA
<213> ORGANISM: Artificial Sequence
<220> FEATURE:
<223> OTHER INFORMATION: primer

<400> SEQUENCE: 49
tggcccaggc gatttccttc accgacagg                                   29

<210> SEQ ID NO 50
<211> LENGTH: 31
<212> TYPE: DNA
<213> ORGANISM: Artificial Sequence
<220> FEATURE:
<223> OTHER INFORMATION: primer

<400> SEQUENCE: 50
aattcaccac cccaccagcg ctattatcag g                                31

<210> SEQ ID NO 51
<211> LENGTH: 32
<212> TYPE: DNA
<213> ORGANISM: Artificial Sequence
<220> FEATURE:
<223> OTHER INFORMATION: primer

<400> SEQUENCE: 51
gagcaccacc tcaccatccc agggaagcta tc                               32
```

```
<210> SEQ ID NO 52
<211> LENGTH: 32
<212> TYPE: DNA
<213> ORGANISM: Artificial Sequence
<220> FEATURE:
<223> OTHER INFORMATION: primer

<400> SEQUENCE: 52
gatggccgtg acgctgaagt accccttcgt ga                              32

<210> SEQ ID NO 53
<211> LENGTH: 25
<212> TYPE: DNA
<213> ORGANISM: Artificial Sequence
<220> FEATURE:
<223> OTHER INFORMATION: primer

<400> SEQUENCE: 53
gaacggtagt tttcgacaaa agacg                                      25

<210> SEQ ID NO 54
<211> LENGTH: 25
<212> TYPE: DNA
<213> ORGANISM: Artificial Sequence
<220> FEATURE:
<223> OTHER INFORMATION: primer

<400> SEQUENCE: 54
gctcaccagc caaaaccgca ccagc                                      25

<210> SEQ ID NO 55
<211> LENGTH: 29
<212> TYPE: DNA
<213> ORGANISM: Artificial Sequence
<220> FEATURE:
<223> OTHER INFORMATION: primer

<400> SEQUENCE: 55
gcaatgtacc acatattcaa ctgcgatac                                  29

<210> SEQ ID NO 56
<211> LENGTH: 29
<212> TYPE: DNA
<213> ORGANISM: Artificial Sequence
<220> FEATURE:
<223> OTHER INFORMATION: primer

<400> SEQUENCE: 56
ccgataccga gtttgaatgg aggaatctc                                  29

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
tcaggccacc cccttgccct tctgt                                      25

<210> SEQ ID NO 58
<211> LENGTH: 25
<212> TYPE: DNA
<213> ORGANISM: Artificial Sequence
<220> FEATURE:
<223> OTHER INFORMATION: primer
```

```
<400> SEQUENCE: 58
atggagtgca gcgtgtgtgc gggtg                                         25

<210> SEQ ID NO 59
<211> LENGTH: 25
<212> TYPE: DNA
<213> ORGANISM: Artificial Sequence
<220> FEATURE:
<223> OTHER INFORMATION: primer

<400> SEQUENCE: 59
atgtctgaag ttatcaagtt taacg                                         25

<210> SEQ ID NO 60
<211> LENGTH: 25
<212> TYPE: DNA
<213> ORGANISM: Artificial Sequence
<220> FEATURE:
<223> OTHER INFORMATION: primer

<400> SEQUENCE: 60
tgaggccttt atggagagct tgttg                                         25
```